(12) United States Patent
Gozes et al.

(10) Patent No.: US 6,613,740 B1
(45) Date of Patent: Sep. 2, 2003

(54) ACTIVITY DEPENDENT NEUROTROPHIC FACTOR III (ADNF III)

(75) Inventors: Illana Gozes, Ramat, Hasharon (IL); Douglas E. Brenneman, Damascus, MD (US); Merav Bassan, Givat-Poleg, Natanya (IL); Rachel Zamostiano, Hod-Hasharon (IL)

(73) Assignees: Ramot University Authority for Applied Research and Industrial Development Ltd., Tel Aviv (IL); The United States of America as represented by the Secretary of the Department of Health and Human Services, Washington, DC (US)

(*) Notice: Subject to any disclaimer, the term of this patent is extended or adjusted under 35 U.S.C. 154(b) by 0 days.

(21) Appl. No.: 09/187,330

(22) Filed: Nov. 6, 1998

Related U.S. Application Data

(63) Continuation-in-part of application No. PCT/US98/02485, filed on Feb. 6, 1998.
(60) Provisional application No. 60/037,404, filed on Feb. 7, 1997.

(51) Int. Cl.$^7$ .......................... A61K 38/00; C07K 7/00; C07K 14/435
(52) U.S. Cl. ............................... 514/12; 514/2; 514/13; 514/14; 514/15; 514/16; 530/324; 530/325; 530/326; 530/327; 530/328; 530/350
(58) Field of Search ....................... 530/350, 324–328; 514/2, 12–16

(56) References Cited

U.S. PATENT DOCUMENTS 5,767,240 A    6/1998 Brenneman et al.

FOREIGN PATENT DOCUMENTS

| WO | WO 92/18140 | 10/1992 |
| WO | WO 96/11948 | 4/1996 |
| WO | WO 98/35042 | 8/1998 |

OTHER PUBLICATIONS

Bassan, M. et al., "VIP–Induced Mechanism of Neuroprotection: The Complete Sequence of a Femtomolar–Acting Activity–Dependent Neuroprotective Protein." *Regulatory Peptides*, vol. 71, No. 2, Aug. 15, 1997.
Bassan, M. et al., "Complete Sequence of a Novel Protein-Containing a Femtomolar–Activity–Dependent Neuroprotective Peptide." *Journal of Neurochemistry*, vol. 72, pp. 1283–1293 (1999).
Beni–Adani, L. et al., "Activity–Dependent Neurotrophic Protein is Neuroprotective in a Mouse Model of Closed Head Injury." Society for Neuroscience, 28$^{th}$ Annual Meeting, Los Angeles, CA, Nov. 7–12, 1998. *Abstracts*, vol. 23, Part 1, p. 1043 (1998).
Brenneman, D.C. and Gozes, I. "A Femtomolar–Acting Neuroprotective Peptide." *Journal of Clinical Investigation*, vol. 97, pp. 229–2307(1996).
Brenneman, D.E. et al. "Identification of a Nine Amino Acid Core Peptide from Activity Dependent Neurotrophic Factor I." Society for Neuroscience, 27$^{th}$ Annual Meeting, New Orleans, LA, Oct. 25–30, 1997. *Abstracts*, vol. 23, Part 2, p. 2250 (1997).
Brenneman, D.E. et al. "Activity–Dependent neutotrophic Factor: Structure–Activity Relationships of Femtomolar–Acting Peptides." *Journal of Pharmacology and Experimental Therapeutics*, vol. 285, pp. 619–627 (1998).
Davidson, A. et al. "Protection Against Developmental Retardation and Learning Impairments in Apolipoprotein E–Deficient Mice by Activity–Dependent Femtomolar–Acting Peptides." Society for Neuroscience, 27$^{th}$ Annual Meeting, New Orleans, LA, Oct. 25–30, 1997. *Abstracts*, vol. 23, Part 2, p. 2250 (1997).
Dibbern, D.A., Jr. et al. "Inhibition of Murine Embryonic Growth by Human Immunodeficiency Virus Envelope Protein and Its Prevention by Vasoactive Intestinal Peptide and Activity–Dependent Neurotrophic Factor." *Journal of Clinical Investigation*, vol. 99, pp. 28377–2841 (1997).
Giladi, E. "Protection Against Developmental and Learning Impairments in Apolipoprotein E–Deficient Mice by Activity–Dependent Femtomolar–Acting Peptides." *Neuroscience Letters*, Supplement 48 S1–S60, P. S19 (1997).
Glazner, G.W. et al. "A 9 Amino Acid Peptide Fragment of Activity–Dependent Neurotrophic Factor (ADNF) Protects Neurons from Oxidative Stress–Induced Death." Society for Neuroscience, 27$^{th}$ Annual Meeting, New Orleans, LA, Oct. 25–30, 1997. *Abstracts*, vol. 23, Part 2, p. 2249 (1997).
Gozes, I. et al. "Stearyl–Norleucine–Vasoactive intestinal Peptide (VIP): A novel VIP Analog for Noninvasive Impotence Treatment." *Endocrinology*, vol. 134, pp. 2125 (1994).
Gozes, I. et al. "Superactive Lipophilic Peptides Discriminate Multiple Vasoactive intestinal Peptide Receptors." *Journal of Pharmacology and Experimental Therapeutics*, vol. 273, pp. 161–167 (1995).

(List continued on next page.)

*Primary Examiner*—Marianne P. Allen
(74) *Attorney, Agent, or Firm*—Townsend and Townsend and Crew LLP

(57) ABSTRACT

The present invention relates generally to Activity Dependent Neurotrophic Factor III (ADNF III), also known as Activity Dependent Neuroprotective Protein (ADNP). More particularly, the present invention relates to nucleic acid sequences encoding ADNF III polypeptides; ADNF III polypeptides encoded by such nucleic acid sequences; antibodies to ADNF III polypeptides; and methods of using such ADNF III polypeptides for the treatment of neurological deficiencies and for the prevention of cell death associated with (1) gp120, the envelope protein from HIV; (2) N-methyl-D-aspartic acid (excito-toxicity); (3) tetrodotoxin (blockage of electrical activity); and (4) β-amyloid peptide, a substance related to neuronal degeneration in Alzheimer's disease.

16 Claims, 31 Drawing Sheets

OTHER PUBLICATIONS

Gozes, I. et al. "Neuroprotective Strategy for Alzheimer Disease: Intranasal Administration of a Fatty Neuropeptide." *Proc. Natl. Acad. Sci. USA*, vol. 93, pp. 427–432 (1996).

Gozes, I. and Brenneman, D.E. "Activity–Dependent Neurotrophic Factor (ADNF)." *Journal of Molecular Neuroscience*, vol. 7, pp. 235–244 (1996).

Gozes, I. et al. "Protection Against Developmental Retardation in Apolipoprotein E–Deficient Mice by a Fatty neuropeptide: Implications for Early Treatment of Alzheimer's Disease." *Journal of Neurobiology*, vol. 33, pp. 329–342 (1997).

Gozes I. et al. "Antiserum to Activity–Dependent Neurotrophic Factor Produces Neuronal Cell Death in CNS Cultures: Immunological and Biological Specificity." *Developmental Brain Research*, vol. 99, pp. 167–175 (1997).

Gozes, I. et al. "The cDNA Structure of a Novel Femtomolar–Acting Neuroprotective Protein: Activity–Dependent–Neurotrophic Factor III (ADNFIII)." Society for Neuroscience, 27$^{th}$ Annual Meeting, New Orleans, LA, Oct. 25–30, 1997. *Abstracts*, vol. 23, Part 2, p. 2250 (1997).

Gozes, I. et al. A Femtomolar–Acting Activity–Dependent Neuroprotective Protein (ADNP). *Neuroscience Letters*, Supplement 48 S1–S60, p. S21 (1997)–.

Hill, J.M. et al. "Learning Impairment in Adult Mice Produced by Early Embryonic Administration of Antiseum to Activity–Dependent Neurotrophic Factor (ADNF)." Society for Neuroscience, 27$^{th}$ Annual Meeting, New Orleans, LA, Oct. 25–30, 1997. *Abstracts*, vol. 23, Part 2, p. 2250 (1997).

Lilling, G. et al. "Inhibition of Human Neuroblastoma Growth by a Specific VIP Antagonist." *Journal of Molecular Neuroscience*, vol. 5, pp. 231–239 (1995).

McKune, S.K. et al. "Localization of mRNA for Activity–Dependent Neurotrophic Factor III (ADNF III) in mouse Embryo and Adult CNS." Society for Neuroscience, 27$^{th}$ Annual Meeting, New Orleans, LA, Oct. 25–30, 1997. *Abstracts*, vol. 23, Part 2, p. 2249 (1997).

Nelbock, P. et al. A cDNA for a Protein that Interacts with the Human Immunodeficiency Virus Tat Transactivator. *Science*, vol. 248, pp. 1650–1653 (1990).

Pelsman, A. et al. "In Vitro Degeneration of Down Syndrome neurons is Prevented by Activity–Dependent Neurotrophic Factor–Derived Peptides." Society for Neuroscience, 28$^{TH}$ Annual Meeting, Los Angeles, CA, Nov. 7–12, 1998. *Abstracts*, vol. 24, p. 1044 (1998).

Gozes, et al., "A Novel Signaling Molecule for Neuropeptide Action: Activity–dependent Neuroprotective Protein"; Annals of the New York Academy of Sciences, 897:125–135 (1999).

Nagase, et al., "Prediction of the Coding Sequences of Unidentified Human Genes. XI. The Complete Sequences of 100 New cDNA Clones from Brain Which Code for Large Proteins in vitro"; DNA Research 5:5:277–286 (1998).

GenBank Accession No. AB018327 from the DNA Data Bank of Japan (DDBJ) (released Nov. 17, 1998).

FIG. 1A.

```
1882  GAGGAGGAGGAGGAGGAGGATGGTTCAAAATATGAAACTATCCATTTGACTGAGGAACCAGCCAAATTAATGCATGATGCCTCTGATAGTGAG   660
       E   E   E   E   E   E   D   G   S   K   Y   E   T   I   H   L   T   E   E   P   A   K   L   M   H   D   A   S   D   S   E
1981  GTAGACCAAGATGATGTAGTTGAGTGGAAAGATGGTGCTTCACCATCTGAGAGTGGGCCTGGTTCCCAACAAATCTCAGACTTTGAGGATAATACATGT   693
       V   D   Q   D   D   V   V   E   W   K   D   G   A   S   P   S   E   S   S   G   P   G   S   Q   Q   I   S   D   F   E   D   N   T   C
2080  GAAATGAAACCAGGAACCTGGTCTGATGAGTCTTCCCAGAGTCAAGAGATGCAAGCCAGTCAGTCGCCAAAAAAAGGCTACAGTGCAAGATGAC   726
       E   M   K   P   G   T   W   S   D   E   S   S   Q   S   E   D   A   R   S   S   K   P   A   A   K   K   K   A   T   V   Q   D   D
2179  ACAGAGCAGTTAAAATGAAGAATAGTTCCTATGGAAAAGTTGAAGGGTTTTGGTCCAAGGACCAGTCACGTGGAAAATGCATCTGAGAATGCAGAG   759
       T   E   Q   L   K   W   K   N   S   S   Y   G   K   V   E   G   F   W   S   K   D   Q   S   Q   W   E   N   A   S   E   N   A   E
2278  CGCTTACCAAACCCACAGATTGAGTGGCAGAATAGCACAATTGACAGTTTGACGAGGACGCAGTTGCTGACTGACGGAGTTGCTGATCCCATG   792
       R   L   P   N   P   Q   I   E   W   Q   N   S   T   I   D   S   E   D   D   G   E   Q   F   D   S   M   T   D   G   V   A   D   P   M
2377  CATGGCAGCTTAACTGGAGTGAAGCTGAGCAGCCAGCAAGCCTGA                                                       806
       H   G   S   L   T   G   V   K   L   S   S   Q   Q   A   *

Single Underline - homologies to HSP60 of ADNP
Dotted Underline - homologies to PIF1 of ADNP
Double Underline - Glycosilation site (amino acid no. 96-98, 183-185, 371-373, 404-406, 554-556, 584-586, 734-
736, 753-755, 770-772)
Bold + Italic - represents two motifs:
       1. Glutaredoxin active site (amino acid no. 211-221)
       2. Zinc finger C2h2 type, domain (amino acid no. 211-232)
```

FIG. 1B.

Neuroblastoma (NMB)

SENSE

```
  1 CATTGGGCCG ACGTCGCATG CTCCCGGCCG CCATGGCCGC GGGATTACCT
 51 GCAGCAAAAC AACTATGGAG TCAAATCTGT AGGCCAGGGT TACAGTGTTG
101 GTCAGTCAAT GAGACTGGGT CTAGGTGGCA ACGCACCAGT TTCCATTCCT
151 CAACAATCTC AGTCTGTAAA GCAGTTACTT CCAAGTGGAA ACGGAAGGTC
201 TTATGGGCTT GGGTCAGAGC AGAGGTCCCA GGCACCAGCA AGATACTCCC
251 TGCAGTCTGC TAATGCCTCT TCTCTCTCAT CGGGCCAGTT AAAGTCTCCT
301 TCCCTCTCTC AGTCACAGGC ATCCAGAGTG TTAGGTCAGT CCAGTTCCAA
351 ACCTGCTGCA GCTGCCACAG GCCCTCCCCC AGGTAACACT TCCTCAACTC
401 AAAAGTGGAA AATATGTACA ATCTGTAACG AGCAATCACT AGTGCGGCCG
451 CCTGCAGGTC GACCATATGG GAGAGCTCCC AACGCGTTGG ATGCATAGCT
501 TGAGTATTCT ATAGTGTCAC CTAAATAGCT TGGCGTAATC ATGGTCATAG
551 CTGTTTCCTG TGTGAAATTG TTATCCGCTC ACAATTCCAC ACAACATACG
601 AACCGGAAGC ATAAAGTGTA AAGCCTGGGG TGCCTAATGA ATGAGCTAAC
651 TCACATTAAT TGCGTTGCGC TCACTGCCCG CTTTCCAATC NGGAAACTGT
701 CGTGCCAACT GCATTAATGA ATCGGCCAAC GCGCGGGGAA AAGCGGTTTG
751 CGTATTGGGC GCTCTTCCGC TTCCTCGCTC AATGAATCCC TGCGCTCNGT
801 CCTTCCGNTG CGGNNAACGG TATCACTCAC TCNAATT
```

ANTISENSE

```
  1 ATNNATATCA AGCTATGCAT CCAACGCGTT GGGAGCTCTC CCATATGGTC
 51 GACCTGCAGG CGGCCGCACT AGTGATTGCT CGTTACAGAT TGTACATATT    PRIMER 44
101 TTCCACTTTT GAGTTGAGGA AGTGTTACCT GGGGGAGGGC CTGTGGCAGC
151 TGCAGCAGGT TTGGAACTGG ACTGACCTAA CACTCTGGAT GCCTGTGACT
201 GAGAGAGGGA AGGAGACTTT AACTGGCCCG ATGAGAGAGA AGAGGCATTA
251 GCAGACTGCA GGGAGTATCT TGCTGGTGCC TGGGACCTCT GCTCTGACCC
301 AAGCCCATAA GACCTTCCGT TTCCACTTGG AAGTAACTGC TTTACAGACT
351 GAGATTGTTG AGGAATGGAA ACTGGTGCGT TGCCACCTAG ACCCAGTCTC
401 ATTGACTGAC CAACACTGTA ACCCTGGCCT ACAGATTTGA CTCCATAGTT   -PRIMER 105
451 GTTTTGCTGC AGGTAATCCC GCGGCCATGG CGGCCGGGAG CATGCGACGT
```

FIG. 5B-1.

```
501 CGGGCCCAAT TCGCCCTATA GTGAGTCGTA TTACAATTCA CTGGCCGTCG

551 TTTTACAACG TCGTGACTGG GAAAACCCTG GCGTTACCCA ACTTAATCCC

601 CTTGCAGCAC ATCCCCCTTT CGCCAGCTGG CGTTAATAAC GAAGAAGCCC

651 GCACCGATCG CCCTTCCCAA CAGTTGCGCA GCCTGAATGG CGAATGGACG

701 CGCCTGTTAG CGCGCATTAA ACCCCGCGGG TGTTGTGGTT ACGCCGCAGC

751 GTGACCGCTA CACTTGCCAC CCCCTAACGC CCGCTCCTTT CCCTTTCTTC

801 CTTCCTTTCT CGCCACGTCC CCCGNTTTCC CCGTCCAACT CTAAATCGGT
```

FIG. 5B-2.

```
  1  MSNVHLQQNNYGVKSVGQSYGVGQSVRLGLGGNAPVSIPQQSQSVKQLLP   50
     ||·|||||||||||||||| |  ||||·|||||||||||||||||||||||
 20  MSSVHLQQNNYGVKSVGQGYSVGQSMRLGLGGNAPVSIPQQSQSVKQLLP   69

51  SGNGRSFGLGAEQRPPAAARYSLQTAN.TSLPPGQVKSPSVSQSQASRVL   99
     ||||||:|||·|||   ||||||·||  ||  | ·||||·| |||||||
 70  SGNGRSYGLGSEQRSQAPARYSLQSANASSLSSGHLKSPSLSHSQASRVL  119

100  GQSSSKPPPAATGPPPSNHCATQKWKICTICNELFPENVYSVHFEKEHKA  149
     |||||||   ||||||| ·|||||||||||||||||||||||||||||||
120  GQSSSKPAAATGPPPGNTSSTQKWKICTICNELFPENVYSVHFEKEHKA   169

150  EKVPAVANYIMKIHNFTSKCLYCNRYLPTDTLLNHMLIHGLSCPYCRSTF  199
     |||||||||||||||||||||||||||||||||||||||||||||||||
170  EKVPAVANYIMKIHNFTSKCLYCNRYLPTDTLLNHMLIHGLSCPYCRSTF  219

200  NDVEKMAAHMRMVHIDEEMGPKTDSTLSFDLTLQQGSHTNIHLLVTTYNL  249
     |||||||||||||||||||||||||||||||||||||||||||||||||
220  NDVEKMAAHMRMVHIDEEMGPKTDSTLSFDLTLQQGSHTNIHLLVTTYNL  269

250  RDAPAESVAYHAQNNAPVPPKPQPKVQEKADVPVKSSPQAAVPYKKDVGK  299
     ||||||||||||||| |||||||||||||||:||||||||||||||||||
270  RDAPAESVAYHAQNNPPVPPKPQPKVQEKADIPVKSSPQAAVPYKKDVGK  319

300  TLCPLCFSILKGPISDALAHHLRERHQVIQTVHPVEKKLTYKCIHCLGVY  349
     |||||||||||||||||||||||||||||||||||||||||||||||||
320  TLCPLCFSILKGPISDALAHHLRERHQVIQTVHPVEKKLTYKCIHCLGVY  369

350  TSNMTASTITLHLVHCRGVGKTQNGQDKTNAPSRLNQSPGLAPVKRTYEQ  399
     |||||||||||||||||||||||||||||||||||||||| |||||||||
370  TSNMTASTITLHLVHCRGVGKTQNGQDKTNAPSRLNQSPSLAPVKRTYEQ  419

400  MEFPLLKKRKLEEDADSPSCFEEKPEEPVVLALDPKGHEDDSYEARKSFL  449
     ||||||||||::|·|||| |||||||||||||||||||||||||||||||
420  MEFPLLKKRKLDDDSDSPSFFEEKPEEPVVLALDPKGHEDDSYEARKSFL  469

450  TKYFNKQPYPTRREIEKLAASLWLWKSDIASHFSNKRKKCVRDCEKYKPG  499
     |||||||||||||||||||||||||||||||||||||||||||||||||
470  TKYFNKQPYPTRREIEKLAASLWLWKSDIASHFSNKRKKCVRDCEKYKPG  519

500  VLLGFNMKELNKVKHEMDFDAEWLFENHDEKDSRVNASKTVDKKHNLGKE  549
     |||||||||||||||||||||||||||||||||||||||| ||| |||||
520  VLLGFNMKELNKVKHEMDFDAEWLFENHDEKDSRVNASKTADKKLNLGKE  569

550  DDSFSDSFEHLEEESNGSGSPFDPVFEVEPKIPSDNLEEPVPKVIPEGAL  599
     ||| |||||·|||||| ||||||||||||||·|| || | ||||||| |
570  DDSSSDSFENLEEESNESGSPFDPVFEVEPKISNDNPEEHVLKVIPEDAS  619

600  ESEKLDQKEEEEEEEEEDGSKYETIHLTEEPAKLMHDASDSEVDQDDVVE  649
     ||       ||·:::·|||||||||||||| ||||·|||||||||||||
620  ES.......EEKLDQKEDGSKYETIHLTEEPTKLMHNASDSEVDQDDVVE  662

650  WKDGASPSESGPGSQQISDFEDNTCEMKPGTWSDESSQSEDARSSKPAAK  699
     |||||||||||||||:|||||||||||||||||||||||||||||||||
663  WKDGASPSESGPGSQQVSDFEDNTCEMKPGTWSDESSQSEDARSSKPAAK  712

700  KKATVQDDTEQLKWKNSSYGKVEGFWSKDQSQWENASENAERLPNPQIEW  749
     ||||·| |  ||||||||||||||||||||||·||||| ||| |||||||
713  KKATMQGDREQLKWKNSSYGKVEGFWSKDQSQWKNASENDERLSNPQIEW  762
```

*FIG. 5C-1.*

```
750 QNSTIDSEDGEQFDSMTDGVADPMHGSLTGVKLSSQQA  787
    ||||||||||||| |||||  ||||||  |||||||||
763 QNSTIDSEDGEQFDNMTDGVTEPMHGSLAGVKLSSQQA  800
```

SIZE
(KB)

ADNP
mRNA  →  ▬ ▬ ▬  — 5

— 2.1

ACTIN
mRNA  →  ▬ ▬ ▬

```
        E   E   P   V   P   K   V   I   P   E   G   A   L   E   S   S   E   K   L   D   Q   K   E   E   E   E   E   E   E   E   D   G   S           660
1981  AAATATGAAACTATCCATTTGACTGAAGGAGCCCTGGAATCATGATGCCTCTGATAGTGAGGTAGACCAAGATGATGTAGTTGAGTTGGAAAGAT
        K   Y   E   T   I   H   L   T   E   E   P   A   K   L   M   H   D   A   S   D   S   E   V   D   Q   D   D   V   V   E   W   K   D           693
2080  GGTGCTTCACCATCTGAGAGTGGGCCTGGTCCCAACAAATCTCAGACTTTGAGGATAATACATGTGAAATGAAACCAGGAACCTGGTCTGATGAGTCT
        G   A   S   P   S   E   S   G   P   G   S   Q   Q   I   S   D   F   E   D   N   T   C   E   M   K   P   G   T   W   S   D   E   S           726
2179  TCCCAGAGTGAAGATGCAAGGAGCAGTAAGCCAGTGCCAAAAAAAAGGCTACAGTGCAAGATGACACAGCCAGTTAAAATGGAAGAATAGTTCCTAT
        S   Q   S   E   D   A   R   S   S   K   P   A   K   K   K   A   T   V   Q   D   D   T   E   Q   L   K   W   K   K   N   S   Y           759
2278  GGAAAAGTTGAAGGGTTTTGGTCCAAGACCAGTCATCTGAGAATGCATGGGAAATGCATCTGAGAATGCAGCGCTTACCAAACCCACAGATTGAGTGGCAGAAT
        G   K   V   E   G   F   W   S   K   D   Q   S   Q   W   E   N   A   S   E   N   A   E   R   L   P   N   P   Q   I   E   W   Q   N           792
2377  AGCACCAATTGACAGTGAGGACGGGAGCAGTGACACTTTGACGACGATGCTGATCCCATGCATGCGGAGTTGCTAACTGGAGCTTAACTGGAGTGAAGCTGAGCAGC
        S   T   I   D   S   E   D   G   E   Q   F   D   S   M   T   D   G   V   A   D   P   P   M   H   G   S   L   T   G   V   K   L   S   S       825
2476  CAGCAAGCCTGA                                                                                                                                    828
        Q   Q   A   *

Single Underline - homologies to HSP60 of ADNP
Double Underline - Glycosilation site (amino acid no. 118-120, 205-207, 393-395, 426-428, 576-578, 606-608, 756-758,
775-777, 792-794)
Bold + Italic - represents two motifs:
    1.   Glutaredoxin active site (amino acid no. 233-243)
    2.   Zinc finger C2h2 type, domain (amino acid no. 233-254)

Bold - potential proteolytic cleavage sites.

Bold + Underline - putative signal peptide
```

```
1927  TCTGAGGAGAAGCTAGACCAAAAAGAGGATGGTTCAAAATACGAAACTATTCATTTGACTGAGGAACCAACCAAACTAATGCACAATGCATCTGATAGT   675
       S  E  E  K  L  D  Q  K  E  D  G  S  K  Y  E  T  I  H  L  T  E  E  P  T  K  L  M  H  N  A  S  D  S
2026  GAGGTTGACCAAGACGATGTTGTTGAGTGGAAAGACGGTGCTTCTCCATCTGAGAGTGGGCCTGGATCCCAACAAGTGTCAGACTTTGAGGACAATACC   708
       E  V  D  Q  D  D  V  V  E  W  K  D  G  A  S  P  S  E  S  G  P  G  S  Q  Q  V  S  D  F  E  D  N  T
2125  TGCGAAATGAAACCAGGAACCTGGTCTGACGAGTCTTCCCAAAGGCAAGGAGAGCAAGTAAGCCAGTGCCAAAAAAAAGGCTACCATGCAAGG         741
       C  E  M  K  P  G  T  W  S  D  E  S  S  Q  S  E  D  A  R  S  S  K  P  A  A  K  K  K  G  Y  H  A  R
2224  TGA
       *

Single underline - homologies to hsp60 of ADNP.
Double underline - Glycosilation sites.
Bold + Double underline -
    1.  Zinc finger C2h2 type, domains.
    2.  Glutaredoxin active site (amino acid no. 234-238)

Bold - potential proteolic cleavage site.
```

H7 clone

```
       AAAACCAGGACTATCGGACAAAACCTTTCTGCTGCAGCCGCTTGTCCATTTCCTCAAAATTCTTCTCTGCCTACAAAAGTCATTTCGCAATGTCCAT
       AGTGAAGAGACTTTGAAATAGGATTCTCCTTAATTGCCCCTACTGTACCTTCAATGCAGACAAAAGACTTTGGAAACACACATTAAAATATTTCATGCT
       CCGAACGCCAGCGCACCAAGTAGCAGCTTCAGCACTTTCAAAGATAAACCAAAATGATGGCCTTAAACTTAAGCAGGCCTTAAACTTAAGCAGGTGACAGTGTAGAGCAAGCT
       GTTTATTACTGTAAGAAGTGCACTTACCGAGATCCTCTTTATGAAATAGTTAGGAAGACACATTTTCAGCATGTGGCAGCACCTTAC
       ATAGCAAAGGCAGGAGAAAATCACTCAATGGGCAGTCCCCTTAGGCTCGAATGCCCGAGAAGAGAGTAGTATTCACTGTATTCACTGCAAGCGATGCCTTTTCATG
                                                                                                  M
       CCAAAGTCCTATGAAGCTTTGGTACAGCATGTCATCGAGAACGTATCAGTCACTGCCATGATTGGGCACACAAATGTAGTGTT                       15
     P  K  S  Y  E  A  L  V  Q  H  V  I  E  D  H  E  R  I  G  Y  Q  V  T  A  M  I  G  H  T  N  V  V
  54   CCCGATCCAAACCCTTGATGCTAATTGCTCCCAAACCTCAAGCAAGAAGACATGGGACCTCCACCAGGATCGGTTCCCTTGCTTCTGAAATGTC          48
     P  R  S  K  P  L  M  L  I  A  P  K  P  Q  D  K  K  S  M  G  L  P  P  R  I  G  S  L  A  S  G  N  V
  45   CGGTCTTTACCATCACAGCAGATGGTGAATCGACTCTCAATTCTACAGGAGTCAACATGATGTCAGTGTTCATCTGCAG                          81
     R  S  L  P  S  Q  Q  M  V  N  R  L  S  I  P  K  P  N  L  N  S  T  G  V  N  M  M  S  S  V  H  L  Q
 144   CAGAACAACTATGGCTCAAATCTGTAGGCCAGGTTACAGTGTGTCAGTCAATGAGACTGGGTCTAGGTGGCAACGCACCAGTTTCCATTCCTCAA         114
     Q  N  N  Y  G  V  K  S  V  G  Q  G  Y  S  V  G  Q  S  M  R  L  G  G  N  A  P  V  S  I  P  Q
 243   CAATCTCAGTCTGTAAAGCAGTTACTTCCAGGTCTTATGGGCCAGTTAAAGTCTCCTCCAGTCAGCATCCAGAGTGTTAGGTCAGTCCAGTTCCAAA       147
     Q  S  Q  S  V  K  Q  L  L  P  S  G  N  G  R  S  Y  G  L  G  S  E  Q  R  S  Q  A  P  A  R  Y  S  L
 342   CAGTCTGCTAATGCCTCTCTCTCATCGGGCCCTCCCCCAGGTAACACTGGGAAAGCTGAGAAAGTCCCAGCAGTAGCCAACTACAATTTACTAGCAAATGCCTCTAC  180
     Q  S  A  N  A  S  S  L  S  S  G  Q  L  K  S  P  S  L  S  Q  S  Q  A  S  R  V  L  G  Q  S  S  S  K
 441   CCTGCTGCAGCTCACTTCGAAAAGCTACTTCCACAGATACTCTGCTCAACATATGTTAATTCATGCCGTTCAACTTTCAATGATGTGGAAAAG          213
     P  A  A  A  T  G  P  P  P  G  N  T  S  T  Q  K  W  K  I  C  N  E  L  F  P  E  N  V
 540   TATAGTGTGCACTTCGAAAAAGAACATAAAGCTGAGAAAGTCCCAGCAGTAGCCAACTATGTTAATTCATGCCGTTCAACTTTCAATGATGTGGAAAAG        246
     Y  S  V  H  F  E  K  E  H  K  A  E  K  V  P  A  V  A  N  Y  I  M  K  I  H  N  F  T  S  K  C  L  Y
 639   TGTAATCGCTATTTACCCACAGACTTCTGCTCAACATATGTTAATTCATGGCCGTTCAACTTTGATTGACATTGCAGCAGGGTAGTCAC              279
     C  N  R  Y  L  P  T  D  T  L  L  N  H  M  L  I  H  G  L  S  C  P  Y  C  R  S  T  F  N  D  V  E  K
 738   ATGGCCGCACACATGCGGATGGTTCACATTGATGAAGAGATGGGACCTAAAACAGATTCTACTTTGAGTTTGATTTGACATTGCAGCAGGGTAGTCAC        312
     M  A  A  H  M  R  M  V  H  I  D  E  E  M  G  P  K  T  D  S  T  L  S  F  D  L  T  L  Q  Q  G  S  H
 837   ACTAACATCCATCTCCTGGTAACTACATAAATCTGAGGGATGCCTATAAAAAGATGTTGGGAAAAACCCTTTGTCCT                           345
     T  N  I  H  L  V  T  T  Y  N  L  R  D  A  P  A  E  S  V  A  Y  H  A  Q  N  N  P  P  V  P  P  K
 936   CCACAGCCAAAGGTTCAGGAAAAGGCAGATATCCCTGTAAAAAGTTCACCTGCACATCGATGAGAGGCACCAAGTTATTCAGACGGTTCATCCAGTTGAGAAA       378
     P  Q  P  K  V  Q  E  K  A  D  I  P  V  K  S  S  P  Q  A  A  V  P  Y  K  K  D  V  G  K  T  L  C  P
1035   CTTTGCTTTCAATCCTAAAGGACCCATATCTGATGCACTTGCACATCATCTGCGTGTATACACCAGCAACATGACCGCCTCAACTCACTCTAGTTCACTGCAGGGGCGTTGGA    411
     L  C  F  S  I  L  K  G  P  I  S  D  A  L  A  H  H  L  R

FIG. 13B.

```
3213  AAAAACAAAAACTGGTATTTCAGATCTGTTTCTGAAATCTTTTAAGCTAAAATCACATGCAAGAATTGACTTTGCAGCTACTAATTTTGACACCTTTT

3312  AGATCTGTATAAAAGTGTGTTGTGTTGAAGCAGCAAACCAATGAGTGCTGCATTTTGGATATTTAGTTTTATCTTTAGTTCAACACCATCATGGTGGAT

3411  TCATTTATACCATCTAATATATGACACACTGTTGTAGTATGTATAATTTTGTGATCTTTATTTCCCTTTGTATTCATTTAAGCATCTAAATAAATTG

3510  CTGTATTGTGCTTAATGTAAAAAAAAAAAAAAAA
```

Bold: Putative initiator methionine
<u>Bold underlined</u>: initiator methionine in the mouse sequence (numbers of nucleic acids and amino acids is according to the mouse sequence).
<u><u>*Bold, italic, double underline*</u></u>: polymorphic site

FIG. 13C.

```
  1 AATTGTTGGG TGATGAGAAA GAGAGCTGTT TGCCTTCCGT GTTGGTCATC

51 AAGGTCTGCG TGCATTGCAA CAGTGTCACC TGTGAGTTCC TGTGTCTGAA

101 GCCGAGAAGA TCCACAAAAT GAGGCTTTTC CATAGTTGGT TTGTGTTTT

151 AACAAGAAAA TGGAGAGGCT TTTGTTTGT TTTGTTTTT GTTTTTTGC

201 CTCTGACTTC TCTCTGAAAC CAGCCAACAA GTACAACTAG CAATTTTTAA

251 AGATTTAGCA AGAACTTGCA CTGAGTTTTC ATTTACAGGA GCACAAATAA

301 AAATATTTGA TTCAAAAATG CATCTGAGTT CTTTTAATTT TTCCTGCAGG

351 AGAAACCTCT AAAAGTCATT GCCTTGCAGA GTTTCTGGGA ATGCCTGGGG

401 GAGGAGCCTG GAACTTGTAA CTGCTTGCCT TGAGTGGCCT TCTCACTCTG

451 GTTCTGTTC TGTTTTGTTT CGTTTGTTTT TT
```

FIG. 14.

Polymorphism

```
H6  clone      GAGTTAAACT GAGCAGCCAA CAGGCCTAAG TGCCAGGTTC CCTGGCATTG
H10 clone      GAGTTAAACT GANCANCCAN CAGGCCTAAG TGCCAGGTTN CCTGGCGTTG
H3  clone      GAGTTAAACT GAGCAGCCAA CAGGCCTAAG TGCCAGGTTC CCTGGCGTTG
H12 clone      GAGTTAAACT GAGCAGCCAA CAGGCCTAAG TGCCAGGTTC CCTGGCGTTG
H7  clone      GAGTTAAACT GAGCAGCCAA CAGGCCTAAG TGCCAGGTTC CCTGGCATTG
H4  clone      GAGTTAAACT GAGCAGCCAA CAGGCCTAAG TGCCAGGTTC CCTGGCGTTG
H2  clone      GAGTTAAACT GAGCAGCCAA CAGGCCTAAG TGCCAGGTTC CCTGGCATTG
```

Polymorphic site:  A → G transition

FIG. 18.

ACTIVITY DEPENDENT NEUROTROPHIC FACTOR III (ADNF III)

CROSS REFERENCE TO RELATED APPLICATIONS

The present application is a continuation-in-part of the PCT Application No. PCT/US98/02485, filed Feb. 6, 1998, which in turn is a continuation-in-part of provisional U.S. Application No. 60/037,404, filed Feb. 7, 1997, each of which is incorporated herein by reference.

STATEMENT REGARDING FEDERALLY SPONSORED RESEARCH OR DEVELOPMENT

Not applicable.

FIELD OF THE INVENTION

The present invention relates generally to Activity Dependent Neurotrophic Factor III (ADNF III), also known as Activity Dependent Neuroprotective Protein (ADNP). More particularly, the present invention relates to nucleic acid sequences encoding ADNF III polypeptides; ADNF III polypeptides encoded by such nucleic acid sequences; antibodies to ADNF III polypeptides; and methods of using such ADNF III polypeptides for the treatment of neurological deficiencies and for the prevention of cell death associated with (1) gp120, the envelope protein from HIV; (2) N-methyl-D-aspartic acid (excito-toxicity); (3) tetrodotoxin (blockage of electrical activity); and (4) β-amyloid peptide, a substance related to neuronal degeneration in Alzheimer's disease.

BACKGROUND OF THE INVENTION

Neuronal division, survival and differentiation are dependent during development on a diverse group of protein and peptide growth factors. Included in this group of regulatory molecules are recognized trophic factors, such as nerve growth factor (NGF) (Levi-Montalcini, *Differentiation*, 13:51–53 (1979)), ciliary neurotrophic factor (CNTF) (Lin et al., *Science* 24:1023–1025 (1989)), fibroblast growth factor (FGF) (Wallicke et al., *J. Neurosci*. 11:2249–2258 (1991)), insulin-like growth factors 1 and 2 (IGFs 1 and 2) (Ishii et al., *Pharmacol. & Ther*. 62:125–144 (1994)), brain derived neurotrophic factor (BDNF) (Laibrock et al., *Nature* 341:149–152 (1989)), glial derived neurotrophic factor (GDNF) (Lin et al., *Science* 260:1130–1132 (1993)), and neurotrophin-3 and neurotrophin-4/5 (Henderson et al., *Nature* 363:266–269 (1993)). In addition, cytokines also have neurotrophic properties (Brenneman et al., *J. Neurochem*. 58:454–460 (1992); Patterson, *Curr. Opin. Neurobiol*. 2:91–97 (1992)). Although many of the classic growth factors were first recognized as playing important trophic roles in neuron/target cell interactions, it is now clear that glial cells in the central nervous system (CNS) express most of these growth factors/cytokines, and that these support cells play significant roles during development and nerve repair/regeneration.

In this regard, efforts have been made to understand the role of neuropeptides in regulating the release/expression of glia-derived trophic substances and to identify new glial molecules that contribute to the survival of developing CNS neurons. In particular, efforts have been made to understand the role of trophic support for activity-dependent neurons in the CNS. The activity-dependent neurons are a class of neurons that die during electrical blockade due to a reduction of soluble trophic materials in their environment (Brenneman et al., *Dev. Brain Res*. 9:13–27 (1993); Brenneman et al., *Dev. Brain Res*. 15:211–217 (1984)). Electrical blockade has been demonstrated to inhibit the synthesis and release of trophic materials into the extracellular milieu of CNS cultures (Agostan et al., *Mol. Brain. Res*. 10:235–240 (1991); Brenneman et al., *Peptides* 6(2):35–39 (1985)). Included in this trophic mixture is vasoactive intestinal peptide (VIP) (Brenneman et al., *Peptides*, supra (1985); Brenneman et al., *Proc. Natl. Acad. Sci. USA* 83:1159–1162 (1986)).

The 28-amino acid peptide VIP (Said et al., *Ann. NY Acad. Sci*. 527:1–691 (1988)), has been associated with cellular protection in sensory neurons, axotomized sympathetic neurons and acutely injured lung and airways (see, e.g., Gressens et al., *J. Clin. Invest*. 100:390–397 (1997)). Indeed, the lack of regulation of VIP expression observed in these injured or inflamed systems probably represents an adaptive response that limits damage and promotes recovery.

VIP has been shown to interact with high affinity receptors present on glial cells (Gozes et al., *J. Pharmacol. Exp. Therap*. 257:959–966 (1991)), resulting in the release of survival-promoting substances (Brenneman et al., *J. Cell. Biol*. 104:1603–1610 (1987); Brenneman et al., *J. Neurosci. Res*. 25:386–394 (1990)), among which are a glial-derived cytokine IL-1-α (Brenneman et al., *J. Neurochem*. 58:454–460 (1992); Brenneman et al., *Int. J. Dev. Neurosci*. 13:137–200 (1995)), and protease nexin I, a serine protease inhibitor (Festoff et al., *J. Neurobiol*. 30:255–26 (1995)). However, the neuronal survival-promoting effects of the VIP-conditioned medium were observed at very low concentrations that could not be attributed to IL-1 or protease nexin I released from astroglia. Therefore, efforts have been made to identify other survival-promoting proteins released from glial cells stimulated by VIP.

In doing so, a novel neuroprotective protein secreted by astroglial in the presence of VIP was discovered (Brenneman & Gozes, *J. Clin. Invest*. 97:2299–2307 (1996); Gozes & Brenneman, *J. Molec. Neurosci*. 7:235–244 (1996)). The neurotrophic protein was isolated by sequential chromatographic methods combining ion exchange, size separation and hydrophobic interaction. This neuroprotective protein (mol. mass, 14 kD and pI, 8.3±0.25) was named Activity Dependent Neurotrophic Factor (ADNF or ADNF I) for two reasons: (1) a blockade of spontaneous electrical activity was necessary to detect the neuroprotective action of this substance in dissociated spinal cord cultures; and (2) VIP, a secretagogue for ADNF, was released during electrical activity, making the presence of ADNF in the extracellular milieu indirectly dependent on spontaneous activity. ADNF was found to exhibit neuroprotection at unprecedented concentrations. More particularly, femtomolar concentrations of ADNF were found to protect neurons from death associated with a broad range of toxins, including those related to Alzheimer's disease, the human immunodeficiency virus (HIV), excitotoxicity, and electrical blockade (see, e.g., Gozes et al., *Dev. Brain Res*. 99:167–175 (1997)).

During the course of studies directed to the structural characteristics of ADNF, an active peptide fragment of ADNF was discovered. This active peptide, 9-amino acids derived from ADNF (ADNF-9), was found to have strong homology, but not identity, to an intracellular stress protein: heat shock protein 60 (hsp60). Another peptide, ADNF-14, which comprises ADNF-9, was also found to be active, as were other derivatives of ADNF-9. Moreover, ADNF-9 was shown to mimic the potency of the parent protein, while exhibiting a broader range of effective concentrations as compared to the parent protein. In addition, ADNF-9, like ADNF, has been shown to prevent neuronal cell death associated with the envelope protein (gp120) from HIV (see Dibbern et al., *J. Clin. Invest.* 99:2837–2841 (1997)), with excitotoxicity (N-methyl-D-aspartate), with the β-amyloid peptide (putative cytotoxin in Alzheimer's disease), and with tetrodotoxin (electrical blockade) (see Brenneman & Gozes, *J. Clin. Invest.* 97:2299–2307 (1996)).

The discovery of ADNF has provided additional knowledge regarding the neuroprotective action of VIP (Gozes & Brenneman, *Mol. Neurobiol.* 3:201–236 (1989); Said, *J. Clin Invest.* 97:2163–2164 (1996)). Moreover, the neurotrophic properties of the ADNF polypeptide have significant therapeutic and diagnostic implications. The discovery that ADNF activity can be mimicked by a 9-amino acid peptide is predicted to facilitate innovative drug design for the treatment of the neurological symptoms associated with HIV infection, Alzheimer's disease, and other prevalent neuro-degenerative diseases. Although ADNF, ADNF-9, and ADNF-14 have unlimited potential as neuroprotectants, it would still be advantageous to identify other survival-promoting proteins released from glial cells stimulated by VIP.

SUMMARY OF THE INVENTION

The present invention relates to the discovery of a nucleic acid encoding a novel neuroprotective polypeptide, i.e., Activity Dependent Neurotrophic Factor III (ADNF III), also called Activity Dependent Neuroprotective Protein (ADNP). As with the previously described ADNF I, ADNF III exhibits potent neuroprotective effects, with the $EC_{50}$ of such neuroprotective effects being in the femtomolar range. Based on the recognized homology between ADNF I and hsp60, a heat shock protein, and PIF1, a DNA repair protein, these two epitopes were utilized to prepare antibodies which, in turn, were used to screen a mouse cDNA-expression library to identify the new neuroprotective polypeptide ADNF III. One mouse ADNF III cDNA clone consists of about 2418 base pairs of an open reading frame, which encodes an ADNF III polypeptide of about 806 amino acids, pI 5.85 (nucleotide sequence, SEQ ID NO:4; amino acid sequence, SEQ ID NO:3, see FIG. 1). An additional mouse cDNA has been cloned, encoding an ADNF III polypeptide of about 828 amino acids, pI 5.99 (nucleotide sequence, SEQ ID NO:54; amino acid sequence, SEQ ID NO:55; see FIG. 11). Human cDNAs encoding ADNF III have also been cloned ("H3'" nucleotide sequence, SEQ ID NO:2; "H3'" amino acid sequence, SEQ ID NO:1; "H3" nucleotide sequence, SEQ ID NO:56 and FIG. 12; "H3" amino acid sequence, SEQ ID NO:57 and FIG. 12; "H7" nucleotide sequence, SEQ ID NO:58 and FIG. 13; and "H7" amino acid sequence, SEQ ID NO:59 and FIG. 13). The mouse and human cDNAs demonstrate about 88.7% homology at the nucleotide level (compare SEQ ID NOS:54 and 58). The promoter sequence for ADNF III has also been cloned (SEQ ID NO:60 and FIG. 14).

Based on the homology between ADNF I and hsp60 to ADNF III, an eight-mer ADNF III polypeptide was synthesized that exhibited structural homology to hsp60 and to the previously described ADNF-9 active peptide SALLRSIPA (SEQ ID NO:5). This ADNF III polypeptide is 8 amino acids in length and has the sequence NAPVSIPQ, i.e., Asn-Ala-Pro-Val-Ser-Ile-Pro-Gln (SEQ ID NO:6). Both the "expressed" (full length) ADNF III polypeptides and NAPVSIPQ-derived (SEQ ID NO:6) ADNF III polypeptides of the present invention are extraordinarily potent in preventing neuronal cell death. Such ADNF III polypeptides have been found to exhibit neuroprotection against neurotoxins associated with HIV infection, electrical blockage, excitotoxicity and Alzheimer's disease.

As such, in one embodiment, the present invention provides isolated nucleic acids encoding the ADNF III polypeptides of the present invention, the ADNF III polypeptides including, for example, those that specifically bind to antibodies generated against immunogens having an amino acid sequence selected from the group consisting of SEQ ID NO:1, SEQ ID NO:3, SEQ ID NO:55, SEQ ID NO:57, and SEQ ID NO:59, and conservatively modified variants thereof. The ADNF III nucleic acids of the present invention also include those encoding amino acid sequences selected from the group consisting of SEQ ID NO:1, SEQ ID NO:3, SEQ ID NO:55, SEQ ID NO:57, and SEQ ID NO:59, and conservatively modified variants thereof. Exemplar nucleic acids include those set forth in SEQ ID NO:2, SEQ ID NO:4, SEQ ID NO:54, SEQ ID NO:56, and SEQ ID NO:58. Other nucleic acids encoding the ADNF III polypeptides of the present invention include those with silent codon substitutions relative to SEQ ID NO:2, SEQ ID NO:4, SEQ ID NO:54, SEQ ID NO:56, SEQ ID NO:58, as well as conservatively modified variations thereof.

Isolated nucleic acids that specifically hybridize, under stringent conditions, to the exemplar nucleic acids, i.e., SEQ ID NO:2, SEQ ID NO:4, SEQ ID NO:54, SEQ ID NO:56, SEQ ID NO:58, are also provided. For example, a complementary nucleic acid to a sequence provided by SEQ ID NO:2, SEQ ID NO:4, SEQ ID NO:54, SEQ ID NO:56, or SEQ ID NO:58 specifically hybridizes to SEQ ID NO:2, SEQ ID NO:4, SEQ ID NO:54, SEQ ID NO:56, or SEQ ID NO:58, respectively. Similarly, nucleic acids that have substantial subsequence complementary to SEQ ID NO:2, SEQ ID NO:4, SEQ ID NO:54, SEQ ID NO:56, or SEQ ID NO:58 also specifically hybridize to SEQ ID NO:2, SEQ ID NO:4, SEQ ID NO:54, SEQ ID NO:56, or SEQ ID NO:58, respectively. Still other nucleic acids encoding the ADNF III polypeptides of the present invention include those that are amplified by primers that specifically hybridize under stringent hybridization conditions to the same sequence as a primer set selected from the group consisting of: sense 5' TCCAATGTTCACCTGCAG 3' (SEQ ID NO:7), sense 5' ACCTGCAGCAAAACAACTAT 3' (SEQ ID NO:9), and antisense 5' GCTCGTTACAGATTGTAC 3' (SEQ ID NO:8).

Isolated nucleic acids that specifically hybridize, under stringent conditions, to the exemplar promoter nucleic acids, i.e., SEQ ID NO:60, are also provided. For example, a complementary nucleic acid to a sequence provided by SEQ ID NO:60 specifically hybridizes to SEQ ID NO:60. Similarly, nucleic acids that have substantial subsequence complementary to SEQ ID NO:60 also specifically hybridize to SEQ ID NO:60.

In a presently preferred embodiment, the isolated nucleic acids of the present invention are optionally vector nucleic acids, which comprise a transcription cassette. More particularly, the vectors preferably include the above-described nucleic acids operably linked (under the control of) a promoter; either constitutive or inducible. The promoter may be heterologous or may be an ADNF III promoter. The vector can also include initiation and termination codons. The transcription cassette optionally encodes a polypeptide. Typically, the portion of the transcription cassette that encodes the polypeptide specifically hybridizes, under stringent conditions, to a nucleic acid selected from the group consisting of SEQ ID NO:2, SEQ ID NO:4, SEQ ID NO:54, SEQ ID NO:56, or SEQ ID NO:58. The promoter region may also hybridized under stringent conditions to a nucleic acid having the sequence of SEQ ID NO:60. Upon transduction of the transcription cassette into a cell, an mRNA is produced that specifically hybridizes, under stringent conditions, to a nucleic acid selected from the group consisting of SEQ ID NO:2, SEQ ID NO:4, SEQ ID NO:54, SEQ ID NO:56, or SEQ ID NO:58. The mRNA is translated in the cell into an ADNF III polypeptide, such as the ADNF III polypeptides comprising amino acid sequences selected from the group consisting of SEQ ID NO:1, SEQ ID NO:3, SEQ ID NO:55, SEQ ID NO:57, and SEQ ID NO:59, and conservatively modified variants thereof.

In another embodiment, the present invention provides ADNF III polypeptides. Such ADNF III polypeptides include those encoded by nucleic acids that specifically hybridize, under stringent conditions, to SEQ ID NO:2, SEQ ID NO:4, SEQ ID NO:54, SEQ ID NO:56, or SEQ ID NO:58. Such ADNF III polypeptides also include those that specifically bind an antibody generated against an immunogen having an amino acid sequence selected from the group consisting of SEQ ID NO:1, SEQ ID NO:3, SEQ ID NO:55, SEQ ID NO:57, and SEQ ID NO:59 and conservatively modified variations thereof. Exemplar ADNF III polypeptides include ADNF III polypeptides having the amino acid sequences selected from the group consisting of SEQ ID NO:1, SEQ ID NO:3, SEQ ID NO:55, SEQ ID NO:57, and SEQ ID NO:59 and conservatively modified variations thereof.

In yet another embodiment, the ADNF III polypeptides of the present invention comprise the following amino acid sequence:

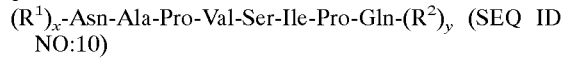
(SEQ ID NO:10)

and conservatively modified variations thereof. In the above formula, $R^1$ is an amino acid sequence comprising from 1 to about 40 amino acids, wherein each amino acid is independently selected from the group consisting of naturally occurring amino acids and amino acid analogs. The term "independently selected" is used herein to indicate that the amino acids making up the amino acid sequence $R^1$ may be identical or different (e.g., all of the amino acids in the amino acid sequence may be threonine, etc.). Moreover, as previously explained, the amino acids making up the amino acid sequence $R^1$ may be either naturally occurring amino acids, or known analogues of natural amino acids that functions in a manner similar to the naturally occurring amino acids (i.e., amino acid mimetics and analogs). Suitable amino acids that can be used to form the amino acid sequence $R^1$ include, but are not limited to, those listed in Table I, supra. The indexes "x" and "y" are independently selected and can be equal to one or zero.

As with $R^1$, $R^2$, in the above formula, is an amino acid sequence comprising from 1 to about 40 amino acids, wherein each amino acid is independently selected from the group consisting of naturally occurring amino acids and amino acid analogs. Moreover, as with $R^1$, the amino acids making up the amino acid sequence $R^2$ may be identical or different, and may be either naturally occurring amino acids, or known analogues of natural amino acids that functions in a manner similar to the naturally occurring amino acids (i.e., amino acid mimetics and analogs). Suitable amino acids that can be used to form $R^2$ include, but are not limited to, those listed in Table I, supra.

In a further embodiment, the present invention provides antibodies that specifically bind to ADNF III polypeptides. In a preferred embodiment, the antibodies specifically bind to an ADNF III polypeptide, the ADNF III polypeptide having an amino acid sequence selected from the group consisting of SEQ ID NO:1, SEQ ID NO:3, SEQ ID NO:55, SEQ ID NO:57, and SEQ ID NO:59 and conservatively modified variations thereof.

Quite surprisingly, it has been discovered that the ADNF III polypeptide of the present invention can be used for the treatment of neurological deficiencies and for the prevention of neuronal cell death. Such ADNF III polypeptides can be used, for example, to prevent the death of neuronal cells including, but not limited to, spinal cord neurons, hippocampal neurons, cerebral neurons and cholingeric neurons. More particularly, the ADNF III polypeptides of the present invention can be used to prevent cell death associated with (1) gp120, the envelope protein from HIV; (2) N-methyl-D-aspartic acid (excito-toxicity); (3) tetrodotoxin (blockage of electrical activity); and (4) β-amyloid peptide, a substance related to neuronal degeneration in Alzheimer's disease.

As such, the present invention provides methods for preventing neuronal cell death. More particularly, in one aspect, methods are provided for using the ADNF III polypeptides of the present invention to prevent gp120-induced neuronal cell death in a patient infected with HIV. In another aspect, methods are provided for using the ADNF III polypeptides of the present invention to prevent neuronal cell death associated with excito-toxicity induced by N-methyl-D-aspartate stimulation. In yet another aspect, methods are provided for using the ADNF III polypeptides of the present invention to prevent neuronal cell death induced by the β-amyloid peptide in a patient afflicted or impaired with Alzheimer's disease. In still another aspect, methods are provided for using the ADNF III polypeptides of the present invention to alleviate learning impairment produced by cholingeric blockage in a patient impaired or afflicted with Alzheimer's disease.

In addition to the foregoing, the ADNF III polypeptides of the prevent invention can effectively be used to prevent neuronal cell death associated with a number of other neurological diseases and deficiencies. More particularly, as a result of their ability to inhibit neuronal cell death associated with N-methyl-D-aspartic acid (excitotoxicity), the ADNF III polypeptides of the present invention can be used to treat numerous forms of neurodegeneration (see Lipton & Rosenberg, New Eng. J. Med. 330:613–622 (1994), the teaching of which are incorporated herein by reference for all purposes). Such neurodegeneration includes, but is not limited to, the following: Huntington's disease; AIDS dementia complex; epilepsy, neuropathic pain syndromes; olivopontocerebellar atrophy; parkinsonism and Parkinson's disease; amyotrophic lateral sclerosis; mitochondrial abnormalities and other inherited or acquired biochemical disorders; MELAS syndrome; MERRF; Leber's disease; Wernicke's encephalopathy; Rett syndrome; homocysteinuria; hyperprolinemia; nonketotic hyperglycinemia; hydroxybutyric aminoaciduria; sulfite oxide deficiency; combined systems disease; lead encephalopathy; Alzheimer's disease; hepatic encephalopathy; Tourette's syndrome; oxidative stress induced neuronal death; Down's syndrome; developmental retardation and learning impairments; closed head trauma; dompamine toxicity; drug addiction, tolerance, and dependency. Those of skill in the art will appreciate that the above list is illustrative and not exhaustive, and that the ADNF III polyepeptides of the present invention can be used to treat other neurological disorders.

Other features, objects and advantages of the invention and its preferred embodiments will become apparent from the detailed description that follows.

BRIEF DESCRIPTION OF THE DRAWINGS

FIG. 1 illustrates a nucleic acid (SEQ ID NO:4) and amino acid (SEQ ID NO:3) sequence for mouse ADNF III.

The nucleic acid sequence contains 2418 base pairs of open reading frame. The ADNF III polypeptide consists of 806 amino acids with a calculated molecular weight of about 90 kDa and a pI of about 5.85. FIG. 1 also illustrates the homologies to hsp60 (single underline) and PIF1 (dotted underline), glycosylation sites (double underline) as well as the motif flutaredoxin active site motif and the zinc finger motif present in ADNF III (bold and italic).

FIG. 4A illustrates the western blot hybridization for immunological detection of the cloned ADNF III protein from bacterial extracts. Bacterial extracts expressing clone p25 were subjected to 10% SDS-polyacrylamide gel electrophoresis followed by western blot analysis with the antibodies used for cloning. Anti-SALLRSIPA (SEQ ID NO:5)=α1, diluted at 1:250 and detected with Amersham's Life Science ECL+Plus kit); pBS=bacterial extract of a control culture transformed with the phagemid pBluescript SK; p25=bacterial extract of a culture transformed with the phagemid pBluescript SK containing the clone 25 insert; ε1=p25, a fusion protein containing partial sequences of the β-galactosidase, was enriched (15-fold) on an affinity column. CBB=Coomassie Brilliant Blue (protein) staining of the same lanes that were subjected western blot analysis. The dot blot exhibited shows that the antibody (α1) recognized antigens SALLRISIPA (SEQ ID NO:5) and NAPV-SIPQ (SEQ ID NO:6) (1=SALLRSIPA, NAP=NAPVSIPQ), but did not recognize a control peptide LGGGS (SEQ ID NO:11). As illustrated in FIG. 4A, a protein of high molecular weight (approximately 90 kDa, lane p25) was identified as the ADNF III molecule. FIG. 4B illustrates immunological identification of a secreted ADNF III protein in astrocyte conditioned medium. Astrocyte-conditioned medium was prepared as described supra (see Brenneman & Gozes, J. Clin. Invest. 97:2299–2237 (1996)), with a protein of a high molecular weight identified as the ADNF III molecule by western blot hybridization. SDS-polyacrylamide gel electrophoresis was performed as indicated in the above cited paper. Astroglial cultures obtained from newborn rat cerebral cortex were utilized. Cell extracts and conditioned medium from astrocytes that were treated or untreated with VIP (+, −) were subjected to electrophoresis through 10% polyacrylamide slab gel containing 0.1% SDS. Western blot analysis was performed with antibodies utilized for the cloning (anti-SALLRSIPA (SEQ ID NO:5)=α1). The first lane exhibits intracellular proteins identified by the antibody. Specificity was determined by incubation of the antibodies with the blot in the presence of the enriched cloned protein (ε1) that resulted in disappearance of the antibody binding. Further specificity was determined in that the antibody did not react against hsp60 (StressGen Biotechnologies Corp, Victoria, Canada). α2 is a specific antibody raised against the 89 KD ADNF III-like secreted protein extracted from the polyacrylamide gel. α3 is a specific antibody raised against the lower (~60 kDa) ADNF III-like protein extracted from the polyacrylamide gel.

FIGS. 5A–C. FIG. 5 illustrates PCR of human ADNF III cDNA from human neuroblastoma (Lilling et al., J. Molec. Neurosci. 5:231–239 (1995)). The correct expected size of the product (similar to that expected in mice) is shown (see FIG. 5B; sense=SEQ ID NO:29; antisense=SEQ ID NO:30)). Human material expresses the ADNF III mRNA and sequence analysis, as compared to the mouse sequence, revealed 86% similarity at the nucleotide level and 93% similarity and 92% identity at the amino acid level (see FIG. 5C; SEQ ID NO:31, upper, SEQ ID NO:32, lower)).

FIG. 6A illustrates neuroprotection against electrical blockade with a neurotoxin (closed circles) and against β-amyloid associated neurotoxicity (open circles) in cerebral cortical cultures (the experiments were performed as described by Gozes et al., Proc. Natl. Acad. Sci. USA 93:427–432 (1996). Bacterial extract containing the phagemid without an insert is inactive (closed squares). For β-amyloid treatment, the fragment 25–35 was synthesized as before (Gozes et al., Proc. Natl. Acad. Sci. USA 93:427–432 (1996)) and added to the cultures at a concentration of 25 μM. FIG. 6B illustrates that in a repeat of the experiment described above in FIG. 6A, the activity of ADNF III was mimicked by an 8 amino acid peptide (NAP). Closed circles are protection against tetrodotoxin; open circles, against β-amyloid; and closed squares, a control, inactive peptide (SVRLGLGGNAPVSIPQQS, (SEQ ID NO:12)). FIG. 6C illustrates examples of neuroprotection by NAP against 1 pM gp120 (RFII isolate) (Brenneman et al., Nature 335:639–642 (1988); Brenneman & Gozes, J. Clin. Invest. 97:2299–2307 (1996)); NMDA (10 μM); and naturally occurring cell death. Experiments utilizing cerebral cortical cultures derived from newborn rats were performed as previously described. For electrical blockade, incubation with 1 μM tetrodotoxin was performed (Brenneman & Eiden, Proc. Natl. Acad. Sci. USA 83:1159–1162 (1986)). For β-amyloid treatment, the fragment 25–35 was synthesized as before (Gozes et al., Proc. Natl. Acad. Sci. USA 93:427–432 (1996)) and added to the cultures at a concentration of 25 μM. Toxins were added to nine-day old cultures and incubated for an additional five days. The expressed ADNF III protein extract was added together with the toxin at indicated dilutions. Experiments were repeated at least three times. The number of neurons plated=300,000/plate; the number that survive the dissociation and plating procedure is about 88%; and the number that survive at the termination of the experiment is 75% (without any additional toxins). With additional toxins, the number of surviving neurons would be about 50%. Significant neuroprotection by ADNF III (denoted clone 25) was obtained at dilutions of $10^{-15}$–$10^{-13}$ (of a 1 mg/ml protein solution diluted in PBS) against tetrodotoxin, and at dilutions >$10^{-15}$ against β-amyloid (P<0.001). Significant neuroprotection by NAP against tetrodotoxin was at concentrations of $10^{-18}$–$10^{-14}$ M, against β-amyloid at $10^{-16}$ and $10^{-15}$ M, against NMDA at >$10^{-16}$ M and against gp120 at $10^{-15}$–$10^{-10}$ M (P<0.01).

FIG. 9 illustrates northern blot identification of ADNF III mRNA. RNA was extracted from the brains of 28-day-old apolipoprotein E-deficient mice (E) treated with saline for the first two weeks of life or with NAP (E+N), control mice (C) were treated with saline. RNA was subjected to northern blot hybridization with a PCR-labeled ADNF III specific probe ($\alpha$-$^{32}$P-dCTP, Amersham, 3000 Ci/mmol) (see FIG. 2) in comparison to an actin-specific probe (Gozes et al., *Mol. Brain Res.* 2:137–148 (1987)).

FIG. 11. illustrates a nucleic acid (SEQ ID NO:54) and amino acid (SEQ ID NO:55) sequence for mouse ADNF III. To precisely map the initiation codon, the mouse gene was also cloned in a BAC system (Genome Systems, Inc., St. Louis, Mo.) and the initiation codon AUG was chosen as the first one appearing 640 bases downstream of a termination codon in the gene sequence. The initiator AUG was the first one containing the consensus initiation codon including a G immediately following the AUG codon and a G three bases before.

FIG. 12 illustrates a nucleic acid (SEQ ID NO:56) and amino acid (SEQ ID NO:57) sequence of H3 human ADNF III clone.

FIG. 13 illustrates a nucleic acid (SEQ ID NO:58) and amino acid (SEQ ID NO:59) sequence of H7 human ADNF III clone.

FIG. 14 illustrates a nucleic acid sequence of a mouse ADNF III promoter (SEQ ID NO:60). A putative TATA box is underlined.

FIG. 18 illustrates a polymorphic region in the ADNF III nucleic acid sequence (SEQ ID NOS:61–63) (see also FIG. 13., polymorphic site).

DEFINITIONS

Figure 2:
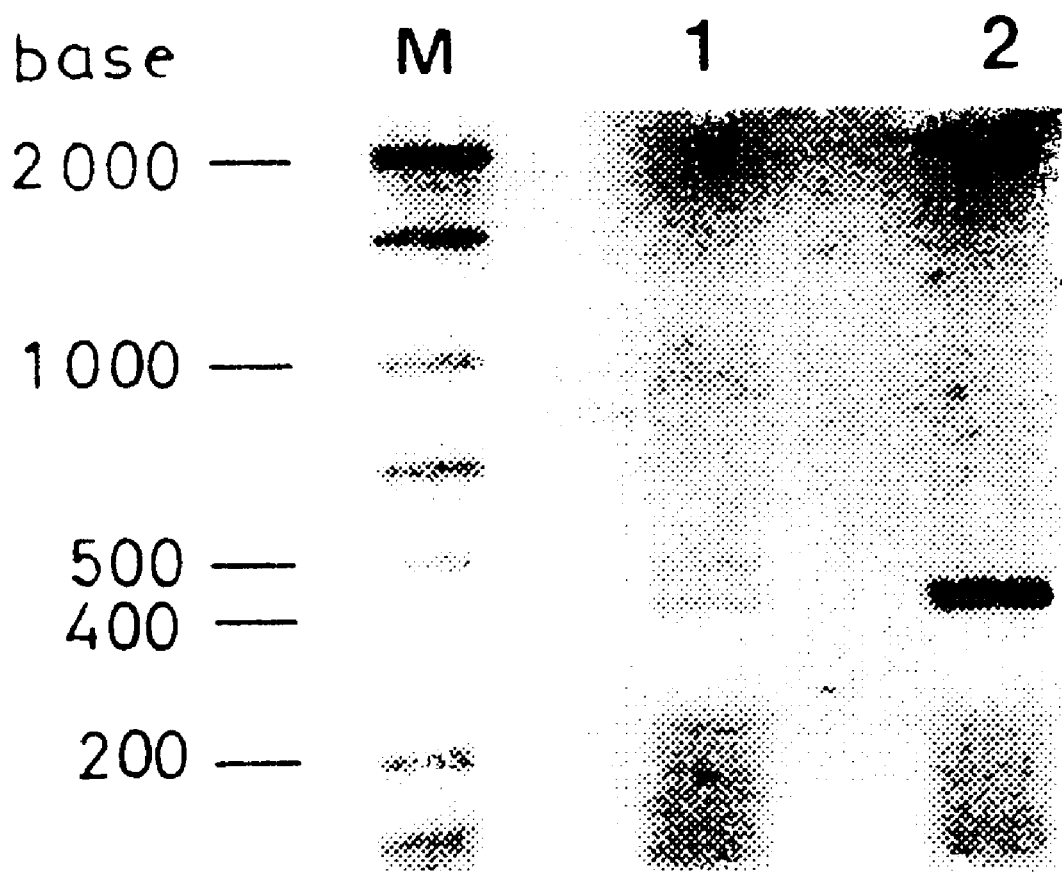
FIG. 2 illustrates the results of using the polymerase chain reaction (PCR) to identify ADNF III mRNA in rat astrocytes. The ADNF III PCR product is enriched in astrocytes as compared to fibroblasts. The size of the full length RNA transcript in northern blot hybridization was about 5300±200 base-pairs, suggesting a long poly (A) tail (not shown). The mRNA was identified in astrocytes as well as in the brain cortex, cerebellum and the hind brain. Low amounts were detectable in the kidney, spleen and lung.

The terms "ADNF III" or "ADNP" refer to nucleic acids encoding polypeptides that are polymorphic variants, interspecies homologues (preferably mammalian homologues) and alleles of ADNF III that: (1) bind to antibodies raised against an immunogen comprising an amino acid sequence selected from the group consisting of SEQ ID NO:1, SEQ ID NO:3, SEQ ID NO:55, SEQ ID NO:57, and SEQ ID NO:59 and conservatively modified variants thereof; or (2) specifically hybridize under stringent hybridization conditions to a sequence selected from the group consisting of SEQ ID NO:2, SEQ ID NO:4, SEQ ID NO:54, SEQ ID NO:56, or SEQ ID NO:58 and conservatively modified variants thereof; or (3) are amplified by primers that specifically hybridize under stringent hybridization conditions to the same sequence as a primer set comprising primers selected from the group consisting of SEQ ID NO:7, SEQ ID NO:8, and SEQ ID NO:9; or (4) have substantial sequence (i.e., at least about 60%) or subsequence identity/complementarity to a sequence selected from the group consisting of SEQ ID NOS:1–4, 54–60 and conservatively modified variants thereof.

The term "biologically active" refers to a peptide sequence that will interact with naturally occurring biological molecules to either activate or inhibit the function of those molecules in vitro or in vivo. The term "biologically active" is most commonly used herein to refer to ADNF III polypeptides such as "NAP" (NAPVSIPQ; SEQ ID NO:6) that exhibit neuroprotective/neurotrophic action on neurons originating in the central nervous system both in vitro or in vivo. Thus, the present invention provides polypeptide subsequences that have the same or similar activity as ADNF III or NAP when tested as compared to ADNF III using, e.g., cerebral cortical cultures treated with a neurotoxin (see Gozes et al., *Proc. Nat'l. Acad. Sci. USA* 93:427–432 (1996)).

"An amount sufficient" or "an effective amount" is that amount of a given ADNF III polypeptide that exhibits the neuroprotective/neurotrophic activity of interest or, which provides either a subjective relief of a symptom(s) or an objectively identifiable improvement as noted by the clinician or other qualified observer. The dosing range varies with the ADNF III polypeptide used, the route of administration and the potency of the particular ADNF III polypeptide (see, e.g., U.S. Ser. No. 08/324,297, filed Oct. 17, 1994, herein incorporated by reference in its entirety, and examples described herein).

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)).

Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:

1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (1), Leucine (L), Valine (V); and
8) Phenylalanine (F), Tyrosine (Y), Tryptophan (W). (see, e.g., Creighton, Proteins (1984)).

The terms "isolated," "purified" or "biologically pure" refer to material that is substantially or essentially free from components that normally accompany it as found in its native state.

The term "subsequence" in the context of a particular nucleic acid sequence refers to a region of the nucleic acid equal to or smaller than the specified nucleic acid.

Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. An overview to the hybridization of nucleic acids is found in Tijssen, *Laboratory Techniques in Biochemistry and Molecular Biology—Hybridization with Nucleic Acid Probes*, "Overview of principles of hybridization and the strategy of nucleic acid probe assays" (1993).

The term "nucleic acid probe" refers to a molecule that binds to a specific sequence or subsequence of a nucleic acid. A probe is preferably a nucleic acid that binds through complementary base pairing to the full sequence or to a subsequence of a target nucleic acid. It will be understood by one of skill in the art that probes may bind target sequences lacking complete complementarity with the probe sequence depending upon the stringency of the hybridization conditions. The probes are preferably directly labelled as with isotopes, chromophores, lumiphores, chromogens, or indirectly labelled such as with biotin to which a streptavidin complex may later bind. By assaying for the presence or absence of the probe, one can detect the presence or absence of the select sequence or subsequence.

A "label" is a composition detectable by spectroscopic, photochemical, biochemical, immunochemical or chemical means. For instance, useful labels include, but are not limited to, the following: $^{32}P$, fluorescent dyes, electron-dense reagents, enzymes (e.g., as commonly used in an ELISA), biotin, dioxigenin, or haptens and proteins for which antisera or monoclonal antibodies are available.

A "labeled nucleic acid probe" is a nucleic acid probe that is bound, either covalently, through a linker, or through electrostatic, van der Waals or hydrogen bonds to a label such that the presence of the probe may be detected by detecting the presence of the label bound to the probe.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or a library DNA or RNA).

The phrase "stringent hybridization conditions" refers to conditions under which a probe will hybridize to its target subsequence, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary highly stringent hybridization conditions include hybridization in a buffer comprising 50% formamide, 5×SSC, and 1% SDS at 42° C., or hybridization in a buffer comprising 5×SSC, 1% SDS at 65° C., both with a wash of 0.2×SSC and 0.1% SDS at 65° C. Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. This definition also refers to the complement of a test sequence, which has a designated percent sequence or subsequence complementarity when the test sequence has a designated or substantial identity to a reference sequence. For example, a designated amino acid percent identity of 60% refers to sequences or subsequences that have at least about 60% amino acid identity when aligned for maximum correspondence over a comparison window as measured using one of the following sequence comparison algorithms or by manual alignment and visual inspection. Such sequences are then said to have "substantial identity." Preferably, the percent identity exists over a region of the sequence that is at least about 25–50 amino acids in length, more preferably over a region that is 100 amino acids in length. Preferably the percent identity is about 60%, more preferably 70–80%, more preferably about 90%.

When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identity for the test sequence(s) relative to the reference sequence, based on the designated or default program parameters.

A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g, version 7.0 (Devereaux et al., *Nuc. Acids Res.* 12:387–395 (1984).

Another example of algorithm that is suitable for determining percent sequence identity (i.e., substantial similarity or identity) is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical, analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described above.

The term "antibody" refers to a polypeptide substantially encoded by an immunoglobulin gene or immunoglobulin genes, or fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon which, in turn, define the immunoglobulin classes, IgG, IgM, IgA, IgD and IgE, respectively.

An exemplar immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, for example, as intact immunoglobulins or as a number of well characterized fragments produced by digestion with various peptidases. Thus, for example, pepsin digests an antibody below the disulfide linkages in the hinge region to produce F(ab)'$_2$, a dimer of Fab that itself is a light chain joined to $V_H$-$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see *Fundamental Immunology* (Paul, ed., 3d ed. 1993), which is incorporated herein by reference, for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule that confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that utilizes an antibody to specifically bind an analyte. The immunoassay is characterized by the use of specific binding properties of a particular antibody to isolate, target, and/or quantify the analyte.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies raised to ADNF III with the amino acid sequence of SEQ ID NO:1, 3, 55, 57, or 59 can be selected to obtain only those antibodies that are specifically immunoreactive those polypeptides and not with other proteins, except for polymorphic variants, alleles and interspecies homologues of ADNF III. This selection may be achieved by subtracting out antibodies that cross react with molecules such as ADNF I. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

An "anti-ADNF III" antibody is an antibody or antibody fragment that specifically binds a polypeptide encoded by the ADNF III nucleic acid described herein.

An "expression vector" includes a recombinant expression cassette that includes a nucleic acid that encodes a polypeptide that can be transcribed and translated by a cell. A "recombinant expression cassette" is a nucleic acid construct, generated recombinantly or synthetically, with a series of specified nucleic acid elements that permit transcription of a particular nucleic acid in a target cell. The expression vector can be part of a plasmid, virus or nucleic acid fragment. Typically, the recombinant expression cassette portion of the expression vector includes a nucleic acid to be transcribed and a promoter. In some embodiments, the expression cassette additionally includes, for example, an origin of replication and/or chromosome integration elements. A "promoter" is an array of nucleic acid control sequences that direct transcription of a nucleic acid. As used herein, a promoter includes necessary nucleic acid sequences near the start site of transcription, such as, in the case of a polymerase II type promoter, a TATA element. The promoter also includes distal enhancer or repressor elements that can be located as much as several thousand base pairs from the start site of transcription. A "constitutive" promoter is a promoter that is active under most environmental conditions and states of development or cell differentiation. An "inducible" promoter responds to an extracellular stimulus. The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" when used in reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means, for example under the control of a heterologous promoter.

An "immunogenic composition" is a composition that elicits the production of an antibody that binds a component of the composition when administered to a mammal, or that elicits the production of a cell-mediated immune response against a component of the composition.

An "antigenic epitope" in the context of a polypeptide is a polypeptide subsequence that, when presented as an immunogen, or as a portion of an immunogen (e.g., with a carrier protein or adjuvant, or on the surface of a viral vector), elicits an antibody that specifically binds to the full length polypeptide.

The term "contacting" is used herein interchangeably with the following: combined with, added to, mixed with, passed over, incubated with, flowed over, etc.

Moreover, the ADNF III polypeptides of the present invention can be "administered" by any conventional method such as, for example, parenteral, oral, topical, and inhalation routes. In presently preferred embodiments, parenteral and nasal inhalation routes are employed.

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes. The amino acids referred to herein are described by shorthand designations as follows:

TABLE I

Amino Acid Nomenclature

| Name | 3-letter | 1 letter |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |

TABLE I-continued

Amino Acid Nomenclature

| Name | 3-letter | 1 letter |
|---|---|---|
| Tryptophan | Trp | W |
| Tyrosine | Tyr | Y |
| Valine | Val | V |

DETAILED DESCRIPTION OF THE INVENTION AND PREFERRED EMBODIMENTS

The present invention relates to the discovery of a nucleic acid encoding a novel neuroprotective polypeptide, i.e., Activity Dependent Neurotrophic Factor III (ADNF III), also known as Activity Dependent Neuroprotective Protein (ADNP). Based on the recognized homology between ADNF I and hsp60, a heat shock protein, and PIF1, a DNA repair protein, these two epitopes were utilized to prepare antibodies that, in turn, were used to screen a mouse cDNA-expression library to identify the new neuroprotective polypeptide ADNF III. The mouse cDNA consists of about 2418 base pairs of an open reading frame, which encodes an ADNF III polypeptide of about 806 amino acids, pI 5.85. A eight amino acid sequence of ADNF III (ADNF III-8 polypeptide) exhibits structural similarity to the active site of ADNF I (the heat shock protein 60 homologue), with 77.8% identity at the DNA level in comparison to heat shock protein 60 encoding sequences. In addition, two amino acid sequences along the cDNA structure, one of five amino acids and another of nine amino acids, exhibits 72% and 77.8% identity with PIF1 encoding sequences, respectively. Further comparative sequence analysis revealed the signature of ABC transporters family: ATP binding proteins involved in active transport of small hydrophilic molecules across the cytoplasmic membrane; a GTP/ATP binding site; and an aldehyde dehydrogenase active site. cDNAs encoding human ADNF III have also been cloned and are provided by the present invention. The promoter for mouse ADNF III has also been cloned. Thus, the present invention provides ADNF III, interspecies homologues (preferably mammalian homologues), polymorphic variants and alleles, as well as polypeptide subsequences that have the same or similar activity as ADNF III when tested as compared to ADNF III using, e.g., cerebral cortical cultures treated with a neurotoxin (see Gozes et al., Proc. Nat'l. Acad. Sci. USA 93:427–432 (1996)).

The chromosomal location of ADNF III has been identified using Stanford Human Genome Database, RH server. The ADNF III gene was mapped to 20q13.2 with identity to the ordered marker G30243 and linkage to GBD locus D20S831. This region of chromosome 20 is also linked to autosomal dominant nocturnal frontal-lobe epilepsy (ADNFLE), which has also been mapped to 20q13.2 (see, e.g., Phillips et al., Am J. Hum Genet. 63:1101–1109 (1998); Steinlein et al., Nat. Genet. 11:201–203 (1995); Phillips et al., Nat. Genet. 10:4–6 (1996); Magenis et al., Mamm. Genome 5:503–508 (1994)). As shown in FIGS. 13 and 18, ADNF III also has a polymorphic region that may be used to identify disease-linked ADNF III alleles, i.e., using oligonucleotide probes and primers that discriminate between the polymorphisms.

Figure 15:
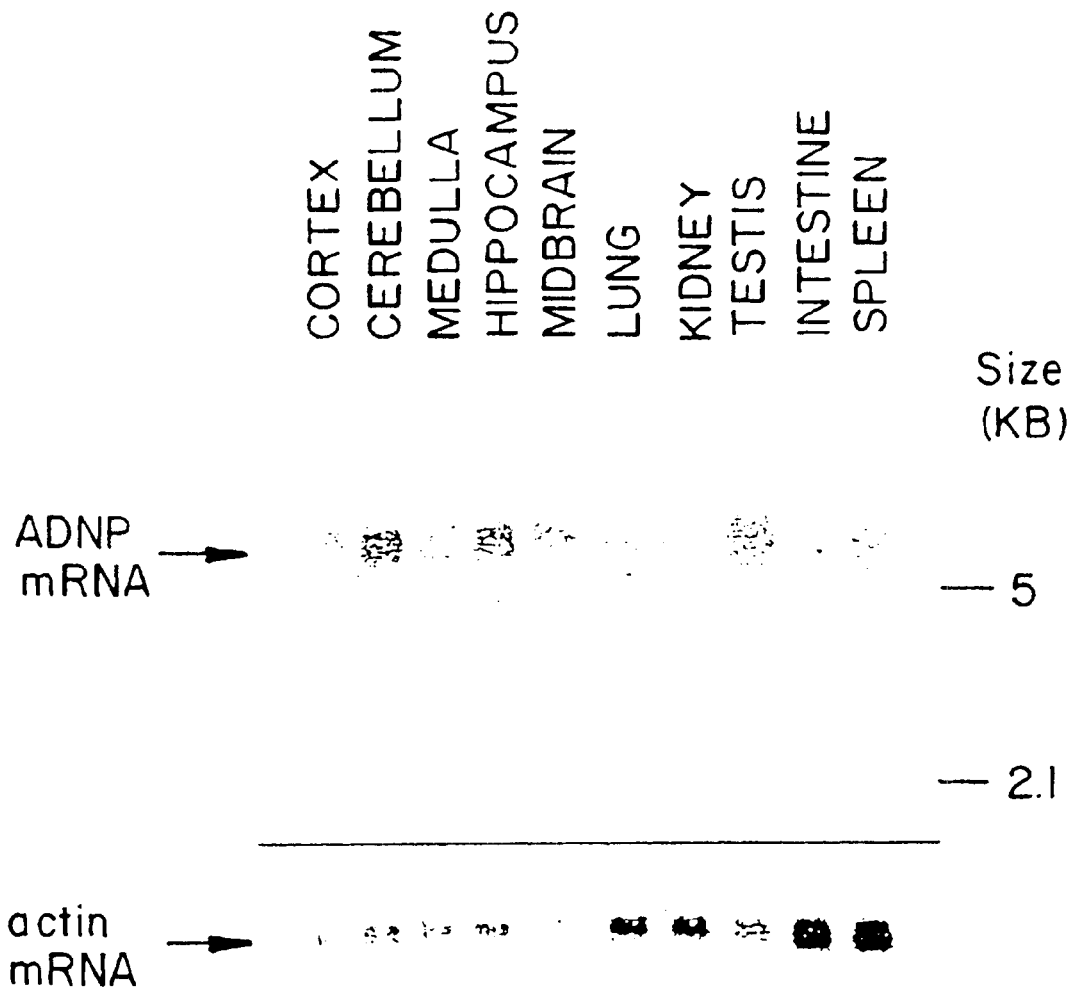
FIG. 15 illustrates northern blot identification of ADNF III mRNA. RNA was extracted from various tissues and brain sections of 18-day-old inbred C57B6 mice. RNA was subjected to northern blot hybridization with a PCR labeled ADNF III specific probe in comparison to an active specific probe (see Gozes et al., *Mol. Brain Res.* 2:137–148 (1987)).

Using RT-PCR technology, mRNA encoding ADNF III was initially identified in rat astrocytes derived from the cerebral cortex. The size of the full length RNA transcript in northern blot hybridization was about 5300±200 base-pairs, suggesting a long poly (A) tail. Moreover, PCR-assisted mRNA determination indicated that the mRNA encoding ADNF III was expressed in astrocytes, but not in fibroblasts. In addition to being expressed in astrocytes, the mRNA was identified in the brain, including cortex, cerebellum, hippocampus, frontal lobe, medulla oblongata, subthalamic nucleoic, spinal cord, and hind brain (see, e.g., FIG. 15). ADNF III mRNA is also expressed in fetal tissues, especially the lung, and in endocrine tissues. Low amounts of mRNA were detectable in the kidney, spleen, intestine, and lung. PCR of cDNA from human neuroblastoma indicated that human material expresses ADNF III mRNA. A human ADNF III cDNA was cloned, and sequence analysis revealed about 87% similarity at the nucleotide level and 93% similarity and 92% identity at the amino acid level with the mouse ADNF III nucleic acid. Western blot hybridization further indicated that ADNF III-like immunoreactivity (approximately 90 kDa) is secreted from astroglial cells incubated with VIP.

Based on the homology between ADNF I and hsp60 to ADNF III, an ADNF III polypeptide was synthesized that exhibited structural homology to hsp60 and to the previously described active peptide SALLRSIPA (SEQ ID NO:5). This ADNF III polypeptide is 8 amino acids in length and has the sequence NAPVSIPQ (SEQ ID NO:6) (referred to as NAP or ADNF III-8). Once synthesized, the ADNF III polypeptide, i.e., NAPVSIPQ (SEQ ID NO:6), and the "expressed protein" were screened for their ability to prevent neuronal cell death. In doing so, it was found that the "expressed protein" (full length ADNF III expressed from clone 25) prevents neuronal cell death associated the β-amyloid peptide in cerebral cortical cultures (the experiments were performed as described by Gozes et al., Proc. Natl. Acad. Sci. USA 93:427–432 (1996)). In addition, it was found that the ADNF III polypeptide, i.e., NAPVSIPQ (SEQ ID NO:6), prevents neuronal cell death associated with the β-amyloid peptide in cerebral cortical cultures.

Moreover, it was found that the "expressed protein" from the cloned material prevents neuronal cell death associated with electrical blockade (1 μM tetrodotoxin) in cerebral cortical cultures (experiments were performed as described in Brenneman & Gozes, J. Clin. Invest., 97:2299–2237 (1996)). Similarly, the identified ADNF III-8 polypeptide, i.e., NAPVSIPQ (SEQ ID NO:6), prevents neuronal cell death associated with electrical blockade in cerebral cortical cultures. In addition, the ADNF III-8 polypeptide also provides protection against learning and memory deficiencies associated with cholinergic blockade.

In view of the foregoing, the present invention provides, inter alia, nucleic acid sequences encoding ADNF III polypeptides; ADNF III polypeptides encoded by such nucleic acid sequences; antibodies to ADNF III polypeptides; and methods of using such ADNF III polypeptides for the treatment of neurological deficiencies and for the prevention of cell death associated with (1) gp120, the envelope protein from HIV; (2) N-methyl-D-aspartic acid (excitotoxicity); (3) tetrodotoxin (blockage of electrical activity); and (4) β-amyloid peptide, a substance related to neuronal degeneration in Alzheimer's disease.

In addition, as a result of their ability to inhibit neuronal cell death associated with N-methyl-D-aspartic acid (excitotoxicity), the ADNF III polypeptides of the present invention can be used to treat numerous forms of neurodegeneration (see Lipton & Rosenberg, New Eng. J. Med. 330:613–622 (1994), the teaching of which are incorporated herein by reference for all purposes). Such neurodegeneration includes, but is not limited to, the following: Huntington's disease; AIDS dementia complex; epilepsy; neuropathic pain syndromes; olivopontocerebellar atrophy; parkinsonism and Parkinson's disease; amyotrophic lateral sclerosis; mitochondrial abnormalities and other inherited or acquired biochemical disorders; MELAS syndrome; MERRF; Leber's disease; Wernicke's encephalopathy; Rett syndrome; homocysteinuria; hyperprolinemia; nonketotic hyperglycinemia; hydroxybutyric aminoaciduria; sulfite oxide deficiency; combined systems disease; lead encephalopathy; Alzheimer's disease; hepatic encephalopathy; Tourette's syndrome; oxidative stress induced neuronal death; Down's syndrome; developmental retardation and learning impairments; closed head trauma; dompamine toxicity; drug addiction, tolerance, and dependency. Those of skill in the art will appreciate that the above list is merely illustrative and that the ADNF III polypeptides of the present invention can be used to treat other neurological disorders.

A. Cloning Methods for the Isolation of Nucleic Acid Sequences Encoding ADNF III Polypeptides Several specific nucleic acids encoding ADNF III polypeptides are described herein. These nucleic acids can be made using standard recombinant or synthetic techniques. Given the nucleic acids of the present invention, one of skill can construct a variety of clones containing functionally equivalent nucleic acids, such as nucleic acids that encode the same polypeptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Sambrook et al., *Molecular Cloning—A Laboratory Manual* (2nd ed. 1989) and *Current Protocols in Molecular Biology* (Ausubel et al., eds., 1994).

In addition, product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

The nucleic acid compositions of this invention, whether RNA, cDNA, genomic DNA or a hybrid of the various combinations, are isolated from biological sources or synthesized in vitro. The nucleic acids of the invention are present in transformed or transfected cells, in transformed or transfected cell lysates, or in a partially purified or substantially pure form.

In vitro amplification techniques suitable for amplifying sequences for use as molecular probes or generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification and other RNA polymerase mediated techniques (e.g., NASBA), are found in Berger, Sambrook et al. and Ausubel et al., all supra, as well as in U.S. Pat. No. 4,683,202; *PCR Protocols A Guide to Methods and Applications* (Innis et al., eds., 1990); Arnheim & Levinson (October 1, 1990) *C&EN* 36–47; *The Journal Of NIH Research* 3:81–94 (1991); Kwoh et al., *Proc. Natl. Acad. Sci. USA* 86:1173 (1989); Guatelli et al., *Proc. Natl. Acad. Sci. USA* 87:1874 (1990); Lomell et al.,*J. Clin. Chem* 35:1826 (1989); Landegren et al., *Science* 241:1077–1080 (1988); Van Brunt, *Biotechnology* 8:291–294 (1990); Wu & Wallace, *Gene* 4:560 (1989); Barringer et al., *Gene* 89:117 (1990); and Sooknanan & Malek, *Biotechnology* 13:563–564 (1995). Improved methods of cloning in vitro amplified nucleic acids are described in U.S. Pat. No. 5,426,039. Improved methods of amplifying large nucleic acids are summarized in Cheng et al., *Nature* 369:684–685 (1994) and the references therein. One of skill will appreciate that essentially any RNA can be converted into a double stranded DNA suitable for restriction digestion, PCR expansion and sequencing using reverse transcriptase and a polymerase.

Oligonucleotides for use as probes, for example, with in vitro ADNF III nucleic acid amplification methods, or for use as nucleic acid probes to detect ADNF III nucleic acids, are typically synthesized chemically according to the solid phase phosphoramidite triester method described by Beaucage & Caruthers, *Tetrahedron Letts.*, 22(20):1859–1862 (1981), e.g., using an automated synthesizer, e.g., as described in Needham-VanDevanter et al., *Nucleic Acids Res.* 12:6159–6168 (1984). Oligonucleotides can also be custom made and ordered from a variety of commercial sources known to those of skill in the art. Purification of oligonucleotides, where necessary, is typically performed by either native acrylamide gel electrophoresis, or by anion-exchange HPLC as described in Pearson & Regnier, *J. Chrom.* 255:137–149 (1983). The sequence of the synthetic oligonucleotides can be verified using the chemical degradation method of Maxam & Gilbert, in *Methods in Enzymology* 65:499–560 (Grossman & Moldave, eds., 1980).

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see Giliman & Smith, *Gene* 8:81–97 (1979); Roberts et al., *Nature* 328:731–734 (1987); and Sambrook et al., *Molecular Cloning—A Laboratory Manual* (2nd ed. 1989)).

B. Expression/Synthesis of ADNF III Polypeptides

In one embodiment, the polypeptides, or subsequences thereof, are synthesized using recombinant DNA methodology. Generally, this involves creating a nucleic acid sequence that encodes the protein, placing the nucleic acid in an expression cassette under the control of a particular promoter, expressing the protein in a host cell, isolating the expressed protein and, if required, renaturing the protein.

Once a nucleic acid encoding a polypeptide of the invention is isolated and cloned, the nucleic acid is optionally expressed in recombinantly engineered cells known to those of skill in the art. Examples of such cells include, but are not limited to, bacteria, yeast, plant, filamentous fungi, insect (especially employing baculoviral vectors) and mammalian cells. The recombinant nucleic acids are operably linked to appropriate control sequences for expression in the selected host. For *E. coli*, example control sequences include the T7, trp, or lambda promoters, a ribosome binding site and, preferably, a transcription termination signal. For eukaryotic cells, the control sequences typically include a promoter and, preferably, an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods. Such methods include, for example, the calcium chloride transformation method for *E. coli* and the calcium phosphate treatment or electroporation methods for mammalian cells. Cells transformed by the plasmids can be selected by resistance to antibiotics conferred by genes contained on the plasmids, such as the amp, gpt, neo, and hyg genes.

Once expressed, the recombinant polypeptides can be purified according to standard procedures of the art, including ammonium sulfate precipitation, affinity columns, column chromatography, gel electrophoresis and the like (see, e.g., Scopes, *Polypeptide Purification* (1982); Deutscher, *Methods in Enzymology Vol. 182: Guide to Polypeptide Purification* (1990)). Once purified, partially or to homogeneity as desired, the ADNF III polypeptides may then be used, e.g., to prevent neuronal cell death or as immunogens for antibody production.

In addition to the foregoing recombinant techniques, the polypeptides of the invention are optionally synthetically prepared via a wide variety of well-known techniques. Polypeptides of relatively short size are typically synthesized in solution or on a solid support in accordance with conventional techniques (see, e.g., Merrifield, *Am. Chem. Soc.* 85:2149–2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany & Merrifield, *Solid-Phase Peptide Synthesis*; pp. 3–284 in *The Peptides: Analysis, Synthesis, Biology. Vol. 2: Special Methods in Peptide Synthesis, Part A*.; Merrifield et al., *J. Am. Chem. Soc.* 85:2149–2156 (1963); and Stewart et al., *Solid Phase Peptide Synthesis* (2nd ed. 1984).

After chemical synthesis, biological expression or purification, the polypeptide(s) may possess a conformation substantially different than the native conformations of the constituent polypeptides. In this case, it is helpful to denature and reduce the polypeptide and then to cause the polypeptide to re-fold into the preferred conformation. Methods of reducing and denaturing polypeptides and inducing re-folding are well known to those of skill in the art (see Debinski et al., *J. Biol. Chem.* 268:14065–14070 (1993); Kreitman & Pastan, *Bioconjug. Chem.* 4:581–585 (1993); and Buchner et al., *Anal. Biochem.* 205:263–270 (1992)). Debinski et al., for example, describe the denaturation and reduction of inclusion body polypeptides in guanidine-DTE. The polypeptide is then refolded in a redox buffer containing oxidized glutathione and L-arginine.

One of skill will recognize that modifications can be made to the polypeptides without diminishing their biological activity. Some modifications may be made to facilitate the cloning, expression, or incorporation of the targeting molecule into a fusion polypeptide. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

C. Conservative Modifications of the ADNF III Nucleic Acids and Polypeptides One of skill will appreciate that many conservative variations of the nucleic acid and polypeptide sequences provided herein yield functionally identical products. For example, due to the degeneracy of the genetic code, "silent substitutions" (i.e., substitutions of a nucleic acid sequence that do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties (see the definitions section, supra), are also readily identified as being highly similar to a disclosed amino acid sequence, or to a disclosed nucleic acid sequence that encodes an amino acid. Such conservatively substituted variations of each explicitly listed nucleic acid and amino acid sequences are a feature of the present invention.

In addition, peptides comprising the core NAPVSIPQ (SEQ ID NO:6) active site can be easily made, e.g., by systematically adding one amino acid at a time and screening the resulting ADNF polypeptide for biological activity, as described herein. In addition, the contributions made by the side chains of various amino acid residues in such peptides can be probed via a systematic scan with a specified amino acid, e.g., Ala.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see Giliman & Smith, *Gene* 8:81–97 (1979); Roberts et al., *Nature* 328:731–734 (1987)).

Most commonly, polypeptide sequences are altered by changing the corresponding nucleic acid sequence and expressing the polypeptide. However, polypeptide sequences are also optionally generated synthetically using commercially available peptide synthesizers to produce any desired polypeptide (see Merrifield, supra, and Stewart & Young, supra).

One of skill can select a desired nucleic acid or polypeptide of the invention based upon the sequences provided and upon knowledge in the art regarding proteins generally. Knowledge regarding the nature of proteins and nucleic acids allows one of skill to select appropriate sequences with activity similar or equivalent to the nucleic acids and polypeptides disclosed herein. The definitions section, supra, describes exemplar conservative amino acid substitutions.

Finally, most modifications to the ADNF III nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

More particularly, it will be readily apparent to those of ordinary skill in the art that the ADNF III polypeptides of the present invention can readily be screened for neuroprotective/neurotrophic activity by employing the following CNS assay. Cerebral cortical cell cultures are prepared using the techniques described by Forsythe & Westbrook, *J. Physiol. Lond.* 396:515 (1988) with the following modifications. Cerebral cortex are used instead of hippocampus, and newborn rats are used instead of E16 mice. After nine days growth in vitro, the cultures are given a complete change of medium and treated with the ADNF III polypeptide of interest (dissolved in phosphate buffered saline) for an additional five days. To terminate, the cells are fixed for immunocytochemistry and neurons identified with antibodies against NSE (i.e., neuron specific enolase, a neuronal specific marker). Cell counts are performed on 30 fields, with total area of about 15 mm$^2$. Neurons are counted without knowledge of treatment. Control counts not treated with any drugs should run for purposes of comparison.

Using this assay, one of ordinary skill in the art can readily prepare a large number of ADNF III polypeptides in accordance with the teachings of the present invention and, in turn, screen them using the foregoing assay to find ADNF III polypeptides, in addition to those set forth herein, which possess the neuroprotective/neurotrophic activity of the intact ADNF II growth factor. For instance, using ADNF III-8 (i.e., Asn-Ala-Pro-Val-Ser-Ile-Pro-Gln (SEQ ID NO:6)) as a starting point, one can systematically add, for example, Gly-, Gly-Gly-, Leu-Gly-Gly- to the N-terminus of ADNF-8 and, in turn, screen each of these ADNF III polypeptides in the foregoing assay to determine whether they possess neuroprotective/neurotrophic activity. In doing so, it will be found that additional amino a ids can be added to both the N-terminus and the C-terminus of the newly discovered active site, i.e., Asn-Ala-Pro-Val-Ser-Ile-Pro-Gin (SEQ ID NO:6), without loss of biological activity as evidenced by the fact that the intact ADNF III growth factor exhibits extraordinary biological activity.

D. Screening for ADNF III Nucleic Acids and the Use of ADNF III Nucleic Acids as Molecular Probes In addition to their utility in encoding the polypeptides described herein, the nucleic acids of the invention are useful as molecular probes. A wide variety of formats and labels are available and appropriate for nucleic acid hybridization, including those reviewed in Tijssen, *Laboratory Techniques in Biochemistry and Molecular Biology—Hybridization with Nucleic Acid Probes* (1993); and *Methods In Molecular Biology, Volume 33-In Situ Hybridization Protocols* (Choo, ed., 1994) (see also other books in the *Methods in Molecular Biology* series); see especially, Chapter 21 of Choo, supra, "Detection of Virus Nucleic Acids by Radioactive and Nonisotopic in Situ Hybridization".

For instance, PCR, LCR and other amplification techniques are routinely used to detect ADNF III nucleic acids in biological samples. Accordingly, in one class of embodiments, the nucleic acids of the invention are used as primers or templates, or as positive controls in amplification reactions for the detection of ADNF III in a biological samples such as astroglial cells. Briefly, nucleic acids with sequence or subsequence identity or complementarity to SEQ ID NO:2 and SEQ ID NO:4 or the complements thereof, are used as templates to synthetically produce oligonucleotides of about 15–25 nucleotides with sequences similar or identical to the complement of a selected ADNF III nucleic acid subsequence. The oligonucleotides are then used as primers in amplification reactions such as PCR to detect selected ADNF III nucleic acids in biological samples, such as in astroglial cells. A nucleic acid of the invention (i.e., a cloned nucleic acid corresponding to the region to be amplified) is also optionally used as an amplification template in a separate reactions as a positive control to determine that the amplification reagents and hybridization conditions are appropriate.

Other methods for the detection of nucleic acids in biological samples using nucleic acids of the invention include Southern blots, northern blots, in situ hybridization (including fluorescent in situ hybridization (FISH), and a variety of other techniques overviewed in Choo (supra)). A variety of automated solid-phase detection techniques are also appropriate. For instance, very large stale immobilized polymer arrays (VLSIPS™) are used for the detection of nucleic acids (see Tijssen (supra), Fodor et al., *Science* 251:767–777 (1991); Sheldon et al., *Clinical Chemistry* 39(4):718–719 (1993); and Kozal et al., *Nature Medicine* 2(7):753–759 (1996)).

In one embodiment, ADNF III probes can be used as diagnostic markers for linked diseases such as epilepsy (e.g., ADNFLE). For example, polymorphic sites in ADNF III nucleic acids can be used to identify individuals with specific ADNF II alleles. Such diagnostic applications can help identify individuals with diseases such as ADNFLE.

E. Antibodies to Selected ADNF III Polypeptide(s)

Antibodies are raised to selected ADNF III polypeptides of the present invention, including individual, allelic, strain or species variants, and fragments thereof, both in their naturally occurring (full-length) forms and in recombinant forms. Additionally, antibodies are raised to these ADNF III polypeptides in either their native configurations or in non-native configurations. Anti-idiotypic antibodies can also be generated. Many methods of making antibodies are know to persons of skill in the art. The following discussion is presented as a general overview of the techniques available; however, one of skill will recognize that many variations upon the following methods are known.

A number of immunogens are used to produce antibodies specifically reactive with an ADNF III polypeptide having an amino ad sequence selected from the group consisting of SEQ ID NO:1, SEQ ID NO:3, SEQ ID NO:55, SEQ ID NO:57, and SEQ ID NO:59. Recombinant or synthetic polypeptides of8 amino acids in length, or greater, typically 20 amino acids in length, or greater, more typically 30 amino acids in length, or greater, selected from amino acid subsequences of an ADNF III polypeptide having an amino acid sequence selected from the group consisting of SEQ ID NO:1, SEQ ID NO:3, SEQ ID NO:55, SEQ ID NO:57, and SEQ ID NO:59 are the preferred polypeptide immunogens for the production of monoclonal or polyclonal antibodies. In one class of preferred embodiments, an immunogenic peptide conjugate is also included as an immunogen. Naturally occurring polypeptides are also used either in pure or impure form. An antigenic domain is ordinarily at least about 3 amino acids in length, often at least about 5 amino acids in length, generally at least about 9 amino acids in length and often at least about 15 amino acids in length. The antigenic domain ordinarily includes the binding site for an antibody, which typically vary from 3 to about 20 amino acids in length, and which are generally about 8 to 12 amine acids in length.

Recombinant ADNF III polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen (antigen), preferably a purified ADNF III polypeptide, an ADNF III polypeptide coupled to an appropriate carrier (e.g., GST, keyhole limpet hemanocyanin, etc.), or an ADNF III polypeptide incorporated into an immunization vector, such as a recombinant vaccinia virus (see U.S. Pat. No. 4,722,848), is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired (see, e.g., Coligan, *Current Protocols in Immunology* (1991) and Harlow & Lane, *Antibodies: A Laboratory Manual* (1989)).

Antibodies, including binding fragments and single chain recombinant versions thereof, against whole or predetermined fragments of selected ADNF III polypeptides are raised by immunizing animals, e.g., with conjugates of the fragments with carrier proteins as described above. Typically, the immunogen of interest is a peptide of at least about 8 amino acids, more typically the peptide is 20 amino acids in length, generally, the fragment is 25 amino acids in length and often the fragment is 30 amino acids in length or greater. The peptides are optionally coupled to a carrier protein (e.g., as a fusion protein), or are recombinantly expressed in an immunization vector. Antigenic determinants on selected ADNF III polypeptides to which antibodies bind are typically 3 to 10 amino acids in length.

Monoclonal antibodies are prepared from cells secreting the desired antibody. These antibodies are screened for binding to normal or modified polypeptides, or screened for agonistic or antagonistic activity, e.g., activity mediated through a selected ADNF III polypeptide. Specific monoclonal and polyclonal antibodies will usually bind with a $K_D$ of at least about 0.1 mM, more usually at least about 50 $\mu$M, and preferably at least about 1 $\mu$M or better.

In some instances, it is desirable to prepare monoclonal antibodies from various mammalian hosts, such as mice, rodents, primates, humans, etc. Description of techniques for preparing such monoclonal antibodies are found in, for example, *Basic and Clinical Immunology* (Stites et al., eds., 4th ed.) and references cited therein; Harlow & Lane, supra; Goding, *Monoclonal Antibodies: Principles and Practice* (2d ed. 1996); and Kohler & Milstein, *Nature* 256:495–497 (1975). Summarized briefly, this method proceeds by injecting an animal with an immunogen. The animal is then sacrificed and cells taken from its spleen, which are fused with myeloma cells. This results in a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimeric antibodies such as humanized murine antibodies.

Other suitable techniques involve selection of libraries of recombinant antibodies in phage or similar vectors (see, e.g., Huse et al., *Science* 246:1275–1281 (1989); Ward et al., *Nature* 341:544–546 (1989); and Vaughan et al., *Nature Biotechnology* 14:309–314 (1996)).

Frequently, the polypeptides and antibodies will be labeled by joining, either covalently or non-covalently, a substance that provides for a detectable signal. A wide variety of labels and conjugation techniques are known and are reported extensively in both the scientific and patent literature. Suitable labels include, but are not limited to, radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced (see U.S. Pat. No. 4,816,567; and Queen et al., *Proc. Nat'3l Acad. Sci. USA* 86:10029–10033 (1989)).

The antibodies of this invention are also used for affinity chromatography in isolating natural or recombinant ADNF III polypeptides. Columns are prepared, for example, with the antibodies linked to a solid support or solid particles, such as agarose, Sephadex, or the like, where a cell lysate is passed through the column, washed, and treated with increasing concentrations of a mild denaturant, whereby purified polypeptides are released.

The antibodies can be used to screen express on libraries for particular expression products such as normal or abnormal ADNF III polypeptides, or for related polypeptides related to a selected ADNF III polypeptide. Optionally, the antibodies in such a procedure are labeled with a moiety allowing easy detection of presence of antigen by antibody binding.

Antibodies raised against polypeptides can also be used to raise anti-idiotypic antibodies. Such antibodies are useful for detecting or diagnosing various pathological conditions related to the presence of the respective antigens.

The antibodies of this invention can also be administered to an organism (e.g., a human patient) for therapeutic purposes. Antibodies administered to an organism other than the species in which they are raised can be immunogenic. Thus, for example, murine antibodies administered to a human can induce an immunologic response against the antibody (e.g., the human anti-mouse antibody (HAMA) response), particularly after multiple administrations. The immunogenic properties of the antibody are reduced by altering portions, or all, of the antibody into characteristically human sequences thereby producing chimeric, or human, antibodies respectively.

Humanized (chimeric) antibodies are immunoglobulin molecules comprising a human and non-human portion. The antigen combining region (or variable region) of a humanized chimeric antibody is derived from a non-human source (e.g., murine) and the constant region of the chimeric antibody (which confers biological effector function, such as cytotoxicity, to the immunoglobulin) is derived from a human source. The humanized chimeric antibody has the antigen binding specificity of the non-human antibody molecule and the effector function conferred by the human antibody molecule. A large number of methods of generating chimeric antibodies are well known to those of skill in the art (see, e.g., U.S. Pat. Nos: 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369).

In general, the procedures used to produce these chimeric antibodies consist of the following steps (the order of some steps interchangeable): (a) identifying and cloning the correct gene segment encoding the antigen binding portion of the antibody molecule; this gene segment (known as the VDJ, variable, diversity and joining regions for heavy chains or VJ, variable, joining regions for light chains (or simply as the V or Variable region) may be in either the cDNA or genomic form; (b) cloning the gene segments encoding the constant region or desired part thereof; (c) ligating the variable region with the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); and, (f) introducing the DNA into eukaryotic cells (transfection) most often mammalian lymphocytes.

Antibodies of several distinct antigen binding specificities have been manipulated by these protocols to produce chimeric proteins (e.g., anti-TNP: Boulianne et al., *Nature* 312:643 (1984); and anti-tumor antigens: Sahagan et al., *J. Immunol.*, 137:1066 (1986)). Likewise, several different effector functions have been achieved by linking new sequences to those encoding the antigen binding region. Some of these effectors include enzymes (Neuberger et al., *Nature* 312:604 (1984)), immunoglobulin constant regions from another species, and constant regions of another immunoglobulin chain (Sharon et al., *Nature* 309:364 (1984); Tan et al., *J. Immunol.* 135:3565–3567 (1985)).

In one preferred embodiment, a recombinant DNA vector is used to transfect a cell line that produces an antibody. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function (e.g., a constant region of a human immunoglobulin), in which case the replacement gene contained in the recombinant vector may encode all or a portion of a region of an antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc. Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification may be used to alter the protein product of any monoclonal cell line or hybridoma. Such a procedure circumvents the task of cloning both heavy and light chain variable region genes from each B-cell clone expressing a useful antigen specificity. In addition to circumventing the process of cloning variable region genes, the level of expression of chimeric antibody is higher when the gene is at its natural chromosomal location, rather than at a random position in the genome. Detailed methods for preparation of chimeric (humanized) antibodies can be found in U.S. Pat. No. 5,482,856.

In another embodiment, this invention provides for fully human antibodies against selected ADNF III polypeptides. Human antibodies consist entirely of characteristically human immunoglobulin sequences. The human antibodies of this invention can be produced using a wide variety of methods (see, e.g., U.S. Pat. No. 5,001,065, for review).

In one preferred embodiment, the human antibodies of the present invention are produced initially in trioma cells. Genes encoding the antibodies are then cloned and expressed in other cells, such as nonhuman mammalian cells.

The general approach for producing human antibodies by trioma technology is described by Ostberg et al., *Hybridoma* 2: 361–367 (1983); U.S. Pat. No. 4,634,664; and U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Preparation of trioma cells requires an initial fusion of a mouse myeloma cell line with unimmortalized human peripheral B lymphocytes. This fusion generates a xenogeneic hybrid cell containing both human and mouse chromosomes (see Engelman, supra). Xenogeneic cells that have lost the capacity to secret antibodies are selected. Preferably, a xenogeneic cell is selected that is resistant to a selectable marker such as 8-azaguanine. Cells possessing resistance to 8-azaguanine are unable to propagate on hypoxanthine-aminopterin-thymidine (HAT) or azaserine-hypoxanthine (AH) media.

The capacity to secrete antibodies is conferred by a further fusion between the xenogeneic cell and B-lymphocytes immunized against a selected ADNF III polypeptide, or an epitope thereof. The B-lymphocytes are obtained from the spleen, blood or lymph nodes of human donor. If antibodies against a specific antigen or epitope are desired, it is preferable to use that antigen or epitope as the immunogen rather than a full length polypeptide. Alternatively, B-lymphocytes are obtained from an unimmunized individual and stimulated with a polypeptide, or a epitope thereof, in vitro. In a further variation, B-lymphocytes are obtained from an infected, or otherwise immunized individual, and then hyperimmunized by exposure to a selected ADNF III polypeptide for about seven to fourteen days, in vitro.

The immunized B-lymphocytes prepared by one of the above procedures are fused with a xeonogenic hybrid cell by well known methods. For example, the cells are treated with 40–50% polyethylene glycol of MW 1000–400, at about 37° C. for about 5–10 min. Cells are separated from the fusion mixture and propagated in media selective for the desired hybrids. When the xenogeneic hybrid cell is resistant to 8-azaguanine, immortalized trioma cells are conveniently selected by successive passage of cells on HAT or AH medium. Other selective procedures are, of course, possible depending on the nature of the cells used in fusion. Clones secreting antibodies having the required binding specificity are identified by assaying the trioma culture medium for the ability to bind to a selected ADNF III polypeptide or an epitope thereof. Triomas producing human antibodies having the desired specificity are subcloned, e.g., by the limiting dilution technique, and grown in vitro, in culture medium, or are injected into selected host animals and grown in vivo.

The trioma cell lines obtained are then tested or the ability to bind a polypeptide or an epitope thereof. Antibodies are separated from the resulting culture medium or body fluids by conventional antibody-fractionation procedures, such as ammonium sulfate precipitation, DEAE cellulose chromatography and affinity chromatography.

Although triomas are genetically stable, they do not produce antibodies at very high levels. Expression levels can be increased by cloning antibody genes from the trioma into one or more expression vectors, and transforming the vector into a cell line such as the cell lines typically used for expression of recombinant or humanized immunoglobulins. As well as increasing yield of antibody, this strategy offers the additional advantage that immunoglobulins are obtained from a cell line that does not have a human component, and does not therefore need to be subjected to the extensive viral screening required for human cell lines.

The genes encoding the heavy and light chains of immunoglobulins secreted by trioma cell lines are cloned according to methods, including the polymerase chain reaction, known in the art (see, e.g., Sambrook supra, and Berger & Kimmel, supra). For example, genes encoding heavy and light chins are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a trioma cell line. Alternatively, DNA segments encoding only a portion of the primary antibody genes are produced, which portions possess binding and/or effector activities. Other recombinant constructs contain segments of trioma cell line immunoglobulin genes fused to segments of other immunoglobulin genes, particularly segments of other human constant region sequences (heavy and/or light chain). Human constant region sequences can be selected from various reference sources including, but not limited to, those listed in Kabat et al., *Sequences of Proteins of Immunological Interest*, U.S. Department of Health and Human Services (1987).

In addition to the DNA segments encoding anti-ORF immunoglobulins or fragments thereof, other substantially homologous modified immunoglobulins can be readily designed and manufactured utilizing various recombinant DNA techniques known to those skilled in the art such as site-directed mutagenesis (see Gillman & Smith, *Gene* 8:81–97 (1979); Roberts et al., *Nature* 328:731–734 (1987)). Such modified segments will usually retain antigen binding capacity and/or effector function. Moreover, the modified segments are usually not so far changed from the original trioma genomic sequences to prevent hybridization to these sequences under stringent conditions. Because, like many genes, immunoglobulin genes contain separate functional regions, each having one or more distinct biological activities, the genes may be fused to functional regions from other genes to produce fusion proteins e.g., immunotoxins) having novel properties or novel combinations of properties.

The recombinant polynucleotide constructs will typically include an expression control sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the human immunoglobulins.

These expression vectors are typically replicable in the host organisms either as episomes or as an integral part of the host chromosomal DNA. Commonly, expression vectors will contain selection markers, e.g., ampicillin-resistance or hygromycin-resistance, to permit detection of those cells transformed with the desired DNA sequences. In general, prokaryotes or eukaryotic cells are used for cloning the DNA sequences encoding a human immunoglobulin chain.

Other approaches include in vitro immunization of human blood. In this approach, human blood lymphocytes capable of producing human antibodies are produced. Human peripheral blood is collected from the patient and is treated to recover mononuclear cells. The suppressor T-cells then are removed and remaining cells are suspended in a tissue culture medium to which is added the antigen and autologous serum and, preferably, a nonspecific lymphocyte activator. The cells then are incubated for a period of time so that they produce the specific antibody desired. The cells then can be fused to human myeloma cells to immortalize the cell line, thereby to permit continuous production of antibody (see U.S. Pat. No. 4,716,111).

In another approach, mouse-human hybridomas that produce human antibodies are prepared (see, e.g., U.S. Pat. No. 5,506,132). Other approaches include immunization of mice transformed to express human immunoglobulin genes, and phage display screening (Vaughan et al., supra.).

Thus, in view of the foregoing, it will be readily apparent to those of skill in the art that antibodies to ADNF III polypeptides have numerous uses. For instance, antibodies to the ADNF III polypeptides can be used to purify the ADNF III polypeptides of the present invention using affinity chromatograph, to detect the presence of an ADNF III polypeptide in a sample (e.g., in serum or cerebral spinal fluid (CSF)), to treat or block tumor growth. As such, antibodies to the ADNF II polypeptides have both diagnostic and therapeutic utilities.

F. Detection of ADNF III

Frequently, it is desirable to determine the presence or absence of ADNF III, or to quantify the expression of ADNF III polypeptides or nucleic acids in a sample. Detection of ADNF III or antisera against ADNF III is accomplished by assaying the products of the ADNF III nucleic acids of the invention, the nucleic acids themselves or the antibodies against polypeptides encoded by the nucleic acids.

The selected ADNF III nucleic acid or nucleic acid product (i.e., an mRNA or polypeptide) is preferably detected and/or quantified in a biological sample. Such samples include, but are not limited to, astroglial cells, brain, spleen, kidney or lung tissues or fine needle biopsy sample. Biological samples may also include sections of tissues such as frozen sections taken for histological purposes.

The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

In one embodiment, this invention provides or methods of detecting and/or quantifying ADNF III gene expression by assaying the underlying gene (or a fragment thereof), or by assaying the gene transcript (mRNA). The assay can be for the presence or absence of the gene or gene product or for the quantification of the transcription levels of the gene products.

In a preferred embodiment, nucleic acid assays are performed with a sample of nucleic acid isolated from the organism to be test. In the simplest embodiment, such a nucleic acid sample is the total m-RNA isolated from a biological sample. The nucleic acid (e.g., either genomic DNA or mRNA) may be isolated from the sample according to any of a number of methods well known to those of skill in the art.

Methods of isolating total DNA or mRNA are well known to those of skill in the art. For example, methods of isolation and purification of nucleic acids are described in detail in Chapter 3 of Tijssen, *Laboratory Techniques in Biochemistry and Molecular Biology—Hybridization With Nucleic Acid Probes: Theory and Nucleic Acid Preparation* (1993).

Frequently, it is desirable to amplify the nucleic acid sample prior to hybridization. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in *PCR Protocols, A Guide to Methods and Applications* (Innis et al., eds., 1990). Other suitable amplification methods include, but are not limited to those described supra.

Amplification-based assays are well known to those of skill in the art (see, e.g., Innis, supra.). The ADNF III nucleic acid sequences provided are sufficient to teach one of skill to routinely select primers to amplify any portion of the gene. It is expected that one of skill is thoroughly familiar with the theory and practice of nucleic acid hybridization and primer selection. The following reference provide a basic guide to nucleic acid hybridization: *Oligonucleotide Synthesis: A Practical Approach* (Gait, ed., 1984); Kuijpers *Nucleic Acids Research* 18(17):5197 (1994); Dueholm, *J. Org. Chem.* 59:5767–5773 (1994); and Tijssen, *Laboratory Techniques in Biochemistry and Molecular Biology— Hybridization with Nucleic Acid Probes* (1993). Innis, supra provides an overview of primer selection. In addition, PCR amplification products are optionally detected on a polymer array as described in Fodor et al. *Science* 251:767–777 (1991); Sheldon et al., *Clinical Chemistry* 39(4):718–719 (1993); and Kozal et al., *Nature Medicine* 2(7):753–759 (1996).

Most typically, amplification primers are between 8 and 100 nucleotides in length, and preferably between about 10 and 30 nucleotides in length. More typically, the primers are between about 15 and 25 nucleic acids in length.

One of skill will recognize that the 3' end of an amplification primer is more important for PCR than the 5' end. Investigators have reported PCR products where only a few nucleotides at the 3' end of an amplification primer were complementary to a DNA to be amplified. In this regard, nucleotides at the 5' end of a primer can incorporate structural features unrelated to the target nucleic acid; for instance, in one preferred embodiment, a sequencing primer hybridization site (or a complement to such as primer, depending on the application) is incorporated into the amplification primer, where the sequencing primer is derived from a primer used in a standard sequencing kit, such as one using a biotinylated dye-labeled universal M13 or SP6 primer. Alternatively, the primers optionally incorporated restriction endonuclease sites. The primers are selected so that there is no complementarity between any known sequence that is likely to occur in the sample to be amplified and any constant primer region. One of skill will appreciate that constant regions in primer sequences are optional.

Typically, all primer sequences are selected to hybridize only to a perfectly complementary DNA, with the nearest mismatch hybridization possibility from known DNA sequences that are likely to occur in the sample to be amplified having at least about 50 to 70% hybridization mismatches, and preferably 100% mismatches for the terminal 5 nucleotides at the 3' end of the primer.

The primers are selected so that no secondary structure forms within the primer. Self-complementary primers have poor hybridization properties, because the complementary portions of the primers self hybridize (i.e., form hairpin structures). The primers are also selected so that the primers do not hybridize to each other, thereby preventing duplex formation of the primers in solution, and possible concatenation of the primers during PCR. If there is more than one constant region in the primer, the constant regions of the primer are selected so that they do not self-hybridize or form hairpin structures.

Where sets of amplification primers (i.e., the 5' and 3' primers used for exponential amplification) are of a single length, the primers are selected so that they have roughly the same, and preferably exactly the same overall base composition (i.e., the same A+T to G+C ratio of nucleic acids). Where the primers are of differing lengths, the A+T to G+C ratio is determined by selecting a thermal melting temperature for the primer-DNA hybridization, and selecting an A+T to G+C ratio and probe length for each primer that has approximately the selected thermal melting temperature.

One of skill will recognize that there are a variety of possible ways of performing the above selection steps, and that variations on the steps are appropriate. Most typically, selection steps are performed using simple computer programs to perform the selection as outlined above; however, all of the steps are optionally performed manually. One available computer program for primer selection is the MacVector program from Kodak. In addition to commercially available programs for primer selection, one of skill can easily design simple programs for any of the preferred selection steps. Amplification primers can be selected to provide amplification products that span specific deletions, truncations, and insertions in an amplification target, thereby facilitating the detection of specific abnormalities such as a transposon insertion as described herein.

Where it is desired to quantify the transcription level (and thereby expression) of an ADNF III gene in a sample, the nucleic acid sample is one in which the concentration of the mRNA transcript(s) of the gene, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. This, for example, an assay where a 5 fold difference in concentration of a target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript is desired no elaborate control or calibration is required.

In addition to the foregoing, the expression of selected ADNF III polypeptides can also be detected and/or quantified by detecting or quantifying the expressed polypeptide. The polypeptides can be detected and quantified by any of a number of methods well known to those of skill in the art. Such methods include, but are not limited to, analytic biochemical methods such as electrophoresis, capillary electrophoresis, high performance liquid chromatography (HPLC), thin layer chromatography (TLC), hyperdiffusion chromatography and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent a western blotting, and the like.

In a particularly preferred embodiment, the ADNF II polypeptides are detected in an electrophoretic protein separation, more preferably in a two-dimensional electrophoresis, while in a most preferred embodiment, the polypeptides are detected using an immunoassay.

As used herein, an immunoassay is an assay that utilizes an antibody to specifically bind to the analyte (e.g., an ADNF III polypeptide having an amino acid sequence selected from the group consisting of SEQ ID NO:1, SEQ ID NO:3, SEQ ID NO:55, SEQ ID NO:57, and SEQ ID NO:59). The immunoassay is thus characterized by detection of specific binding of a polypeptide to an anti-polypeptide antibody, as opposed to the use of other physical or chemical properties to isolate, target, and quantify the analyte.

As indicated above, the presence or absence of polypeptides in a biological sample can be determined using electrophoretic methods. Mans of detecting proteins using electrophoretic techniques are well known to those of skill in the art (see generally, Scopes, *Protein Purification* (1982); Deutscher, *Methods in Enzymology Vol.* 182: *Guide to Protein Purification* (1990)).

In a preferred embodiment, the ADNF III polypeptides are detected and/or quantified using any of a number of well recognized immunological binding assays (see, e.g., U.S. Pat. Nos. 4,366,241; 4,376,110; 4,517,288; and 4,837,168) (for a review of the general immunoassays, see *Methods in Cell Biology Volume* 37. *Antibodies in Cell Biology* (Asai, ed., 1993); *Basic and Clinical Immunology* (Stites & Terr, eds., 7th ed. 1991)). Immunological binding assays (or immunoassays) typically utilize a "capture agent" to specifically bind to and often immobilize the analyte. The capture agent is a moiety that specifically binds to the analyte. In a preferred embodiment, the capture agent is an antibody that specifically binds polypeptide(s) or polypeptide subsequences (e.g., antigenic domains that specifically bind to the antibody). In a second preferred embodiment, the capture agent is the polypeptide and the analyte is antisera comprising an antibody that specifically binds to the polypeptide.

Immunoassays often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled anti-polypeptide antibody. Alternatively, the labeling agent may be a third moiety, such as another antibody, that specifically binds to the antibody/polypeptide complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as streptococcal protein A or protein G may also be used as the label agent. These proteins are normal constituents of the cell walls of streptococcal bacteria. They exhibit a strong non-immunogenic reactivity with immunoglobulin constant regions from a variety of species (see generally Kronval et al., i J. Immunol. 111:1401–1406 (1973), and Akerstrom et al., *J. Immunol.* 135: 2589–2542 (1985)).

Throughout the assays, incubation and/or washing steps are optionally performed after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

Immunoassays for detecting polypeptides may be either competitive or noncompetitive. Noncompetitive immunoassays are assays in which the amount of captured analyte is directly measured. In one preferred "sandwich" assay, for example, the capture agent can be bound directly to a solid substrate where they are immobilized. These immobilized capture agent then captures analyte present in the test sample. The analyte thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

In competitive assays, the initial amount of analyte present in the sample is measured indirectly by measuring the amount of an added (exogenous) analyte displaced (or competed away) from a capture agent by the analyte present in the sample. In one competitive assay, a known amount of, in this case, analyte is added to the sample and the sample is then contacted with a capture agent. The amount of exogenous analyte bound to the capture agent is inversely proportional to the initial analyte present in the sample.

Immunoassays in the competitive binding format can also be used for crossreactivity determinations. For example, a protein at least partially encoded by SEQ ID NO:1, SEQ ID NO:3, SEQ ID NO:55, SEQ ID NO:57, or SEQ ID NO:59, can be immobilized to a solid support. Related proteins (e.g., ADNF I) are added to the assay that compete for binding of the antisera to the immobilized antigen. The ability of the added proteins to compete for binding of the antisera to the immobilized protein is compared to the ability of the ADNF III polypeptide encoded by SEQ ID NO:1, SEQ ID NO:3, SEQ ID NO:55, SEQ ID NO:57, or SEQ ID NO:59 compete with itself. The percent crossreactivity for the above proteins is calculated, using standard calculations. Those antisera with less than 10% crossreactivity with each of the added proteins are selected and pooled. The cross-reacting antibodies are optionally removed from the pooled antisera by immunoabsorption with the added considered proteins, e.g., distantly related homologues.

The immunoabsorbed and pooled antisera are then used in a competitive binding immunoassay as described above to compare a second protein, thought to be perhaps an allele, interspecies homologue, or polymorphic variant of ADNF III to the immunogen protein (i.e., ADNF III of SEQ ID NO:1, SEQ ID NO:3, SEQ ID NO:55, SEQ ID NO:57, or SEQ ID NO:59). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:1, SEQ ID NO:3, SEQ ID NO:55, SEQ ID NO:57, or SEQ ID NO:59 that is required to inhibit 50% of binding, then the second protein is said to specifically bind to the polyclonal antibodies generated to an ADNF III immunogen.

In a preferred embodiment, western blot (immunoblot) analysis is used to detect and quantify the presence of selected ADNF III polypeptides in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the selected polypeptide. The antibodies specifically bind to polypeptide on the solid support. These antibodies are optionally directly labeled or, alternatively, are optionally subsequently detected using labeled antibodies (e.g., labeled sheep anti-mouse antibodies) that specifically bind to the selected polypeptide.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–4 (1986)). Enzyme linked assays (e.g., ELISA assays) are also preferred.

The assays of this invention as scored (as positive or negative for ADNF III or a selected ADNF III polypeptide) according to standard methods well known to those of skill in the art. The particular method of scoring will depend on the assay format and choice of label. For example, a western blot assay can be scored by visualizing the colored product produced by the enzymatic label. A clearly visible colored band or spot at the correct molecular weight is scored as a positive result, while the absence of a clearly visible spot or band is scored as a negative. In a preferred embodiment, a positive test will show a signal intensity (e.g., polypeptide quantity) at least twice that of the background and/or control and more preferably at least 3 times or even at least 5 times greater than the background and/or negative control.

One of skill in the art will appreciate that it is often desirable to reduce non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin.

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, texas red, rhodamine, and the like), radiolabels (e.g., $^3$H, $^{125}$I, $^{14}$C or $^{32}$P), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule that is either inherently detectable or covalently bound to a signal system, such as a detectable enzyme, a fluorescent compound, or a chemiluminescent compound. A number of ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

For a review of various labeling or signal producing systems that may be used, see U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

As mentioned above, depending upon the assay, various components, including the antigen, target antibody, or antiantibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through non-specific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers that form several aqueous phases, such as dextrans polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups that may be present on the surface and used for linking can include carboxylic acids, aldehydes, amino groups, cyano groups, ethiylenic groups, hydroxyl groups, mercapto groups and the like. The manner of linking a wide variety of compounds to various surfaces is well known and is amply illustrated in the literature (see, e.g., *Immobilized Enzymes* (Chibata, ed. 1978); and Cuatrecasas, *J. Biol. Chem.* 245:3059 (1970)).

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

G. Methods For Preventing Neuronal Cell Death Using Neurotrophic ADNF III Polypeptides In another aspect, the present invention provides a method for preventing neuronal cell death, the method comprising contacting the neuronal cells with an Activity Dependent Neurotrophic Factor (ADNF) III polypeptide in an amount sufficient to prevent neuronal cell death. In one embodiment, the ADNF III polypeptide has an amino acid sequence selected from the group consisting of SEQ ID NO:1, SEQ ID NO:3, SEQ ID NO:55, SEQ ID NO:57, or SEQ ID NO:59 and conservatively modified variations thereof. In another embodiment, the ADNF III polypeptide comprises the following amino acid sequence:

$(R^1)_x$-Asn-Ala-Pro-Val-Ser-Ile-Pro-Gln-$(R^2)_y$ (SEQ ID NO:10)

and conservatively modified variations thereof.

In the above formula, $R^1$ is an amino acid sequence comprising from 1 to about 40 amino acids wherein each amino acid is independently selected from the group consisting of naturally occurring amino acids and amino acid analogs. The term "independently selected" is used herein to indicate that the amino acids making up the amino acid sequence $R^1$ may be identical or different (e.g., all of the amino acids in the amino acid sequence may be threonine, etc.). Moreover, as previously explained, the amino acids making up the amino acid sequence $R^1$ may be either naturally occurring amino acids, or known analogues of natural amino acids that functions in a manner similar to the naturally occurring amino acids (i.e., amino acid mimetics and analogs). Suitable amino acids that can be used to form the amino acid sequence $R^1$ include, but are not limited to, those listed in Table 1, supra.

As with $R^1$, $R^2$, in the above formula, is an amino acid sequence comprising from 1 to about 40 amino acids wherein each amino acid is independently selected from the group consisting of naturally occurring amino acids and amino acid analogs. Moreover, as with $R^1$, the amino acids making up the amino acid sequence $R^2$ may be identical or different, and may be either naturally occurring amino acids, or known analogues of natural amino acids that functions in a manner similar to the naturally occurring amino acids (i.e., amino acid mimetics and analogs). Suitable amino acids that can be used to form $R^2$ include, but are not limited to, those listed in Table I, supra.

Within the above formula, x and y are independently selected and are equal to zero or one. The term independently selected is used herein to indicate that x and y may identical or different. For example, x and y may both be zero or, alternatively, x and y may both be one. In addition, x may be zero and y may be one or, alternatively, x may be one and y may be zero. Moreover, if x and y are both one, the amino acid sequences $R^1$ and $R^2$ may be the same or different. As such, the amino acid sequences $R^1$ and $R^2$ are independently selected. If $R^1$ $R^2$ are the same, they are identical in terms of both chain length and amino acid composition. For example, both $R^1$ and $R^2$ may be Val-Leu-Gly-Gly-Gly (SEQ ID NO:13). If $R^1$ and $R^2$ are different, they can differ from one another in terms of chain length and/or amino acid composition and/or order of amino acids in the amino acids sequences. For example, $R^1$ may be Val-Leu-Gly-Gly-Gly (SEQ ID NO:13), whereas $R^2$ may be Val-Leu-Gly-Gly (SEQ ID NO:14). Alternatively, $R^1$ may be Val-Leu-Gly-Gly-Gly (SEQ ID NO:13), whereas $R^2$ may be Val-Leu-Gly-Gly-Val (SEQ ID NO:15). Alternatives, $R^1$ may be Val-Leu-Gly-Gly-Gly (SEQ ID NO:13), whereas $R^2$ may be Gly-Val-Leu-Gly-Gly (SEQ ID NO:16).

Within the scope of the above formula, certain ADNF III polypeptides are preferred, namely those in which x and y are both zero (i.e. ADNF III-8). Equally preferred are ADNF III polypeptides in which x is one; $R^1$ Gly-Gly; and y is zero (SEQ ID NO:33). Also equally preferred are ADNF III polypeptides in which is one; $R^1$ is Leu-Gly-Gly; y is one; and $R^2$ is -Gln-Ser (SEQ ID NO:34). Also equally preferred are ADNF III polypeptides in which x is one; $R^1$ is Leu-Gly-Leu-Gly-Gly- (SEQ ID NO:17); y is one; and $R^2$ is -Gln-Ser (SEQ ID NO:35). Also equally preferred are ADNF III polypeptides in which x is one; $R^1$ is Ser-Val-Arg-Leu-Gly-Leu-Gly-Gly-(SEQ ID NO:18); y is one; and $R^2$ is -Gln-Ser (SEQ ID NO:12). Additional amino acids can be added to both the N-terminus and the C-terminus of the newly discovered active site without loss.of biological activity as evidenced by fact that the intact ADNF III growth factor exhibits extraordinary biological activity.

As previously explained, the ADNF III polypeptides of the present invention can be used in the treatment of neurological deficiencies and for the prevention of neuronal cell death. For example, such ADNF III polypeptides can be used to prevent the death neuronal cells including, but not limited to, spinal cord neurons, hippocampal neurons, cerebral cortical neurons and cholingeric neurons. More particularly, the ADNF III polypeptides of the present invention can be used in the prevention of cell death associated with (1) gp120, the envelope protein from HIV; (2) N-methyl-D-aspartic acid (excito-toxicity); (3) tetrodotoxin (blockage of electrical activity); and (4) β-amyloid peptide, a substance related to neuronal degeneration in Alzheimer's disease. Each of the various methods of using the ADNF III polypeptides of the present invention to prevent neuronal cell death or damage will be explained in greater detail hereinbelow. From these examples, it will be readily apparent to those of skill in the art that the ADNF III polypeptides of the present invention can be used in a similar manner to prevent neuronal cell death associated with a number of other neurological diseases and deficiencies.

In this connection, it has now been discovered that the ADNF III polypeptides of the present invention can be used to prevent gp120-induced neuronal cell death. Thus, by administering an effective amount of an ADNF III polypeptide of the present invention to a patient infected with the HIV-1 virus, gp120-induced neuronal cell death can be prevented. As such, in one aspect, the present invention provides a method for preventing neuronal cell death in a patient infected with human immunodeficiency virus, the method comprising administering to the patient an Activity Dependent Neurotrophic Factor (ADNF) III polypeptide in an amount sufficient to prevent neuronal cell death and a pharmaceutically acceptable carrier. In one embodiment, the ADNF III polypeptide has an amino acid sequence selected from the group consisting of SEQ ID NO:1, SEQ ID NO:3, SEQ ID NO:55, SEQ ID NO:57, or SEQ ID NO:59 and conservatively modified variations thereof. In another embodiment, the ADNF III polypeptide comprises the following amino acid sequence:

$(R^1)_x$-Asn-Ala-Pro-Val-Ser-Ile-Pro-Gln-$(R^2)_y$ (SEQ ID NO:10)

and conservatively modified variations thereof.

The previous discussion pertaining to $R^1$, $R^2$, x and y is fully applicable to the ADNF III polypeptides used in this method of the present invention and, thus, will not be repeated with respect to this particular method. Within the scope of the above formula, certain ADNF III polypeptides are preferred, namely those in which x and y are both zero (i.e., ADNF III-8). Equally preferred are ADNF III polypeptides in which x is one; $R^1$ is Gly-Gly-; and y is zero (SEQ ID NO:33). Also equally preferred are ADNF III polypeptides in which x is one; $R^1$ is Leu-Gly-Gly-; y is one; and $R^2$ is -Gln-Ser (SEQ ID NO:34). Also equally preferred are ADNF III polypeptides in which x is one; $R^1$ Leu-Gly-Leu-Gly-Gly-(SEQ ID NO:17); y is one; and $R^2$ is -Gln-Ser. Also equally preferred are ADNF III polypeptides in which x is one; $R^1$ is Ser-Val-Arg-Leu-Gly-Leu-Gly-Gly- (SEQ ID NO:18); y is one; and $R^2$ is -Gln-Ser (SEQ ID NO:12).

Moreover, it will be readily apparent to those of skill in the art that using the teachings set forth above with respect to the design and synthesis of ADNF III polypeptides and the assay of Brenneman et al., *Nature* 335:636 (1988), the teachings of which are hereby incorporated in their entirety by reference one of ordinary skill in the art can identify other ADNF III polypeptides that can be used to prevent cell death associated with gp120.

In addition to the foregoing, it has also been discovered that ADNF III polypeptides can be used to prevent neuronal cell death associated with NMDA toxicity in dissociated cerebral cortical cultures. As such, in another aspect, the present invention provides a method for preventing neuronal cell death associated with excito-toxicity induced by N-methyl-D-aspartate stimulation, the method comprising contacting these neuronal cells with an Activity Dependent Neurotrophic Factor (ADNF) III polypeptide in an amount sufficient to prevent neuronal cell death. In one embodiment, the ADNF III polypeptide has an amino acid sequence selected from the group consisting of SEQ ID NO:1, SEQ ID NO:3, SEQ ID NO:55, SEQ ID NO:57, or SEQ ID NO:59 and conservatively modified variations thereof. In another embodiment, the ADNF III polypeptide comprises the following amino acid sequence:

$(R^1)_x$-Asn-Ala-Pro-Val-Ser-Ile-Pro-Gln-$(R^2)_y$ (SEQ ID NO:10)

and conservatively modified variations thereof.

The previous discussion pertaining to $R^1$, $R^2$, x and y is fully applicable to the ADNF III polypeptides used in this method of the present invention and, thus, will not be repeated with respect to this particular method. Within the scope of the above formula, certain ADNF III polypeptides are preferred, namely those in which x and y are both zero (i.e., ADNF III-8). Equally preferred are ADNF III polypeptides in which x is one; $R^1$ is -Gly-Gly; and y is zero (SEQ ID NO:33). Also equally preferred are ADNF III polypeptides in which x is one; $R^1$ is -Leu-Gly-Gly; y is one; and $R^2$ is -Gln-Ser (SEQ ID NO:34). Also equally preferred are ADNF III polypeptides in which x is one; $R^1$ is Leu-Gly-Leu-Gly-Gly-(SEQ ID NO:17); y is one; and $R^2$ is -Gln-Ser (SEQ ID NO:35). Also equally preferred are ADNF III polypeptides in which x is one; $R^1$ is Ser-Val-Arg-Leu-Gly-Leu-Gly-Gly-(SEQ ID NO:18); y is one; and $R^2$ is -Gln-Ser (SEQ ID NO:12).

Moreover, it will be readily apparent to those of skill in the art that using the teachings set forth above with respect to the design and synthesis of ADNF III polypeptides and the assay of Brenneman & Gozes, *J. Clin. Invest.* 97:2299–2307 (1996), the teachings of which are hereby incorporated in their entirety by reference, one of ordinary skill in the art can identify other ADNF III polypeptides that can be used to prevent cell death associated with excito-toxicity induced by stimulation by N-methyl-D-aspartate.

In addition to the foregoing, it has also been discovered that the ADNF III polypeptides of the present invention can prevent cell death associated with Alzheimer's disease. An in vitro model for Alzheimer's disease is offered by β-amyloid neurotoxicity. As such, in another aspect, the present invention provides a method of preventing neuronal cell death induced by the β-amyloid peptide in a patient afflicted or impaired with Alzheimer's disease, the method comprising administering to the patient an Activity Dependent Neurotrophic Factor III (ADNF III) polypeptide in an amount sufficient to prevent neuronal cell death and a pharmaceutically acceptable carrier. In one embodiment, the ADNF III polypeptide has an amino acid sequence selected from the group consisting of SEQ ID NO:1, SEQ ID NO:3, SEQ ID NO:55, SEQ ID NO:57, or SEQ ID NO:59 and conservatively modified variations thereof. In another embodiment, the ADNF III polypeptide comprises the following amino acid sequence:

$(R^1)_x$-Asn-Ala-Pro-Val-Ser-Ile-Pro-Gln-$(R^{12})_y$(SEQ ID NO:10) and conservatively modified variations thereof.

The previous discussion pertaining to $R^1$, $R^2$, x nd y is fully applicable to the ADNF III polypeptides used in this method of the present invention and, thus, will not be repeated with respect to this particular method. Within the scope of the above formula, certain ADNF III polypeptides are preferred, namely those in which x and y are both zero (i.e., ADNF III-8). Equally preferred are ADNF III polypeptides in which x is one; $R^1$ is Gly-Gly-; and y is zero (SEQ ID NO:33). Also equally preferred are ADNF III polypeptides in which x is one; $R^1$ is Leu-Gly-Gly-; y is one; and $R^2$ is -Gln-Ser (SEQ ID NO:34). Also equally preferred are ADNF III polypeptides in which x is one; $R^1$ is Leu-Gly-Leu-Gly-Gly- (SEQ ID NO:17); y is one; and $R^2$ is -Gln-Ser (SEQ ID NO:35). Also equally preferred are ADNF III polypeptides in which x is one; $R^1$ is Ser-Val-Arg-Leu-Gly-Leu-Gly-Gly- (SEQ ID NO:18); y is one; and $R^2$ is -Gln-Ser (SEQ ID NO:12).

Moreover, it will be readily apparent to those of skill in the art that using the teachings set forth above with respect to the design and synthesis of ADNF III polypeptides and the assays set forth by Brenneman & Gozes, *J. Clin. Invest.*, 97:2299–2307 (1996), the teachings of which are hereby incorporated in their entirety by reference, one of ordinary skill in the art can identify other ADNF III polypeptides that can be used to prevent cell death induced by the β-amyloid peptide in a patient afflicted or impaired with Alzheimer's disease.

In addition to the foregoing, it has also been discovered that the ADNF III polypeptides of the present invention can alleviate learning impairment produced by cholinergic blockade. As such, in still another aspect, the present invention provides a method of alleviating learning impairment produced by cholingeric blockage in a patient afflicted or impaired with Alzheimer's disease, the method comprising administering to the patient an Activity Dependent Neurotrophic Factor III polypeptide in an amount sufficient to prevent neuronal cell death and a pharmaceutically acceptable carrier. In one embodiment, the ADNF III polypeptide has an amino acid sequence selected from the group consisting of SEQ ID NO:1, SEQ ID NO:3, SEQ ID NO:55, SEQ ID NO:57, or SEQ ID NO:59 and conservatively modified variations thereof. In another embodiment, the ADNF III polypeptide comprises the following amino acid sequence:

$(R^1)_x$-Asn-Ala-Pro-Val-Ser-Ile-Pro-Gln-$(R^2)_y$ (SEQ ID NO:10) and conservatively modified variations thereof.

The previous discussion pertaining to $R^1$, $R^2$, x and y is fully applicable to the ADNF III polypeptides used in this method of the present invention and, thus, will not be repeated with respect to this particular method. Within the scope of the above formula, certain ADNF III polypeptides are preferred, namely those in which x and y are both zero (i.e., ADNF III-8). Equally preferred are ADNF III polypeptides in which x is one; $R^1$ is Gly-Gly-; and y is zero (SEQ ID NO:33). Also equally preferred are ADNF III polypeptides in which x is one; $R^1$ is Leu-Gly-Gly-; y is one; and $R^2$ is -Gln-Ser (SEQ ID NO:34). Also equally preferred are ADNF III polypeptides in which x is one; $R^1$ is Leu-Gly-Leu-Gly-Gly- (SEQ ID NO:17); y is one; and $R^2$ is -Gln-Ser (SEQ ID NO:35). Also equally preferred are ADNF III polypeptides in which x is one; $R^1$ is Ser-Val-Arg-Leu-Gly-Leu-Gly-Gly- (SEQ ID NO:18); y is one; and $R^2$ is -Gln-Ser (SEQ ID NO:12).

Moreover, it will be readily apparent to those of skill in the art that using the teachings set forth above with respect to the design and synthesis of ADNF III polypeptides and the assays set forth by Gozes et al., *Proc. Natl. Acad. Sci. USA*, 93:427–432 (1996), the teachings of which are hereby incorporated in their entirety by reference, one of ordinary skill in the art can identify other ADNF III polypeptides that can be used to alleviate learning impairment produced by cholingeric blockage in a patient afflicted or impaired with Alzheimer's disease.

In addition to the foregoing, ADNF III polypeptides of the present invention are useful in the treatment and diagnosis of neurodegenerative pathologies including, but not limited to, those arising from a disease state and/or having an excitotoxic/ischemic mechanism. For example, post-mortem Alzheimer's brains demonstrate increased ADNF III mRNA expression as compared to non-Alzheimer brain tissue.

Pathologies that would benefit from therapeutic and diagnostic applications of this invention include conditions (diseases and insults) leading to neuronal cell death and/or sub-lethal neuronal pathology including, for example, the following:

diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supra-nuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity;

diseases affecting sensory neurons such as Friedreich's ataxia, diabetes, peripheral neuropathy, retinal neuronal degeneration;

diseases of limbic and cortical systems such as cerebral amyloidosis, Pick's atrophy, Retts syndrome;

neurodegenerative pathologies involving neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration;

pathologies associated with developmental retardation and learning impairments, Down's syndrome, and oxidative stress induced neuronal death;

pathologies arising with aging and chronic alcohol or drug abuse including, for example, with alcoholism the degeneration of neuron in locus coeruleus, cerebellum, cholinergic basal forebrain; with aging degeneration of cerebellar neurons and cortical neurons leading to cognitive and motor impairments; an with chronic amphetamine abuse degeneration of basal ganglia neurons leading to motor impairments;

pathological changes resulting from focal trauma such as stroke, focal ischemia, vascular insufficiency, hypoxic-ischemic encephalopathy, hyperglycemia, hypoglycemia, closed head trauma, or direct trauma;

pathologies arising as a negative side-effect of therapeutic drugs and treatments (e.g., degeneration of cingulate and entorhinal cortex neurons in response to anticonvulsant doses of antagonists of the NMDA class of glutamate receptor).

In still yet another aspect, the present invention provides pharmaceutical compositions comprising one of the previously described ADNF III polypeptides in an amount sufficient to exhibit neuroprotective/neurotrophic activity, and a pharmaceutically acceptable diluent, carrier or excipient. In one embodiment, the ADNF III polypeptide has an amino acid sequence selected from the group consisting of SEQ ID NO:1, SEQ ID NO:3, SEQ ID NO:55, SEQ ID NO:57, or SEQ ID NO:59 and conservatively modified variations thereof. In another embodiment, the ADNF III polypeptide comprises the following amino acid sequence:

$(R^1)_x$-Asn-Ala-Pro-Val-Ser-Ile-Pro-Gln $(R^2)_y$ (SEQ ID NO:10) and conservatively modified variations thereof.

The previous discussion pertaining to $R^1$, $R^2$, x and y is fully applicable to the ADNF III polypeptides used in this method of the present invention and, thus, will not be repeated with respect to this particular method. Within the scope of the above formula, certain ADNF III polypeptides are preferred, namely those in which x and y are both zero (i.e., ADNF III-8). Equally preferred are ADNF III polypeptides in which x is one; $R^1$ is Gly-Gly-; and y is zero (SEQ ID NO:33). Also equally preferred are ADNF III polypeptides in which x is one; $R^1$ is Leu-Gly-Gly-; y is one; and $R^2$ is -Gln-Ser (SEQ ID NO:34). Also equally preferred are ADNF III polypeptides in which x is one; $R^1$ is Leu-Gly-Leu-Gly-Gly- (SEQ ID NO:17); y is one; and $R^2$ is -Gln-Ser (SEQ ID NO:35). Also equally preferred are ADNF III polypeptides in which x is one; $R^1$ is Ser-Val-Arg-Leu-Gly-Leu-Gly-Gly- (SEQ ID NO:18); y is one; and $R^2$ is -Gln-Ser (SEQ ID NO:12).

The pharmaceutical compositions of the present invention are suitable for use in a variety of drug delivery systems. Peptides that have the ability to cross the blood brain barrier can be administered, e.g., systemically, nasally, etc., using methods known to those of skill in the art. Larger peptides that do not have the ability to cross the blood brain barrier can be administered to the mammalian brain via intracerebroventricular (ICV) injection or via a cannula using techniques well known to those of skill in the art (see, e.g., Motta & Martini, Proc. Soc. Exp. Biol. Med. 168:62–64 (1981); Peterson et al., Biochem. Pharamacol. 31:2807–2810 (1982); Rzepczynski et al., Metab. Brain Dis. 3:211–216 (1988); Leibowitz et al., Brain Res. Bull. 21:905–912 (1988); Sramka et al., Stereotact. Funct. Neurosurg. 58:79–83 (1992); Peng et al., Brain Res. 632:57–67 (1993); Chem et al., Exp. Neurol. 125:72–81 (1994); Nikkhah et al., Neuroscience 63:57–72 (1994); Anderson et al., J. Comp. Neurol. 357:296–317 (1995); and Brecknell & Fawcett, Exp. Neurol. 138:338–344 (1996)).

Suitable formulations for use in the present invention are found in Remington's Pharmaceutical Sciences (17th ed. 1985)), which is incorporated herein by reference. In addition, for a brief review of methods for drug delivery, see Langer, Science 249:1527–1533 (1990), which is incorporated herein by reference. Suitable dose ranges are described in the examples provided herein, as well as in U.S. Ser. No. 08/324,297, herein incorporated by reference.

Due to its ability to increase growth and survival of neurons, ADNF III polypeptides have extensive uses in the treatment of neurological deficiencies that result, for example, from neuronal development, aging, neurodegenerative diseases or spinal cord injury. As such, the present invention provides for therapeutic compositions or medicaments comprising one or more of the ADNF III polypeptides described hereinabove in combination with a pharmaceutically acceptable excipient, wherein the amount of the ADNF III polypeptide is sufficient to provide a therapeutic effect.

In a therapeutic application, the ADNF III polypeptides of the present invention are embodied in pharmaceutical compositions intended for parenteral, topical, oral or local administration. Preferably, the pharmaceutical compositions are administered parenterally, e.g., intravenously, subcutaneously, intradermally, or intramuscularly, or intranasally. Thus, the invention provides compositions for parenteral administration that comprise a solution of an ADNF III polypeptide, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride potassium chloride, calcium chloride, sorbitan monolaurate, triethanolamine oleate, etc.

For solid compositions, conventional nontoxic solid carriers may be used that include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the ADNF III polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, the ADNF III polypeptides of the invention are administered to a patient in an amount sufficient to prevent neuronal cell death. An amount adequate to accomplish this is defined as "therapeutically effective dose." Amounts effective for this use will depend on, for example, the particular ADNF III polypeptide employed, the type of neuronal cell death or damage to be prevented, the manner of administration, the weight and general state of health of the patient, and the judgment of the prescribing physician. For example, for the prevention of neuronal cell death, an amount of ADNF III polypeptide falling within the range of a 100 ng to 10 mg dose given intranasally once a day (e.g., in the evening) would be a therapeutically effective amount.

The invention will be described in greater detail by way of specific examples. The following examples are offered for illustrative purposes, and are not intended to limit the invention in any manner. Those of skill in the art will readily recognize a variety of noncritical parameters that can be changed or modified to yield essentially the same results.

EXAMPLES

A. MATERIALS AND METHODS

1. Cell Cultures a. Astrocytes: Astrocytes were prepared from 1-day-old (Sprague-Dawley) rats. Cerebral cortices from 10–12 pups were rapidly dissected into sterile HBSS medium (Hanks balanced salt solution). After the meninges were carefully removed, cells were mechanically dissociated and then treated with 0.125% trypsin for 20 min. Finally, Dulbecco modified Eagle medium (DMEM) containing 10% fetal calf serum was added. After mixing, the cell suspension was plated in 75-cm$^2$ flasks at a concentration of $15 \times 10^6$ cells per flask and incubated at 10% $CO_2$ at 37° C. The medium in the culture system consisted of DMEM, 10% FBS, 50 mg/ml gentamycin and a mixture of penicillin G sodium salt, streptomycin sulfate and nystatin (100 ml/100 ml medium from a stock solution of 10,000 U/ml penicillin, 10 mg/ml streptomycin and 1250 U/ml nystatin). Culture medium was changed at 2 and 5 days after plating. Six days after plating, in order to dislodge residual neurons and/of oligodendrocytes, the cells were split 1:1. They were treated again with trypsin, dislodged from the flask and suspended in 10% fetal calf serum/DMEM. Cultures were plated again in 75-cm$^2$ flasks and four days later were used as a source of conditioned medium. Two-week-old cultures were washed three times with 15 ml phosphate buffered saline (PBS) and then incubated during 3 hours with 15 ml PBS containing 0.25 nM VIP (a stock solution contained 1 mg VIP dissolved in 0.3 ml 0.01 N acetic acid and diluted thereafter). Conditioned medium was collected, the media was centrifuged for 10 min. at 1000×g to sediment intact cells and stored at −20° C. until use.

b. Neuroblastoma cell line: Cultures, prepared as before (Lilling, *J. Mol. Neurosci.* 5:231–239 (1994/5)), were washed three times with 15 ml phosphate buffered saline (PBS) and then incubated during a 3 hour period with 15 ml PBS containing 0.25 nM VIP (a stock solution contained 1 mg VIP dissolved in 0.3 ml 0.01 N acetic acid as above). Conditioned medium was collected as above.

2. ADNF Purification

ADNF was purified according to the method described by Brenneman & Gozes, *J. Clin. Invest.* 97:2299–2307 (1996)). Briefly, 2-wk old astroglial cultures (confluent 75-cm$^2$ flasks) were washed three times with PBS and conditioned medium was collected (10 ml PBS/flask) during a 3-h incubation with 0.1 nM VIP (an amount previously shown to be optimal for releasing neurotrophic activity from astroglial cells). The medium was centrifuged (3,000×g for 10 min) and dialyzed (3.5-kD cutoff) against 50 mM sodium phosphate buffer, pH 7.0, 4° C. Neuroprotection was assayed initially in tetrodotoxin-blocked spinal cord cultures. The rationale for choosing tetrodotoxin-blocked culture cells for assays of survival-promoting activities secreted from glial cells in the presence of VIP was that treatment with 1 μM tetrodotoxin blocked spontaneous synaptic activity, thereby inhibiting the synthesis (Agostan et al., *Mol. Brain. Res.* 10:235–240 (1991)) and release (Brenneman et al., *Peptides* 6(2):35–39 (1985)) of endogenous VIP, rendering the system dependent on exogenous VIP.

The first purification step in the isolation of ADNF was DEAE-Sephacel chromatography (Pharmacia Diagnostics AB, Uppsala, Sweden) of VIP-stimulated astroglia-conditioned medium (300 ml, 6–8 mg protein) was loaded onto a DEAE-Sephacel column (0.75 cm in diameter and 3 cm in length) preequilibrated with 50 mM sodium pyrophosphate buffer, pH 7.0. The column was washed sequentially with 40 ml of 50 mM sodium pyrophosphate buffer (pH 7.0) and then the same buffer supplemented with increasing concentrations of NaCl, 0.1 M, 0.26 M, 0.5 M, 1.0 M, 2 M and 3M. Column fractions, after dialysis against water (1:10,000), were added together with 1 μM tetrodotoxin to the spinal cord test cultures. Neuroprotective activity was determined by gauging the effects on the number of surviving spinal cord neurons. Significant increases in neuronal cell counts were observed in the 2 M NaCl eluate. The second purification step was size separation of the active DEAE fraction (2 M NaCl eluate) on fast performance liquid chromatography (FPLC: Pharmacia Diagnostics AB). The 2 M NaCl fraction (corresponding to 300 ml original conditioned medium preparation) was dialyzed against water, lyophilized, and resuspended in 0.5 ml of 50 mM sodium phosphate (pH 7.3) containing 0.15 M NaCl. 0.25-ml aliquots were loaded on a Superose™ (Pharmacia Diagnostics AB) 12-column (prepacked HR 10/30) FPLC. Factions (0.5 ml, 0.4 ml/min) were collected from the column, diluted (1:10,000), and tested in the neuronal survival assay. Significant increases in neuronal cell counts were observed in column fractions 22 and 31. A third purification step of the low molecular weight neuroprotective activity included hydrophobic interaction (Alkyl-Superose™ HR5/5, Pharmacia Diagnostics AB) FPLC. The column was washed with 0.1 M phosphate buffer (pH 7.0) and equilibrated with 0.1 M phosphate buffer (pH 7.0) containing 2.0 M $(NH_4)_2SO_4$. The sample (0.5 ml of eluted fraction 31 from the size fractionation FPLC) was dialyzed extensively against deionized water, lyophilized, and resuspended in 0.1 M sodium phosphate buffer, pH 7.0, containing 1.43 M $(NH_4)_2SO_4$. Elution (1-ml fractions, 0.5 ml/min) was performed with a linear gradient of salt removal (2.0–0 M) initiated 10 min. after injection and lasting 50 min. Protein samples were dialyzed extensively against deionized water and analyzed for protein concentrations (protein assay: Bio-Rad Laboratories, Richmond, Calif.). After hydrophobic interaction chromatography, the amount of protein in the active fraction was determined by total amino acid analysis on an instrument (model 7300, Beckman Instrs., Fullerton, Calif.) after hydrolysis (24 h/110° C.) in 6 N HCl containing 0.2% phenol. Samples eluted from the hydrophobic interaction column by salt removal were tested for biological activity and absorbance at 280 nm after dialysis against water.

3. Peptide Sequencing a. V8 protease digestion: For peptide sequencing, HPLC-eluted ADNF (3–5 μg) was subjected to V8 protease digestion (Boeringer Mannheim, Indianapolis, Ind.). The reaction was carried out in 50 mM ammonium hydrogen carbonate, pH 7.8, with an enzyme to substrate ratio of 1:50 at 37° C. for 16 h. Resulting peptides were resolved by HPLC as described by Brenneman & Gozes, J. Clin. Invest., 97(10):2299–2307 (1996) and sequenced on Model 470 and 477 (Applied Biosystems Inc., Foster City, Calif.). For sequencing, peptides were dried onto Biobrene-coated cartridge filters (Applied Biosystems Inc.) and the tube that contained the peptide was rinsed with 30 μl of trifluoracetic acid, which was also dried on top of the filter. For peptide synthesis, the solid phase strategy employing optimum side chain protection was used (Gozes et al., Proc. Natl. Acad. Sci. USA 93:42–432 (1996); Gozes et al., Endocrinology 134:2121–2125 (1994); Gozes et al., J. Pharmcol. Esp. Ther. 173:161–167 (1995)). Products were purified on Sephadex G-25 (Sigma Chemical Co., St. Louis, Mo.) and reverse-phase amino acids.

b. CNBr digestion: The protein was diluted in 70% formic acid. CNBr (5× in weight) was slowly dissolved in the dark in 70% formic acid. The digestion was carried out at room temperature, in the dark, with a CNBr:protein ratio of 1:1. After overnight incubation, the digested protein was concentrated using a speedvac with four sequential water washes. Peptides were thereafter separated by HPLC as described by Brenneman & Gozes (J. Clin. Invest. 97:2299–2307 (1996)).

The sequences obtained relate to the yeast/protein PIF1:

(a) PQLISEXSFXQ (SEQ ID NO:19) (X denotes unknown); and (b) IQLEXEIXEXQII (SEQ ID NO:20).

4. Antibodies to ADNF a. Preparation of antibodies: Antibodies were prepared in rabbits after fusion of the obtained sequence, i.e., the ADNF I/PIF1-related sequence (IQLETEIQEKQII, (SEQ ID NO:37)), to KLH. Similarly, antibodies were prepared in rabbits after fusion of the obtained sequences, i.e., the ADNF I/hsp60-related sequence (CVLGGGSALLRSIPA, (SEQ ID NO:21)), to KLH and also in a parallel experiment to BSA through a cysteine residue at the N-terminal. Affinity chromatography was performed on a sephadex column with conjugated CVLGGGSALLRSIPA (SEQ ID NO:21), or columns containing CSALLRSIPA (SEQ ID NO:12) (both conjugated through the cysteine residue). Antibodies against isolated ADNF III protein bands extracted from polyacrylamide gels were elicited in mice (Gozes et al., Developmental Brain Research 99:167–175 (1997); McManaman et al., J. Biol. Chem. 12:5890–5897 (1988)).

b. Purification of the antibodies for PIF1-related sequence: Precipitation of antibodies is commonly done with ammonium sulfate. 5 ml of the rabbit serum was taken and centrifuged at 3000×g for 30 min. The supernatant was then transformed to an appropriate tube and agitated gently. While the antibody solution was agitated gently, a 0.5 volume of saturated ammonium sulfate was added. After all the ammonium sulfate was added, the container was moved to 4° C. for an overnight incubation and then centrifuged at 3000×g for 30 minutes. The supernatant was then carefully removed and the above procedure repeated for a second time. The final precipitate was centrifuged at 10,000 rpm for 30 min. The supernatant was carefully removed and discarded and the pellet was drained well. The pellet was resuspended in 2.5 ml PBS. The antibody solution was transferred to dialysis tubes (previously boiled with 10 mM EDTA for 10 minutes, followed by 3 washes with water) and was dialyzed against 3 changes of PBS overnight for 2 days. The antibody solution was then centrifuged to remove any remaining debris.

c. Affinity purification of antibodies for hsp60-related sequence: The column was washed with 0.5 M NaCl in PBS followed by a PBS wash. The serum was added (10 ml to 1 ml resin) and allowed to incubate, with shaking for 16 hours at 4° C. The column was washed with 10 volumes of PBS, and then with PBS containing 0.5 M NaCl (until no material absorbing at $A_{260}$ is eluted). Elution of the antibodies was performed with 0.1 M glycine-HCl, pH 2.5. Eluted fractions were neutralized with 0.1 volumes of 2M Tris pH=8.0. Antibodies were first purified against VLGGGSALLRSIPA (SEQ ID NO:23) and then two types of affinities were separated on the SALLRSIPA (SEQ ID NO:5) column.

d. Dot blot: Further specificity studies were performed utilizing the hsp60 homolog peptide VLGGGCALLRCIPA (SEQ ID NO:24), and shorter peptides, i.e., VLGGG (SEQ ID NO:13) and LGGGS (SEQ ID NO:11), and the antibodies exhibited specificity to SALLRSIPA (SEQ ID NO:5). Specificity studies were also performed to distinguish between the SALLRSIPA-peptide (SEQ ID NO:5) and the IQLETEIQEKQII-peptide (SEQ ID NO:37).

5. Cloning Strategy

Expression library utilizing P19-, a mouse embryonic carcinoma cell line induced to differentiate into glia and neurons by retinoic acid and cloned utilizing Uni-Zap™ XR (Stratagene), was used. The original library was $2 \times 10^6$ plaque forming units (PFU) and $2 \times 10^{10}$ after the first amplification. Bacteria used for transformation were XLI-Blue. The Amersham (ECL) nonradioactive detection kit for antibodies was used to detect positive plaques. The cloning procedure was as follows: A single colony of the E. coli strain XLI-Blue was taken from media containing 12.5 mg/ml tetracycline and grown overnight at 37° C. in liquid LB media containing 12% maltose and 10 mM $MgSO_4$. The number of plates that were required to screen the entire library to obtain a positive clone was calculated to be 50, assuming $2 \times 10^4$ plaques per 90 mm plate. A hundred microliters of the bacterial mixture was aliquoted into 50 tubes. In each tube, 0.1 ml of the plating bacteria was mixed with 0.1 ml SM containing $2 \times 10^4$ PFU of the UniZAP XR expression library, and incubated for 20 min. at 37° C. Each tube then received a 3 ml of molten top agarose, and was immediately poured onto an LB agar plate. The infected plates were then incubated for 3.5 hours at 37° C. Nitrocellulose filters were numbered with ball-point pen, and were soaked in a solution of isopropylthio-β-D-galactoside (IPTG) (10 mM in distilled water) for a few minutes. Using blunt-ended forceps, the filters were removed from the solution, and allowed to dry at room temperature. The plates were removed from the incubator and quickly overlaid with the IPTG-impregnated nitrocellulose filters, and then incubated for 4 hours at 37° C. Following this incubation, the lids were removed from the plates and the incubation continued for an additional 20 minutes at 37° C., the plates were then moved to room temperature. Each of the filters were marked in at least three asymmetric location by stabbing through it and into the agar underneath with an 18-gauge needle attached to a syringe containing waterproof black ink. The filters were then peeled off the plates and immediately immersed in a large volume of TNT (10 mM Tris Cl (pH=8.0), 150 mM NaCl, 0.05% Tween 20). When all of the filters were removed and rinsed, they were transferred for an over-night incubation at 4° C. on a glass tray containing blocking buffer (7.5 ml for each filter of 10% low fat milk-1% in TNT) in order to block nonspecific binding. The filters were then transferred to a fresh glass tray containing the primary antibody (mentioned above). The antibodies were diluted :250–1000 in blocking buffer (7.5 ml for each filter), and after all of the filters were submerged, they were incubated overnight at 4° C. The filters were then washed 3 times in a fresh blocking buffer for 15 minutes each time at room temperature. The filters were then transferred to a fresh glass tray containing the secondary antibody (goat anti-rabbit IgG-Peroxidase Conjugate, Sigma Immuno Chemicals A-6154) diluted 1:30,000 in blocking buffer (7.5 ml for each filter). The filters were submerged and incubated for 1 hour at room temperature. The filters were then washed as described before. The Amersham (ECL) nonradioactive detection kit for antibodies was used to detect positive plaques. Each positive plaque that was identified was taken out of the agar using the large end of a Pasteur pipette and transferred to 1 ml SM (NaCl, 5.8 g/l; $MgSO_4$-$7H_2O$, 2 g/l 1M Tris-HCl, pH 7.5, 50 ml/l; 2% gelatin 5 ml/l) containing 2 drops of chloroform. The bacteriophage particles were then allowed to elute from the agar by over-night incubation at 4° C. The titer of the bacteriophage was determined and replating was performed at a 1000 plaques per 90 mm plate. The plaques were then re-screened and plated until a homogeneous population of the inmmunopositive recombinant bacteriophage was obtained.

6. Plasmid Preparation

To excise the pBluescript SK⁻ from the lambda ZAPII vector, the in vivo excision protocol using "ExAssist™ system (Stratagene) was employed. Experiments were performed according to the Company manual. The plaque of interest was taken out from the agar plate and transferred to a sterile microfuge tube containing 500 ml of SM buffer and 2 drops of chloroform. The tube was mixed to release the phage particles into the SM buffer, and incubated over-night at 4° C. In a 50 ml conical tube, the following was combined:

200 ml of O.D.$_{600}$=1.0 XLI-Blue cells 100 ml of phage stock (containing >1×10⁵ phage particles)

1 ml of ExAssist helper phage (>1×10⁶ PFU/ml)

The mixture was then incubated at 37° C. for 15 minutes. To the above mixture, 5 ml of 2XYT (bacto-tryptone 16 g/l, bacto yeast extract 10 g/l, NaCl 5 g/l) media was added and incubated for 2–2.5 hours at 37° C. with shaking. The tubes were then heated at 70° C. for 20 minutes and centrifuged for 5 minutes at 4000×g. The resulting supernatants were decanted into sterile tubes and stored at 4° C. In order to plate the rescued phagemid, 200 ml of XLI-Blue cells were added to 2 tubes. 10 ml of the phage stock was added to one tube and 20 ml of 1:100 dilution from the phage stock was added to the other tube. The tubes were then incubated at 37° C. for 15 minutes. Then, 100 ml from each tube were plated on LB-ampicillin plates (100 mg/ml) and incubated overnight at 37° C. Colonies that appeared on the plate contained the double stranded pBluescript SK⁻ phagemid with the cloned DNA insert of p25 (ADNF III). A single colony was then taken from the plate and grown overnight at 57° C. in a liquid LB media containing 100 mg/ml ampicillin. The overnight culture of *E. coli* was then subjected to Wizard Midi-prep DNA Purification System (Promega). The purified DNA was eluted from the Midi-prep column in water free of any salt or macromolecular contaminants. The purified plasmid was then used directly for DNA sequencing.

7. Expression for Functional Cloning

*E. coli* carrying the plasmid clone were grown to O.D.$_{600}$=0.2, followed by incubation with IPTG (1 mM) until O.D.$_{600}$=1.0 was obtained. A bacterial pellet (1500×g, 15 min.) was resuspended in 4 M guanidine HCl; 100 mM KCl; 50 mM Tris, pH 8.0; 1 mM EDTA; 12.5 mM $MgCl_2$; 0.1% NP-40; and a mixture of protease inhibitors: phenyl-methyl-sulfonyl-fluoride, aprotonin, leupeptin. The procedure further entailed sonication on ice 2 times each for 10 sec., shaking for 30 min. at 4° C., spinning at 27,000×g at 4° C., followed by aliquoting and storage at −8° C.

8. Biological Activity

Biological activity was tested in cerebral cortical cultures as before (see, e.g., Gozes et al., *Proc. Natl. Acad. Sci. USA* 93:427–432 (1996)). After nine days in vitro, the cultures were given a complete change of medium and treated with either 1 mM tetrodotoxin or with 25 mM β-amyloid peptide (25–35) and varying concentrations of fractionated protein isolated from *E. coli* carrying the plasmid containing the insert of p25 (ADNF III) and one that does not carry the insert, for an additional five days. Neuronal cell counts were conducted after immunocytochemical identification with antisera against neuron specific enolase. Counts were made in 10 fields from predetermined coordinate locations without knowledge of the treatment group.

9. Sequencing

Direct sequencing was performed utilizing automated DNA sequencing (Applied Biosystems). For complete sequence, either the synthetic oligodeoxynucleotides or the kit Erase a Base, which generates multiple fragments with shared sequences, was used. Starting with double digest of 10 mg of closed circular DNA with 2 different restriction enzymes: Apa I, which generates a 4-base 3' protrusion protecting the primer binding site because they are resistant to Exonuclease III (ExoIII) digestion, and Xho I, which leaves a 5' protrusion adjacent to the insert from which deletions are to proceed. The uniform rate of digestion of ExoIII allows deletions of predetermined lengths to be made simply by removing timed aliquots from the reaction (25 time points at 32° C. every 1 minute). Samples of the ExoIII digestion were removed at timed intervals and added to tubes containing S1 nuclease which removes the remaining single-stranded tails. After neutralization and heat activation of the S1 nuclease, Klenow DNA polymerase was added to flush the ends, which are then ligated to circularize the deletion-containing vectors. The ligation mixture was used directly to transform competent cells. Each successive time point yields a collection of subclones containing clustered deletions extending further into the original insert. A number of subclones from each time point were then screened to select for appropriate intervals between deletions. Sequence analysis was performed with T7 promoter primer.

10. Motif Determination

Determination of motifs in the new DNA sequence was performed using the GCG programs (Wisconsin Package Version 8.1 UNIX, August 1995, in the search used, only one mismatch was allowed).

11. RNA Isolation

RNA was prepared from astrocytes and neuroblstoma cells following a three hour treatment with 0.1 nM VIP in PBS at room temperature (as used for preparation of conditioned medium containing secreted ADNF (see Brenneman & Gozes, *J. Clin. Invest.* 97:2299–2237 (1996)). RNA was also prepared from fibroblasts obtained from the meninges of the newborn rats, as well as from mouse brain cortex, cerebellum, hind brain, kidney, spleen, lung and intestinal tract. RNA was isolated through the use of RNA NOW™ (Biological Industries Co. Beit-Haemek (1990) LTD). Quantification of RNA was performed by absorbance measurements at 260–280 nm.

12. Northern Blot Hybridization a. Gel electrophoresis: Similar amount of denatured RNA (10–30 mg) were separated by 1% agarose (SeKeam, FMC) gel electrophoresis, followed by blotting onto nitrocellulose membrane (Schleicher & Schuell) over-night (see Gozes, *Basic Principles of Gene Expression*, ETP/ENA/IBRO, Practical Course on Molecular Neuroanatomy pp. 35–55 (Van Leeuwen et al., eds. 1987); and also *Techniques and Behavioral and Neural Sciences Series* pp. 3–24 (Huston ed., 1989)). The membrane was cross-linked by exposure to short-wave UV radiation (12000 mJ/cm2).

b. Hybridization: The blots were prehybridized for two hours at 55° C. and were hybridized with a specific complementary DNA probe for the mouse ADNF III cDNA (a PCR product obtained using the following primers: 61–79 and the complementary strand from position 438–455, which are described in detail below). The labeled probe was prepared by random priming and incubated with the blot for 16 hours at 55° C. Prehybridization and hybridization solutions (12 ml/blot) contained the following: 50% formamide (deionized using mixed bed resin, Sigma), 50 mM sodium phosphate buffer (pH 6.5), 0.8 M NaCl, 1 mM EDTA, 5×Denhart's reagent (0.05% BSA, 0.05% polyvinylpyrrolidone and 0.05% Ficoll), 0.1% SDS and 200 mg/ml poly(A). The labeled probe was dissolved in 12 ml of hybridization solution and added to the prehybridization mixture. After hybridization the blot was washed in 2×SSC (20×SSC=3 M NaCl, 0.3 M trisodium citrate) and 0.1% SDS for 30 minutes, at 65° C. and exposed to Kodak XAR5 film for 16–20 hours at −70° C. using Du Pont Cronex intensifying screens.

13. Polymerase Chain Reaction (PCR)

The primers used for amplification of ADNF III cDNA were as follows:

for sense primer:

5' TCCAATGTTCACCTGCAG 3' (SEQ ID NO:7); and for antisense primer:

5' GCTCGTTACAGATTGTAC 3' (SEQ ID NO;8), which correspond to base pairs 61–79 and 438–455, respectively, for the mouse ADNF III cDNA. The PCR product was derived from the pBluescript SK⁻ double stranded phagemid with the cloned DNA insert of p25 (ADNF III). Methods were carried out according to text book methods described in molecular biology (see, e.g., Sambrook, J., et al., *Molecular Cloning, A Laboratory Manual* (2nd ed. 1989). Thirty five PCR cycles (1 min at 94° C., 1 min at 56° C., 1 min at 72° C.) were performed. 10 ml of each PCR product was subjected to electrophoresis on a 1.5% TAE agarose gel stained with ethidium bromide and visualized under U.V. light.

14. Recovery of DNA 90 ml of each PCR product was submitted to electrophoresis on a 1.5% TAE agarose gel stained with ethidium bromide and visualized under U.V. light. The corresponding band was sliced from the agarose gel and subjected to GenElute™ Agarose Spin Columns (Supelco).

15. Labeled DNA Probes 25 ng of template DNA eluted from the agarose gel was labeled in a random priming reaction using the NEBlot Kit (New England BioLabs) and a $^{32}$P dCTP (3,000 Ci/mmol, 50 mCi). The labeled DNA was then subjected to NICK Columns (Pharmacia Biotech) for separation of unincorporated $^{32}$P-labeled nucleotides.

16. RT-PCR cDNA was obtained by reverse transcription of 2 mg of total RNA with the MLV Reverse Transcriptase from Gibco-BRL (LifeTechnologies) according to the manufacturer's protocol. The cDNA was then used for polymerase chain reaction (PCR) using the AmpliTaq DNA Polymerase (Perkin Elmer) according to the manufacturer's instruction. The primers used for amplification of ADNF III cDNA were the same as those described in the PCR section, supra. As a negative control, RNA was prepared from fibroblasts in sister cultures to the astrocytes used above prepared from the meninges of the newborn rats.

17. SDS-Polyacrylamide Gel Electrophoresis a. Gel electrophoresis: Condition medium from astrocytes treated with VIP was subjected to electrophoresis through 10% polyacrylamide (BioRad) slab gel containing 0.1% SDS. The sample was mixed with 1:1 volume of 2× SDS gel loading buffer (100 mM Tris Cl (pH 6.8), 200 mM dithiothreitol, 4% SDS (electrophoresis grade), 0.2% bromophenol blue, 20% glycerol, 200 mM Dithiothreitol). Molecular weight determinations were obtained by the parallel analysis of molecular weight markers (Sigma).

b. Coomassie Brilliant Blue stain: Coomassie Brilliant Blue stain was performed using standard conditions on SDS 10% polyacrylamide gel electrophoresis (Sambrook et al., *Molecular Cloning, A Laboratory Manual* (2nd ed. 1989).

c. Western blot hybridization: Western blot was performed using standard conditions on SDS 10% polyacrylamide gel electrophoresis (Sambrook et al., *Molecular Cloning, A Laboratory Manual* (2nd ed. 1989) with antibodies prepared against VLGGGSALLRSIPA (SEQ ID NO:23), elicited in rabbits as indicated above and purified over affinity columns containing SALLRSIPA (SEQ ID NO:5) as the binding ligand. Affinity purified antibodies were calibrated for the right dilution, and the one used for the experiment was 1:250.

18. Mimic, Polymerase Chain Reaction

Using the primers: 5', position 71 (20 mer) Td=59.3; 5' ACCTGCAGCAAAACAACTAT 3' (SEQ ID NO:9); and 3' primer, position 423 (23 mer) and a mimic product (starting from position 1165, small letter) containing the 5' primer as well: 5' ACCTGCAGCAAAACAACTATtTTCCATC-CCTCAACAGT 5' (SEQ ID NO:25), this mimic, hybrid primer when used results in a deletion product containing the same 5' as the cDNA, but missing a stretch of bases at positions 90–165. The deletion product is prepared in large quantity and used as a standard for the PCR reaction allowing relative quantitation. In addition, cyclophilin mRNA (upper primer: position, 348: 5' ATGGCACAG-CAGGAAAGAGC 3' (SEQ ID NO:26), lower primer: 5' TTGCCGGAGTCGACAATGAT 3' (SEQ ID NO:27) giving a product of 279 bases and the mimic primer: 5' ATGGCA-CAGGAGGAAAGAGCAATGCAGGCAAAGACACC 3' (SEQ ID NO:38) was quantitated and the results are depicted as the ratio with cyclophilin mRNA quantified in the same samples in the same manner. The expression is determined in embryos, 9.5-day-old mouse embryos incubated in vitro for four hours as before (Gressens et al., *Nature* 362:155–158 (1993)).

19. Peptide Synthesis

For peptide synthesis, the solid phase strategy employing optimum side chain protection was used (Gozes et al., *Proc. Natl. Acad. Sci. USA* 93:427–432 (1996); Gozes et al.,

*Endocrinology* 134:2121–2125 (1994); Gozes et al., *J. Pharmacol. Exp. Ther.* 173:161–167 (1995)). Products were purified on Sephadex G-25 (Sigma Chemical Co., St. Louis, Mo.) and reverse-phase amino acids.

20. Learning and Memory

Protection against learning and memory deficiencies associated with cholinergic blockade was evaluated. Cholinergic blockade was obtained in rats by administration of the cholinotoxin AF64A, NAPVSIPQ (SEQ ID NO:6), which was administered intranasally and the water maze experiments were performed as before (Gozes et al., *Proc. Natl. Acad. Sci. USA* 93:427–432 (1996), the teachings of which are incorporated herein by reference).

ChAT activity was measured according to published procedures (Fonnum et al., *Neurochem.* 24:407–409 (1975)). Brains were homogenized with 10 volumes of 50 mM phosphate buffer containing 300 mM NaCl, 20 mM EDTA, and 0.5% triton. The homogenates were centrifuged at 12,000×g for 15 min., and 10 ml of supernatant was mixed with 10 ml of a solution of 14 M $^{14}$C-acetyl CoA (56 mCi/nmol NEN), 20 mM acetylcholine, 1.6 mM choline chloride, 0.25 mM eserine, and phosphate buffer. Incubation was 15 min. at 37° C. The reaction was terminated and radioactivity was measured in a beta-counter.

21. Apolipoprotein E (ApoE) Deficient Mouse Model

ApoE knockout mice and normal controls were a gift from the late Prof. Shlomo Eisenberg of Tel Aviv University, originally provided by Dr. J. L. Breslow (Plump et al., *Cell* 71:343–353 (1992)). The ApoE knockout mice were obtained from embryonic stem cells OLA 129 in C57B6× FVB mice (as described). Age-matched controls were inbred C57B6 mice. Groups of mouse pups were treated from birth until the age of 14 days. Daily subcutaneous injections included: 20 ml saline (days 1 through 4), 40 ml saline (days 5 through 10) and 80 ml saline (days 11–14). Peptides (synthesized as before; Gozes et al., *J. Neurobiol.* 33:329–342 (1997); Gozes & Brenneman, *J. Molec. Neurosci.* 7:235–244 (1996)) were dissolved to a final concentration of 25 (g/ml before administration. To obtain homogeneous solutions of peptides, initial solubilization was performed in dimethyl sulfoxide (DMSO, 1 mg/30 ml) followed by serial dilutions in saline. Control animals received saline. The vehicle (DMSO diluted in saline) did not have any effect, and results obtained with those were similar to the results obtained with saline alone.

Developmental milestones were measured using at least three dams with 5–8 pups each for every experimental point. All observations were made between 12 noon and 4 pm. From day one through day six, mice were weighed and tested 60 min. after the daily injection. Placing is a behavioral parameter that is measured as the time elapsing between contact of the foot against the edge of an object and its placing on the top of the same object.

22. Statistical Analysis

ANOVA with Student-Neuman-Kuel's multiple comparison of means test was used to assess the results.

B. RESULTS

A cDNA expression library from P19- a mouse embryonic carcinoma cell line induced to differentiate into glia and neurons by retinoic acid (in Uni-Zap™ XR (Stratagene)) was screened for ADNF III expression. Two types of antibody were used, one against SALLRSIPA-BSA (SEQ ID NO:36) and one against PIF1, both of which are described supra. After obtaining 9 immunopositive recombinant bacteriophages with the antibodies against SALLRSIPA (SEQ ID NO:5), the next step determine whether one of these bacterio-phages would react with antibodies prepared against PIF1. The plaques were then replated on 9 different plates and further subjected to the same procedure with anti-PIF1 antibodies. At this stage, only one of the 9 different plaques gave a positive result and it was assigned the name "p25". The p25 DNA fragment cloned into the pBluescript SK was about 3 kb in length and was thus too long to sequence conveniently from a single primer binding site on the vector. An efficient way to sequence such a large DNA insert was to generate a nested set of deletions in the target DNA, effectively moving the priming site closer to the sequence of interest. The complete sequence of mouse ADNF III was thus obtained. The cDNA contains 2418 base pairs of open reading frame encoding 806 amino acids, pI: 5.85 (FIG. 1). Similarities between hsp60 and PIF1 to ADNF III are also set forth in FIG. 1.

The determination of motifs in the new DNA sequence was performed using the GCG programs showing presence of many conserved motifs in the most 5' region. It should be noted that this is the region containing the sequence of the active NAPVSIPQ-peptide (SEQ ID NO:6), which is discussed in detail hereinbelow. The motifs include the ABC transporters family signature: ATP-binding proteins involved in active transport of small hydrophilic molecules across the cytoplasmic membrane; ATP/GTP-binding site motif A (P-loop); and aldehyde dehydrogenase active site.

A nine amino acid sequence of the p25 clone (GGNAPVSIP, SEQ ID NO:28) exhibited a limited structural similarity to an active peptide of ADNF I (VLGGGSALLRSIPA, SEQ ID NO:23) and to the homologous region in hsp60 (VLGGGCALLRCIPA, SEQ ID NO:24) with 77.8% underlying nucleic acid identity with rat hsp60 and 70.4% identity with mouse hsp60 (Peralta et al., *Nucleic Acid Res.* 18:7162 (1994); Venner & Gupta, *Biochem Biophys. Acta* 1087:336–338 (1990)). Limited structural similarity was observed with PIF1 as well (FIG. 1). Further comparative sequence analysis revealed a zinc finger domain (FIG. 1 bold) (Rosenfeld & Margalit, *J. Biomol. Struct. Dyn.* 11:557–570 (1993)). Within this sequence, an homology to the active site of glutaredoxin (a thiol transferase) was also observed[20]. Overall analysis utilizing the Chou-Fasman prediction (Chou & Fasman, *Adv. Enymology* 47:45–148 (1978)) indicated that the protein was a flexible hydrophilic molecule with multiple antigenic sites and mixed alpha helices and beta sheets. Nine potential glycosylation sites suggested a protein that was membrane associated or secreted. The hydrophilic nature was consistent with a secreted protein. A putative signal peptide of 18 amino acids comprising hydrophobic, polar and basic amino acids without acidic groups was identified at the N-terminal of the molecule (net charge +2). The long stretch of glutamic acid residues at the C-terminal region of the molecule (FIG. 1) could mediate interactions with extracellular basic molecules, such as polyamines, or serve as a site for proteolytic cleavage (Chang et al., *J. Biol. Chem.* 262:11901–11903 (1987); Chestukhin et al., *J. Biol. Chem.* 272:3153–3160 (1997)). Other potential processing sites found were dibasic residues, commonly associated with neuropeptide cleavage, notably KKRK (SEQ ID NO:39) (amino acids 425–428) and KRKK (SEQ ID NO:40) (amino acids 504–507). Sequences containing abundant prolines, glycines, leucines, glutamines, alanines and serines were observed at the N-terminal portion of the protein, suggesting macromolecular interactions (Taira et al., *Dev. Biol.* 159:245–256 (1993)). Additional mouse and human clones and their characteristics are shown in FIGS. 11–13. The sequence of the mouse promoter is shown in FIG. 14.

The following steps were performed in an attempt to obtain as much data as possible regarding the characterization of ADNF III. First, the mRNA was identified in rat astrocytes by the RT-PCR technology. Astrocytes were treated for three hours with 0.1 nM VIP in PBS at room temperature (as used for preparation of conditioned medium containing secreted ADNF (see Brenneman & Gozes, *J. Clin. Invest.* 97:2299–2237 (1996)). PCR amplification was performed as described supra. As a negative control, RNA was prepared from fibroblasts in sister cultures to the astrocytes used above prepared from the meninges of newborn rats. FIG. 2 depicts agarose (2%) gel electrophoresis stained with ethidium bromide of: M=DNA size markers, 1. PCR product derived from fibroblasts RNA, 2. PCR product derived from astrocyte RNA. The size of the full length RNA transcript in northern blot hybridization was about 5300±200 base-pairs, suggesting a long poly (A) tail. The mRNA was identified in astrocytes as well as in the brain, including cortex, cerebellum, hippocampus, frontal lobe, medulla oblongata, subthalamic nucleus and the hind brain as well as the spinal cord. mRNA expression was also observed in fetal tissue, especially the lung, and in endocrine tissue. Low amounts were detectable in the kidney, spleen, and lung (see, e.g., FIG. 15).

Figure 3:
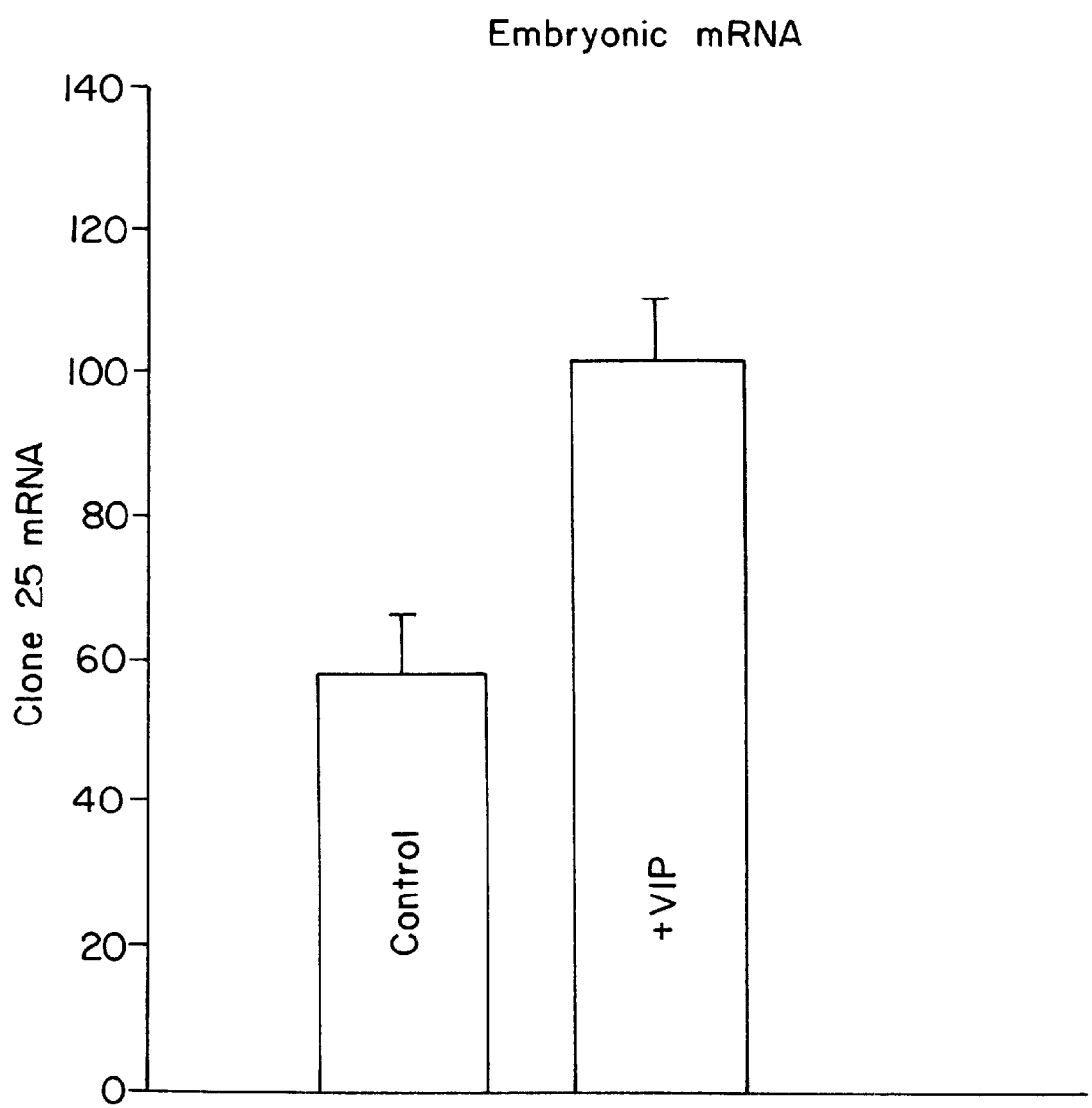
FIG. 3 shows the results of the mimic polymerase chain reaction. The mRNA expression is determined in embryos, 9.5-day-old mouse embryos incubated in vitro for four hours as before (Gressens et al., Nature 362:155–158 (1993)). Results show about a two-fold increase in ADNF III mRNA following VIP treatment, as determined by examining PCR product. In situ hybridization experiments localized the expression to the developing nervous system of the mouse embryo (not shown).

FIG. 3 shows mimic, polymerase chain reaction. The expression is determined in embryos, 9.5-day-old mouse embryos incubated in vitro for four hours as before (Gressens et al., *Nature*, 362:155–158 (1993)). Results show about a two-fold increase in ADNF III mRNA following VIP treatment. Student t-test indicated a significant difference upon VIP treatment (P<0.0096). In situ hybridization experiments localized the expression to the developing nervous system of the mouse embryo.

Figure 4A:
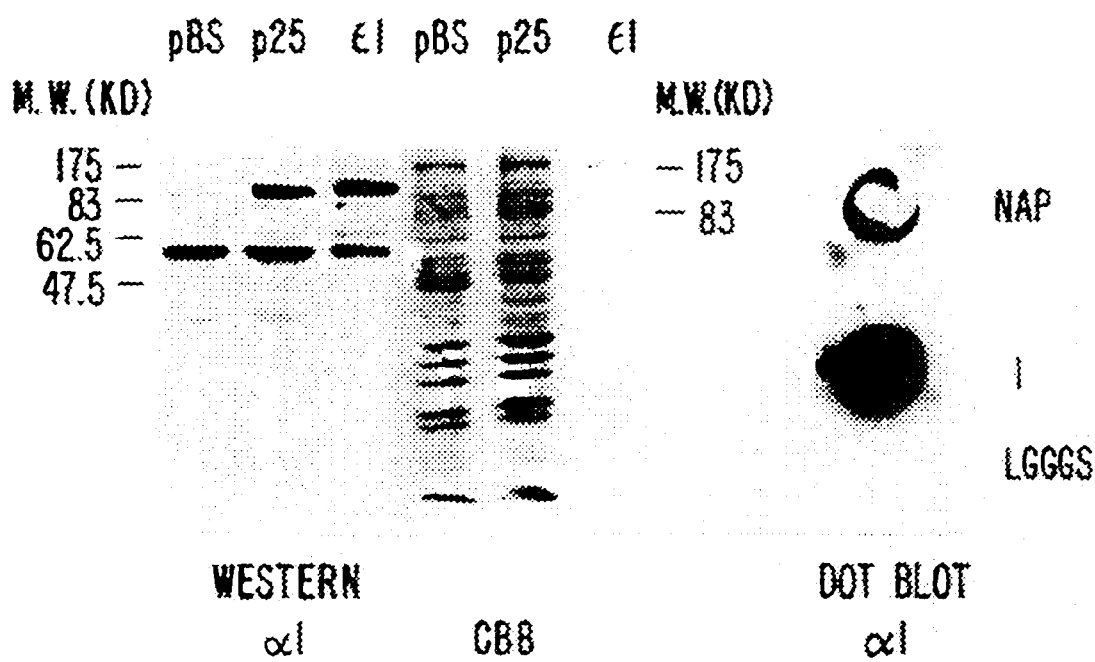
FIGS. 4A–B.

Clone 25 gene expression was enriched astrocytes as compared to fibroblasts (FIG. 2). To investigate astrocyte-secretion of the new protein, western blot analyses were performed. The first antibody (α1), detected the antigen SALLRSIPA (SEQ ID NO:5) and NAPVSIPQ (SEQ ID NO:6) (NAP, clone 25 sequence) but not LGGGS (SEQ ID NO:11), the hsp60-derived part of the antigen (FIG. 4A, dot blot). This antibody specifically identified the bacterially expressed clone 25 protein by western blotting (~89 KD, FIG. 4A, p25). Transformed bacterial extract not containing the cloned insert was used as a negative control (FIG. 4A, pBS). An additional protein band (~60 KD) was identified by the antibody, in both p25 and pBS. Partial purification (15-fold) of the cloned β-galactosidase-fusion protein was achieved by chromatography on a p-aminobenzyl 1-thio-β-D-galactopyranoside affinity column (FIG. 4A, E1), resulting in an enriched protein that exhibited the same immuno-specificity as the original bacterial extract. Thus, the 60 KD protein band may represent both a breakdown product of ADNF III, as well as a bacterial homologue. Increased expression (several fold) of both the ~89 KD and the ~60 KD proteins was obtained following isopropyl-β-D-thiogalactopyranoside (IPTG) induction in clone 25.

Figure 4B:
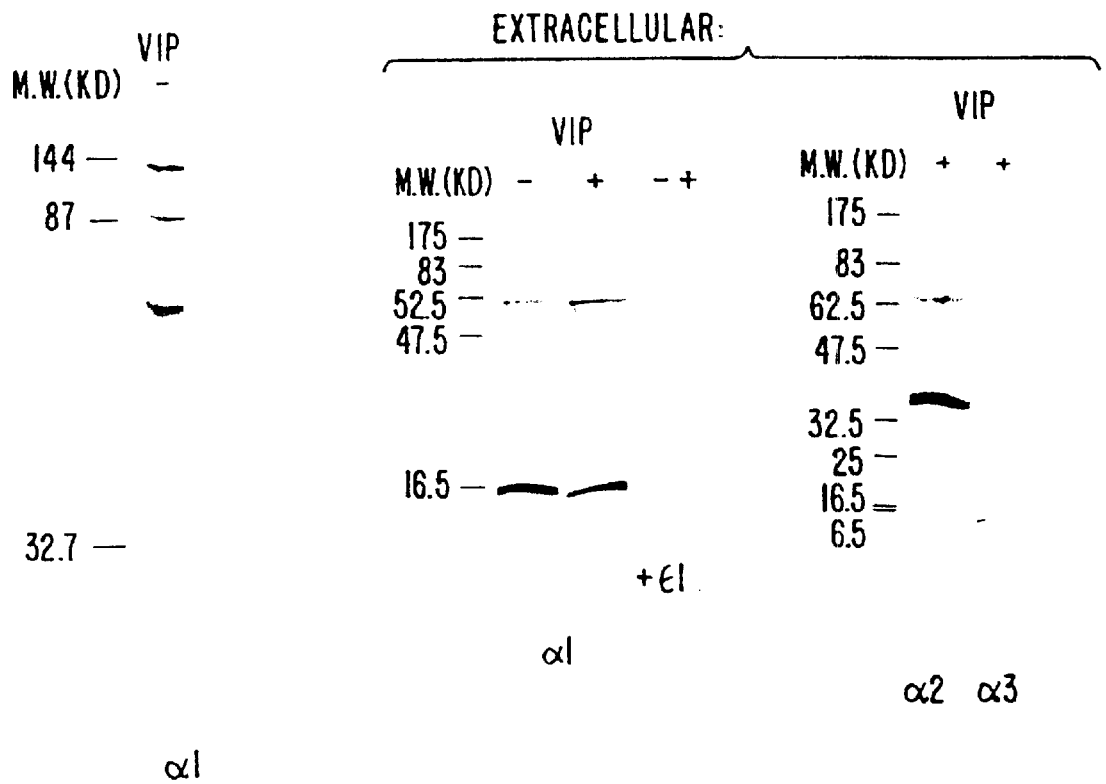

The same 89 KD and the 60 KD-immunoreactive proteins (ADNF III) were extracted from the polyacrylamide gel and injected into mice for anti-ADNF III antibody preparation (α2 and α3, respectively). All three antibodies (α1, α2 and α3), recognized protein bands at the 60 KD range in the extracellular milieu of astrocytes (FIG. 4B). The antibody a1 recognized an additional ~14 KD protein (the putative ADNF I) and α2 (prepared against the ~89 KD clone 25 protein) recognized also a ~37 KD protein, which may represent a breakdown product. The specificity of α1 was further determined by competing the antibody binding with the enriched clone 25 protein (E1, FIG. 4B). Cellular viability was ascertained by measurements of lactic dehydrogenase. Overall, the results suggest post-translational processing to secreted forms of the protein. Intracellular astrocyte-derived immunoreactive material included higher molecular weight bands (FIG. 4B) with an 89 KD band, representing the putative ADNF III holoprotein, an 144 KD band, a putative post-translationally modified form, and the ~60 KD putative secreted form. An apparent increase (up to 2-fold) in the secreted 60 KD ADNF-like immunoreactivity was observed in the presence of VIP.

Figure 5A:
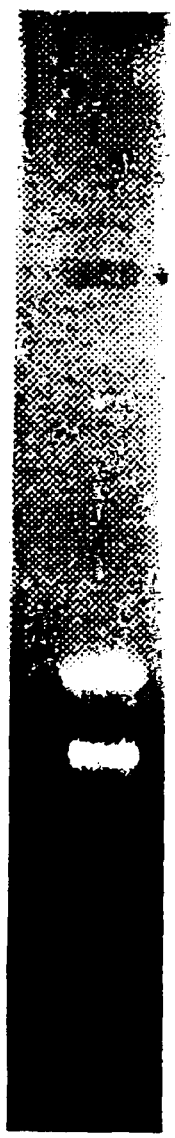

FIG. 5A illustrates PCR of cDNA from human neuroblastoma (Lilling et al., *J. Molec. Neurosci.* 5:231–239 (1995)). The primers utilized were bases 71–90 (sense): ACCTG-CAGCAAAACAACTAT (SEQ ID NO:9); and bases 438–455 (antisense) 5' GCTCGTTACAGATTGTAC 3' (SEQ ID NO:8). The correct expected size of the product (similar to that expected in mice) is shown (see FIG. 5B). Human material expresses the ADNF III mRNA and sequence analysis revealed 87% similarity at the nucleotide level and 93% similarity and 92% identity at the amino acid level to the mouse cDNA (see FIG. 5C).

Figure 6A:
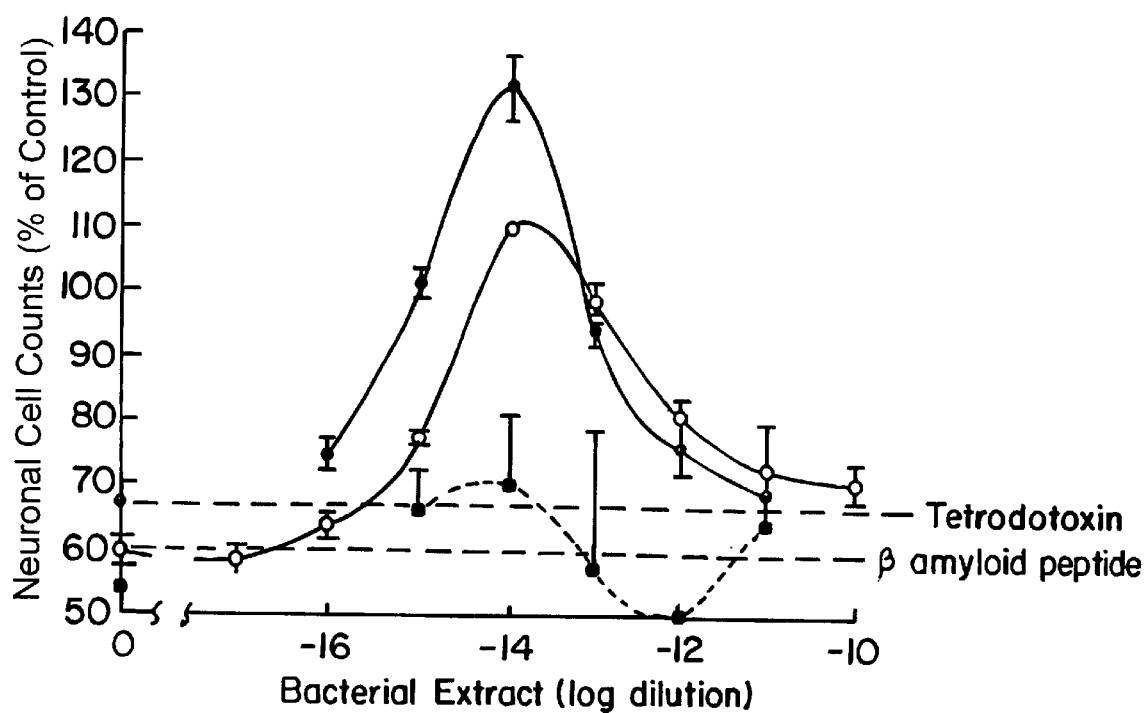
FIGS. 6A–C illustrate that bacterial extract from bacteria expressing clone 25 (the "expressed protein") provides neuroprotection in a variety of settings.

Biological activity of the "expressed protein" was assessed in cerebral cortical cultures derived from newborn rats (Gozes et al., *Proc. Natl. Acad. Sci. USA* 93:427–432 (1996)) using two neurotoxins: 1. tetrodotoxin, a blocker of electrical activity, enhancing apoptosis in 30–50% of the neurons including the cholinergic population; 2. the β-amyloid peptide, an Alzheimer's disease-associated toxin, providing a 50–70% reduction in neuronal cell counts. Neuroprotection against the two toxins (FIG. 6A) was obtained at extremely high dilutions ($10^{-14}$ P<0.0001) of a 1 mg/ml *E. coli* protein extract, containing expressed clone p25. Similar neuroprotection was obtained with the isolated immunoreactive protein bands (87 KD and 60 KD in p25, FIG. 4A). The bell shaped dose response, with an abrupt decline at increasing concentrations, is a pharmacological response of growth factors and neuropeptides in a wide variety of tissues. The cell counts totaled over a 100% of control because the treatment prevented neuronal cell death that occur naturally in the cultures. A control extract from a phagemid lacking an insert (pBS) was not neuroprotective (FIG. 6A, closed squares).

Figure 6B:
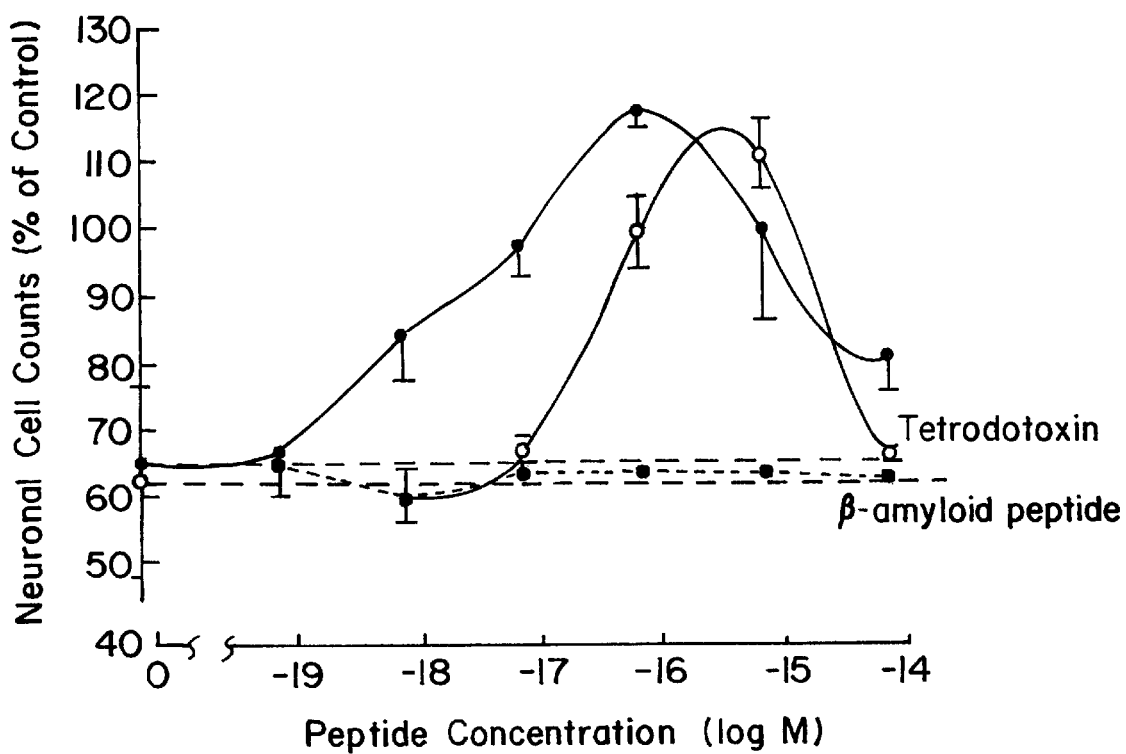

Previous results with ADNF I identified a femtomolar-acting neuroprotective peptide of 14 amino acids. As NAPV-SIPQ (SEQ ID NO:6) (NAP or ADNF III-8) from ADNF III exhibited structural and immunological similarity to the active ADNF I peptide (FIG. 1 and FIG. 4A) it was further tested for biological activity. NAP mimicked the activity of the entire protein, in providing protection against neurotoxicity associated with the β-amyloid peptide and against electrical blockade (FIG. 6B). A control peptide was inactive (FIG. 6B, closed squares). Thus, not all the ADNP structure is required for neuroprotection.

Figure 6C:
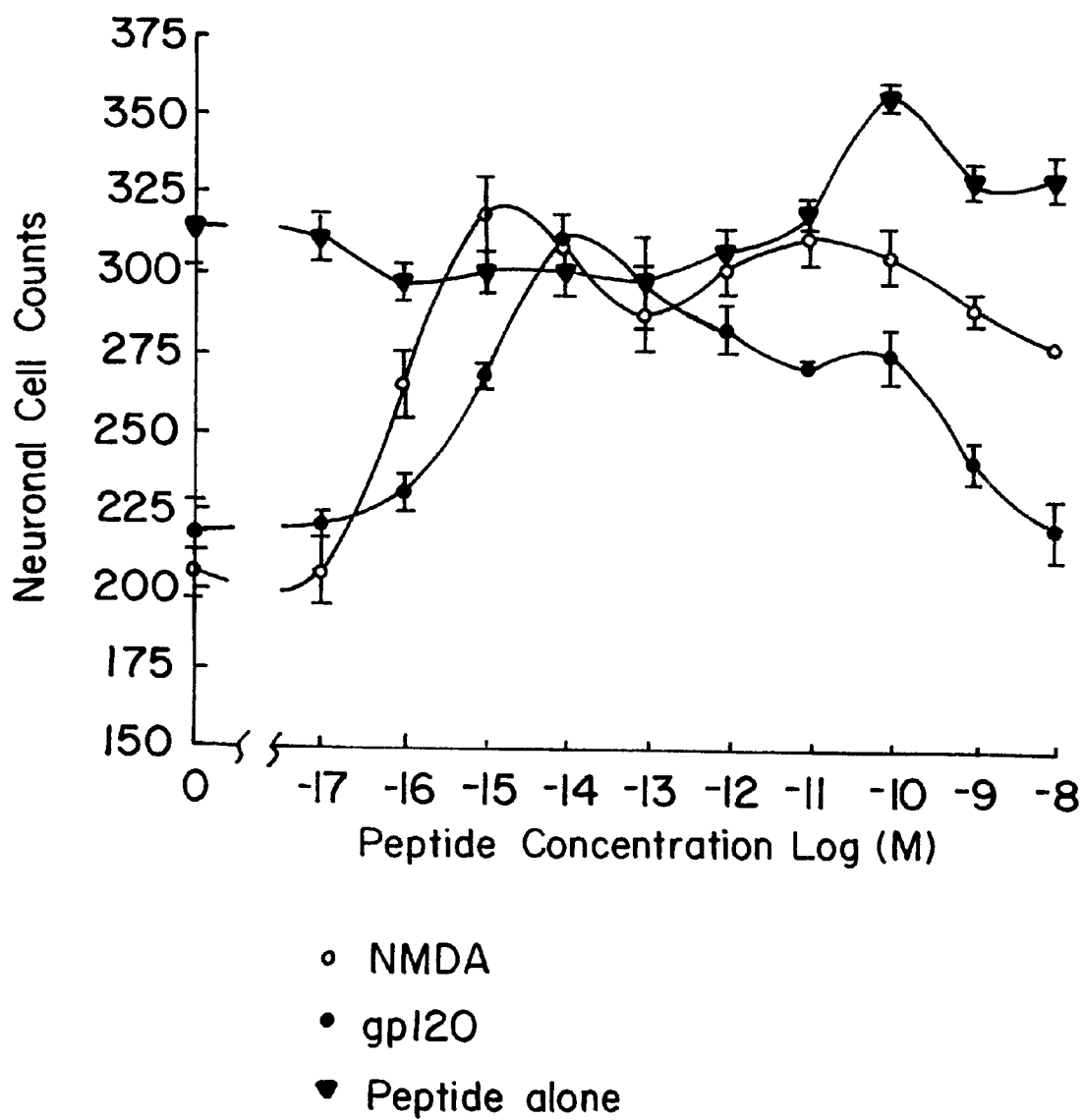

Considerable breadth of activity was evident in that NAP also protected neurons against toxicity associated with gp120, the envelope protein from the human immunodeficiency virus, from N-methyl D-aspartate (NMDA) and from naturally occurring cell death (FIG. 6C). The range of neuroprotective concentrations against NMDA was $10^{-16}$M to $10^{-8}$M, unusually wide limits of efficacy. Furthermore, as NMDA-associated toxicity may be a common pathway underlying neuronal death from many causes (Lipton et al., *Neuron* 7:111–118 (1991)), a broad application for NAP in neuroprotection is inferred.

Figure 7A:
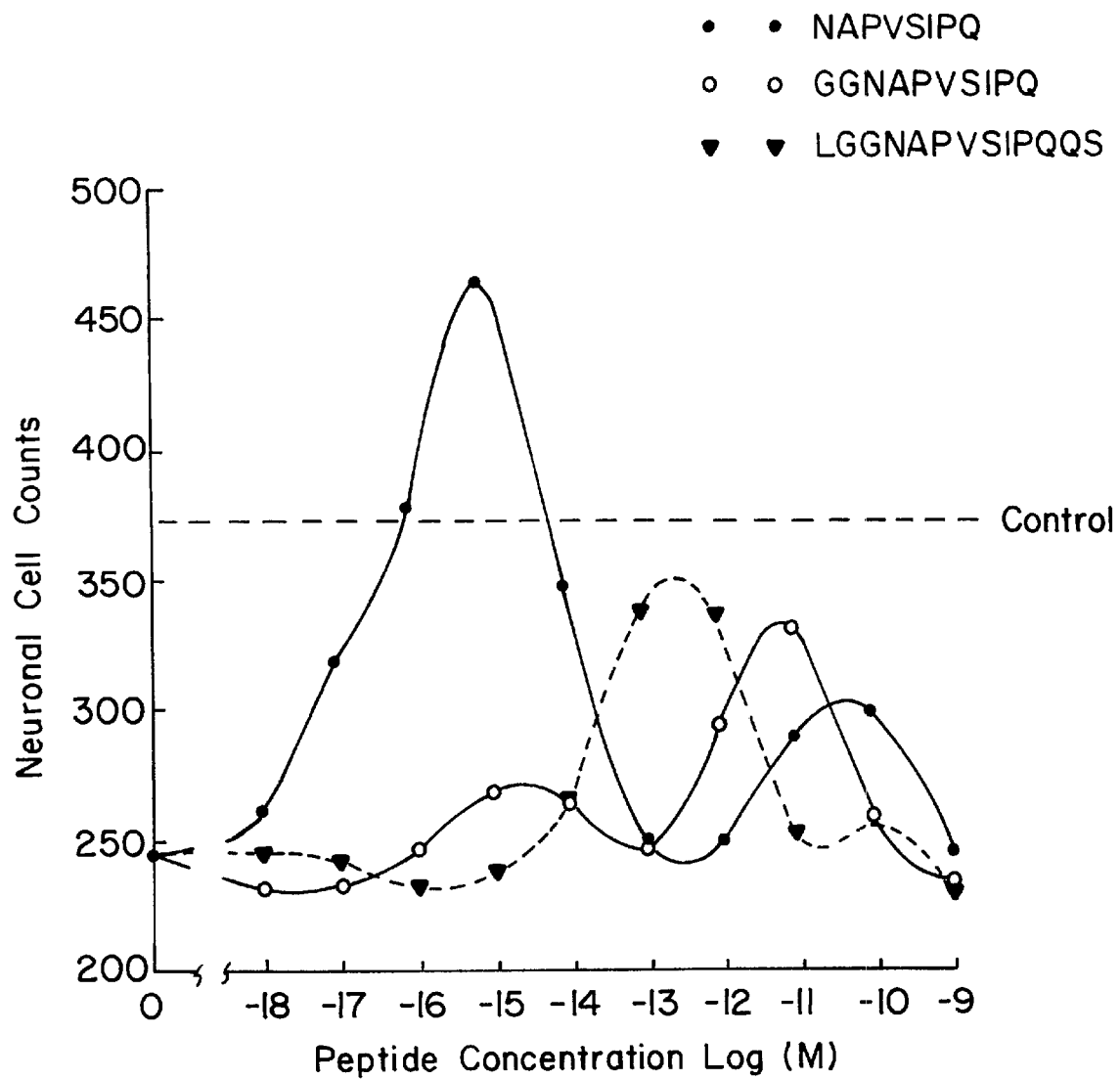
FIGS. 7A and 7B depict structure-activity studies and identify NAPVSIPQ (SEQ ID NO:6) as the most active peptide, exhibiting two peak optimum concentrations, i.e., $10^{-16}$–$10^{-14}$ M and $10^{-11}$–$10^{-10}$ M (GGNAPVSIPQ=SEQ ID NO:33; LGGNAPVSIPQQS=SEQ ID NO:34; SVRLGLGGNAPVSIPQQS=SEQ ID NO:12; LGLGGNAPVSIPQQS=SEQ ID NO:35).
Figure 7B:
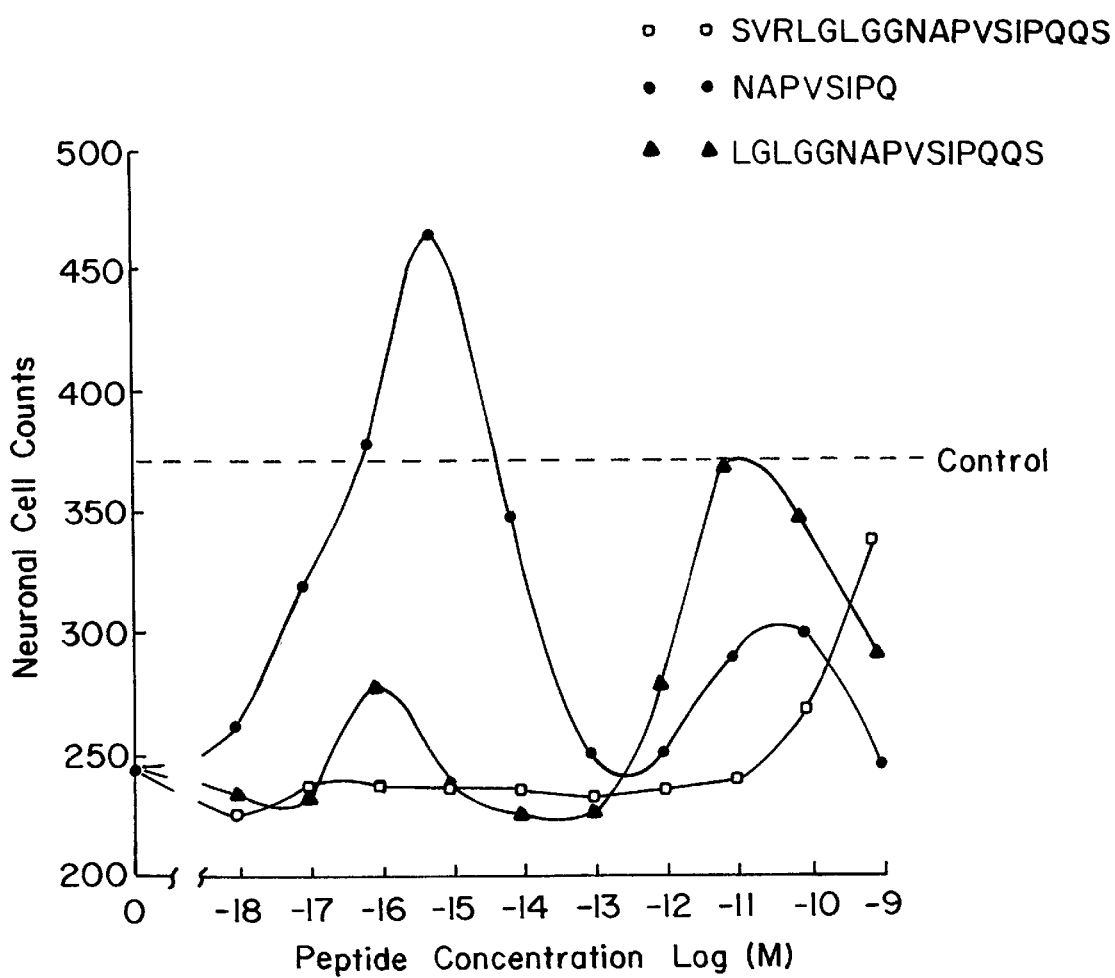

FIGS. 7A and 7B depict structure-activity studies and identify NAPVSIPQ (SEQ ID NO:6) as the most active peptide, again exhibiting two peak optimum concentrations, i.e., $10^{-16}-10^{-14}$ M and $10^{-11}10^{10-1}$ M. Amino acid additions at either side of the peptide rendered the peptide less active, although still useful as a neuroprotectant protein.

Figure 8:
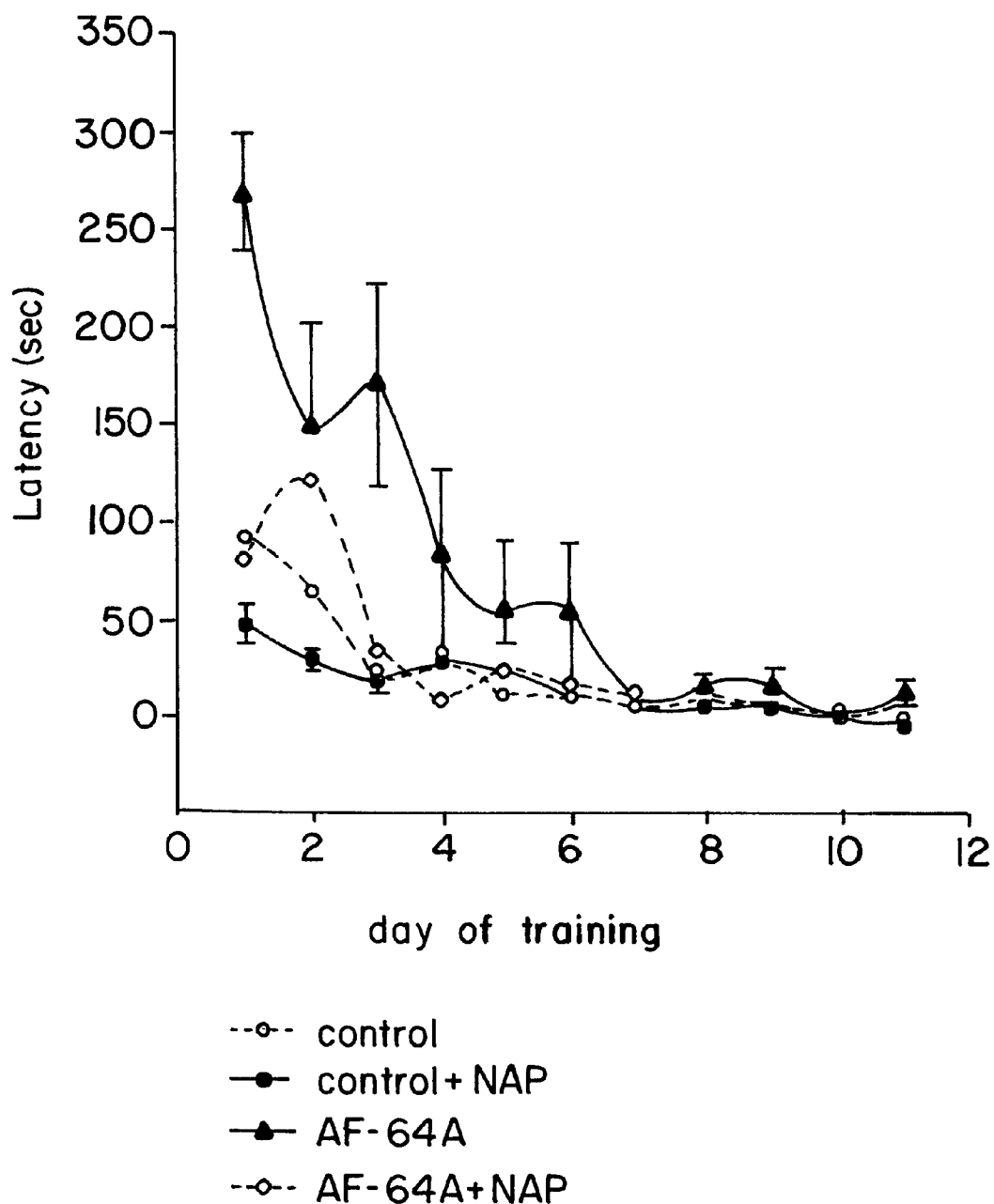
FIG. 8 illustrates the effects of NAPVSIPQ (SEQ ID NO:6) ("NAP") on learning and memory.

The ability of ADNF III polypeptides to protect against learning and memory deficiencies associated with cholinergic blockade was also investigated. Cholinergic blockade was obtained in rats by administration of the cholinotoxin AF64A, NAPVSIPQ (SEQ ID NO:6) (termed NAP in FIG. 8). NAPVSIPQ (SEQ ID NO:6) was administered intranasally and the water maze experiments were performed as before (Gozes et al., *Proc. Natl. Acad. Sci. USA* 93:427–432 (1996)). As seen in FIG. 8, a significant difference was observed between the AF64A-treated animals and the animals treated with AF64A and NAPVSIPQ (SEQ ID NO:6) on the third day of training. Thus, animals that were cholinergically impaired when treated with the peptide showed improvement in their learning and memory capacities and behaved as control animals.

The in vivo efficacy of NAP was assessed in apolipoprotein E (ApoE)-deficient homozygous mice, a useful model system for studies of neurodegeneration and neuroprotection (Plump et al., *Cell* 71:343–353 (1992); Gordon et al., *Neuroscience Letters* 199:1–4 (1995); Gozes et al., *J. Neurobiol.* 33:329–342 (1997)). Brain ApoE coordinates the mobilization and redistribution of cholesterol in association with repair, growth, maintenance, and plasticity (Masliah et al., *Exp. Neurol.* 136:107–122 (1995)). One of the three common alleles of ApoE, the ApoE4 allele, was identified as a major susceptibility gene for Alzheimer's disease (Weisgraber et al., *Current Opinion in Structural Biology* 4:507–515 (1994)). ApoE4 promotes the assembly of the β-amyloid peptide into toxic filaments, while ApoE2 inhibits β-amyloid peptide toxic aggregation. Previous studies have identified neuronal destruction and memory impairments in the ApoE-deficient mice, that may mimic the ApoE4 genotype in man (Oitzl et al., *Brain Res.* 752:189–196 (1997)).

Figure 16:
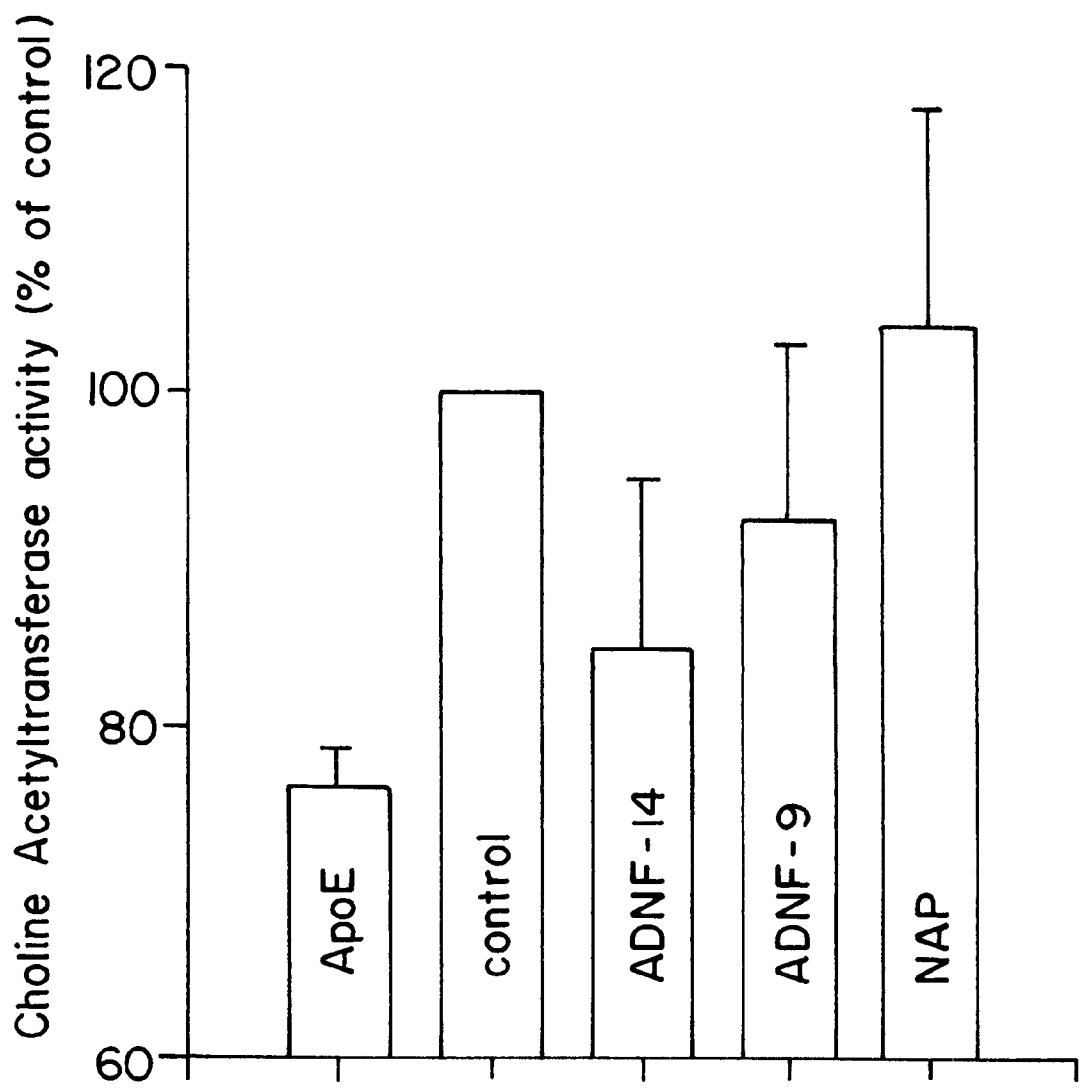
FIG. 16 illustrates that APO-E deficient mice exhibit a reduction in choline acetyl transferase activity. The graph depicts incorporation of radio-labeled choline into acetylcholine. Experiments were conducted as described. Apo-E deficient mice are designated: ApoE; 100% activity in the control (C57B6) mice indicated 669–758.4 pmole/mg protein/min. As the experiments were repeated 3–5 times the results were standardized against the control calibrated at 100% per each experiment. ApoE-deficient mice daily injected with peptides are designated ADNF-14, ADNF-9, and NAP, respectively.

During postnatal development, Apo-E-deficient mice also exhibited a significant decrease (about 25%) in brain ChAT (choline acetyl transferase) activity in comparison to age-matched (21 day old) inbred C57B6 mice (Gozes et al., *J. Neurobiol.* 33:329–342 (1997)). Daily subcutaneous injections of ApoE-deficient mice with NAP (from birth to 14 days of age) resulted in brain ChAT activity (at 21 days of age) that was not significantly different from inbred C57B6 mice (see FIG. 16). In addition brain ChAT activity in ApoE-deficient mice was significantly improved as compared to vehicle-treated or untreated Apo-E deficient mice ($P<0.009$). In contrast, similar treatment with ADNF-14, or ADNF-9, did not significantly improve cholinergic activity, in this model system. ChAT activity was measured according to published procedures (Fonnum et al., *Neurochem.* 24:407–409 (1975)).

Northern blot hybridization has identified a unique 5.5 kb ADNF III mRNA (FIG. 9) in the mouse brain (28-day-old), that was increased by 36% (n=5, $P<0.04$) in ApoE-deficient mice (FIG. 9). Comparison of different adult rodent tissues revealed an enrichment in brain-derived structures (cerebral cortex, cerebellum and hind brain) and low abundance in the liver, kidney, spleen, and lung (data not shown). Taken together, the increase observed in the deficient mice may represent a compensatory mechanism. The same animals have previously been shown to exhibit a reduction in VIP mRNA that may be associated with decreased neuronal function. Daily injections (for the first two weeks of life) of NAP to ApoE-deficient newborn pups did not change ADNP mRNA content in the 28-day-old mice (FIG. 9).

Figure 10:
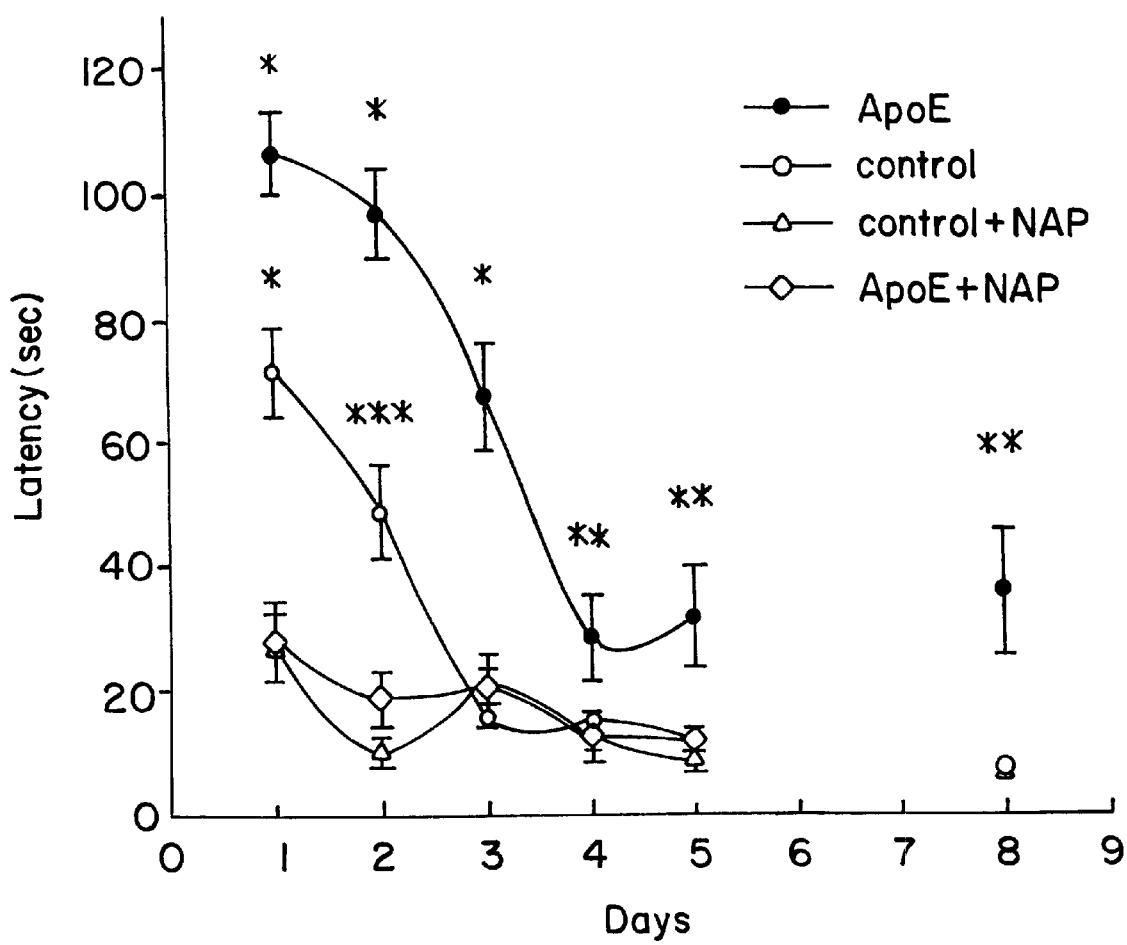
FIG. 10 illustrates ApoE-deficient mice that exhibit an impairment in learning and memory, which is ameliorated by prophylactic NAP treatment. Two daily water maze trials were performed on three week-old animals. Groups tested were: 1. control animals injected with vehicle for the first two weeks of life (35 animals of six different litters, with 5–7 animals from each litter, open circles); 2. ApoE-deficient animals injected with vehicle for the first two weeks of life (18 animals derived from three different litters, with 5–7 pups per litter, closed circles); 3. control animals chronically treated with NAP for the first two weeks of life (14 animals derived from three different litters, open triangles); and 4. ApoE-deficient mice chronically treated with NAP for the first two weeks of life (19 animals derived from three different litters, open rectangles). The figure depicts latency (of the second daily trial), measured in seconds, to reach the hidden platform 0.5 min. after being on it. Tests were performed over five consecutive days, and then with a two day delay tested for one additional day. ApoE=ApoE-deficient animals. There was no differences between animals treated with vehicle and untreated animals (data not shown). Statistical comparisons shown were made: 1. between ApoE-deficient and controls; 2. between ApoE-treated with NAP and ApoE-treated with vehicle; and 3. between control-treated with NAP and control-treated with vehicle (*$P<0.001$; $P<0.03$; *$P<0.002$).

Marked improvements of cognitive functions, however, were observed a week after cessation of peptide treatment (in 21-day-old mice exposed to an eight-day training protocol, FIG. 10). Intact working memory processes were examined by performance in a water maze, measuring the time required to find a hidden platform in the second of two daily trials (see Gordon et al., *Neuroscience Letters* 199:1–4 (1995)). The platform location and the starting point in which the animal was placed in the water were held constant within each pair of daily trials, but both locations were changed every day. ApoE-deficient mice were significantly retarded as compared to control mice, even after eight training days (FIG. 10). In contrast, NAP-treated ApoE-deficient animals performed as well as control animals on all test days. Measurements of choline acetyl transferase activity in the brains of 21-day-old mice indicated that it was significantly reduced in the deficient animals, while peptide-treated animals showed values indistinguishable from controls (data not shown). Furthermore, and unexpectedly, chronic treatment of control animals with NAP also improved their performance (FIG. 10). Similar results were obtained in a rat model of cholinergic deficiency (with the cholinotoxin AF64A) following intranasal administration of NAP (data not shown).

Figure 17:
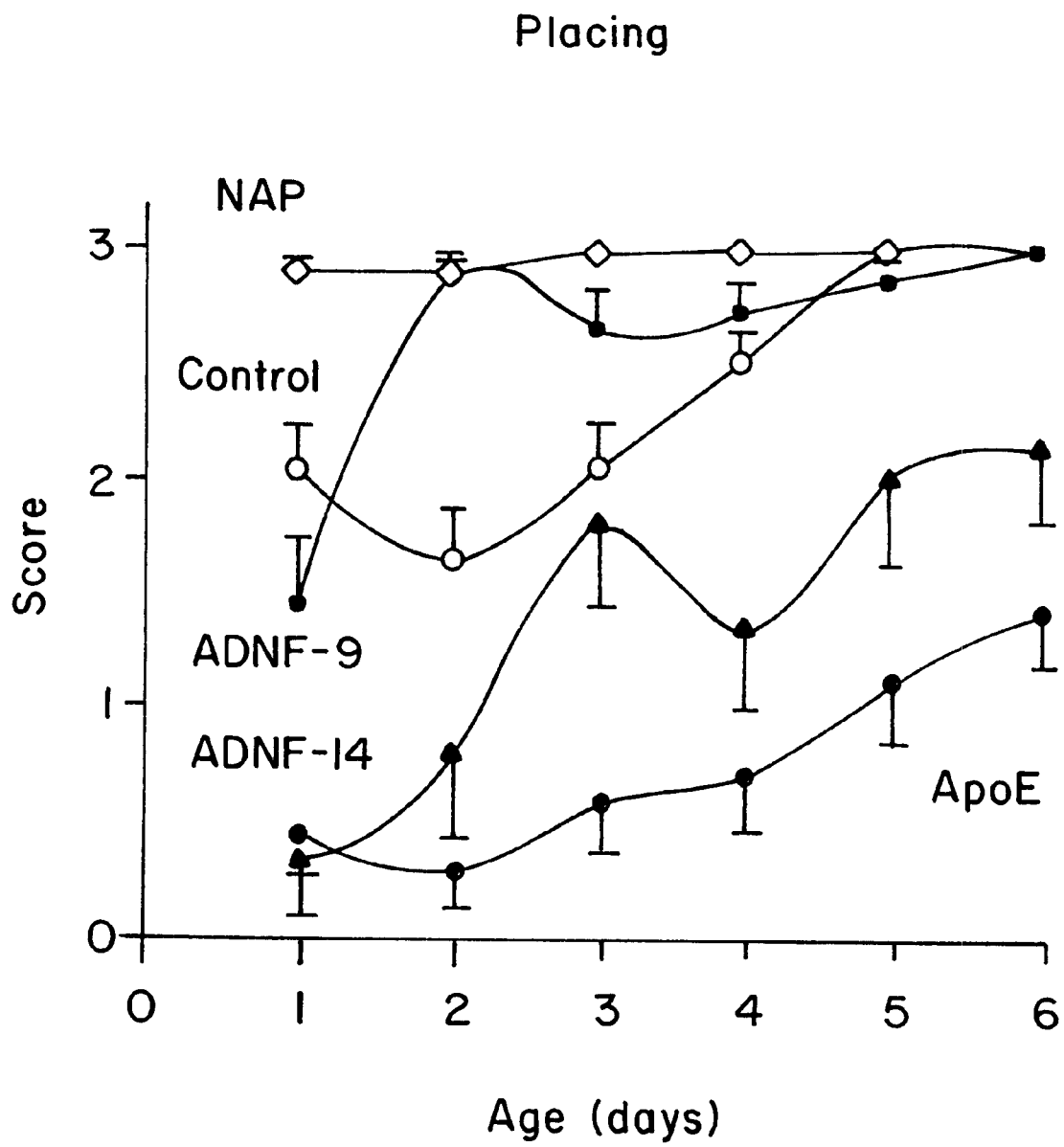
FIG. 17 illustrates that ApoE deficient mice exhibit developmental retardation and protection by ADNF III peptides. Animals (15–37 per experimental group, 5–8 per litter) were submitted to placing response assays daily following injection of: 1. saline (open circles, C57B6 mice=control, n=37, closed circles, ApoE deficient=ApoE, n=22). Experiments were repeated three times. Score indicates: 0=no reaction, 1=time to acquire a response shorter than 15 seconds; 2=time to acquire a response shorter than 10 seconds; 3=time to acquire a response shorter than 5 seconds. Age (days) indicate: the age of the tested animals in days. Results are mean±SEM.

Further measurements in the Apo-E-deficient mouse included assessments of the time of onset of developmental milestones of behavior. As previously demonstrated, major differences were found in the acquisition patterns of placing and cliff avoidance responses between ApoE-deficient animals and age-matched inbred C5B6 mice (FIG. 17). However, daily injection of the deficient mice with ADNF-14, ADNF-9, or NAP showed acceleration of the acquisition of the placing response and the cliff avoidance response. As an example, the placing response is demonstrated in FIG. 17. A significant difference was observed among the treatment groups on the first day of testing ($P<0.0001$), with inbred C57B6 mice developing faster than the ApoE-deficient animals. Injection of NAP and ADNF-9, but not ADNF-14, resulted in marked improvement even at the first day of treatment, suggesting that an hour exposure to the short peptide was enough to elicit a response. NAP-treated animals were the fastest. From the second postnatal day onwards, the best performers were the NAP and ADNF-9 treated ApoE-deficient animals ($P<0.0001$). In contrast to the ApoE-deficient animals treated with NAP or ADNF-9, those ApoE-deficient animals treated with ADNF-14 did not develop as fast and a significant difference between treated and untreated animals began to appear only on the third postnatal day ($P<0.05$). Furthermore, although ADNF-14 administration improved the development of the placing response in ApoE-deficient animals, the treated mice never reached the level of performance of the NAP or ADNF-9 animals.

The present invention represent the first identification of a cloned cDNA expressing a femtomolar acting neuroprotective protein with an eight amino acids core peptide protecting against β-amyloid neurotoxicity and memory deficiencies associated with the Alzheimer's related cholinergic deficiencies.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

Discussion of the Accompanying Sequence Listing

The information for the nucleic acid sequences are presented as DNA sequence information. One of skill will readily understand that portions of the sequences also fully describe RNAs encoded by the sequence (e.g., by substitution of T residues with corresponding U residues), and a variety of conservatively modified variations, including silent substitutions of the sequences.

While only a single strand of sequence information is typically shown, one of skill will immediately appreciate that the complete corresponding complementary sequence is fully described by comparison to the given sequences. Accordingly, each nucleic acid sequence optionally comprises the strand complementary to the depicted sequence.

A variety of conservatively modified variations of the amino acid sequences provided in the sequence listing will be apparent to one of skill. Conservative substitution tables providing functionally similar amino acids are well known in the art and are described herein.

One of skill will also recognize that a very large variety of nucleic acid sequences encode each of given polypeptide due to the codon degeneracy present in the genetic code. Each of the nucleic acids that encodes the given polypeptide is described by comparison to the amino acid sequence and translation via the genetic code. Accordingly, one of skill can generate every nucleic acid sequence that encodes any given amino acid sequence.

SEQUENCE LISTING

```
<160> NUMBER OF SEQ ID NOS: 63

<210> SEQ ID NO 1
<211> LENGTH: 1000
<212> TYPE: PRT
<213> ORGANISM: Homo sapiens
<220> FEATURE:
<223> OTHER INFORMATION: H3' human activity dependent neurotrophic
      factor III (ADNF III) clone
<220> FEATURE:
<221> NAME/KEY: MOD_RES
<222> LOCATION: (801)
<223> OTHER INFORMATION: Xaa = unknown
<220> FEATURE:
<221> NAME/KEY: MOD_RES
<222> LOCATION: (817)
<223> OTHER INFORMATION: Xaa = unknown
<220> FEATURE:
<221> NAME/KEY: MOD_RES
<222> LOCATION: (821)
<223> OTHER INFORMATION: Xaa = unknown
<220> FEATURE:
<221> NAME/KEY: MOD_RES
<222> LOCATION: (833)
<223> OTHER INFORMATION: Xaa = unknown
<220> FEATURE:
<221> NAME/KEY: MOD_RES
<222> LOCATION: (854)
<223> OTHER INFORMATION: Xaa = unknown
<220> FEATURE:
<221> NAME/KEY: MOD_RES
<222> LOCATION: (866)
<223> OTHER INFORMATION: Xaa = unknown
<220> FEATURE:
<221> NAME/KEY: MOD_RES
<222> LOCATION: (870)
<223> OTHER INFORMATION: Xaa = unknown
<220> FEATURE:
<221> NAME/KEY: MOD_RES
<222> LOCATION: (877)
<223> OTHER INFORMATION: Xaa = unknown
<220> FEATURE:
<221> NAME/KEY: MOD_RES
<222> LOCATION: (882)
<223> OTHER INFORMATION: Xaa = unknown
<220> FEATURE:
<221> NAME/KEY: MOD_RES
<222> LOCATION: (922)
<223> OTHER INFORMATION: Xaa = unknown
<220> FEATURE:
<221> NAME/KEY: MOD_RES
<222> LOCATION: (948)
<223> OTHER INFORMATION: Xaa = unknown
<220> FEATURE:
```

-continued

```
<221> NAME/KEY: MOD_RES
<222> LOCATION: (959)
<223> OTHER INFORMATION: Xaa = unknown
<220> FEATURE:
<221> NAME/KEY: MOD_RES
<222> LOCATION: (964)
<223> OTHER INFORMATION: Xaa = unknown
<220> FEATURE:
<221> NAME/KEY: MOD_RES
<222> LOCATION: (967)
<223> OTHER INFORMATION: Xaa = unknown
<220> FEATURE:
<221> NAME/KEY: MOD_RES
<222> LOCATION: (980)
<223> OTHER INFORMATION: Xaa = unknown

<400> SEQUENCE: 1

Met Val Asn Arg Leu Ser Ile Pro Lys Pro Asn Leu Asn Ser Thr Gly
  1               5                  10                  15

Val Asn Met Met Ser Ser Val His Leu Gln Gln Asn Asn Tyr Gly Val
             20                  25                  30

Lys Ser Val Gly Gln Gly Tyr Ser Val Gly Gln Ser Met Arg Leu Gly
         35                  40                  45

Leu Gly Gly Asn Ala Pro Val Ser Ile Pro Gln Gln Ser Gln Ser Val
     50                  55                  60

Lys Gln Leu Leu Pro Ser Gly Asn Gly Arg Ser Tyr Gly Leu Gly Ser
 65                  70                  75                  80

Glu Gln Arg Ser Gln Ala Pro Ala Arg Tyr Ser Leu Gln Ser Ala Asn
                 85                  90                  95

Ala Ser Ser Leu Ser Ser Gly His Leu Lys Ser Pro Ser Leu Ser His
            100                 105                 110

Ser Gln Ala Ser Arg Val Leu Gly Gln Ser Ser Ser Lys Pro Ala Ala
        115                 120                 125

Ala Ala Thr Gly Pro Pro Gly Asn Thr Ser Ser Thr Gln Lys Trp
    130                 135                 140

Lys Ile Cys Thr Ile Cys Asn Glu Leu Phe Pro Glu Asn Val Tyr Ser
145                 150                 155                 160

Val His Phe Glu Lys Glu His Lys Ala Glu Lys Val Pro Ala Val Ala
                165                 170                 175

Asn Tyr Ile Met Lys Ile His Asn Phe Thr Ser Lys Cys Leu Tyr Cys
            180                 185                 190

Asn Arg Tyr Leu Pro Thr Asp Thr Leu Leu Asn His Met Leu Ile His
        195                 200                 205

Gly Leu Ser Cys Pro Tyr Cys Arg Ser Thr Phe Asn Asp Val Glu Lys
    210                 215                 220

Met Ala Ala His Met Arg Met Val His Ile Asp Glu Glu Met Gly Pro
225                 230                 235                 240

Lys Thr Asp Ser Thr Leu Ser Phe Asp Leu Thr Leu Gln Gln Gly Ser
                245                 250                 255

His Thr Asn Ile His Leu Leu Val Thr Thr Tyr Asn Leu Arg Asp Ala
            260                 265                 270

Pro Ala Glu Ser Val Ala Tyr His Ala Gln Asn Asn Pro Pro Val Pro
        275                 280                 285

Pro Lys Pro Gln Pro Lys Val Gln Glu Lys Ala Asp Ile Pro Val Lys
    290                 295                 300

Ser Ser Pro Gln Ala Ala Val Pro Tyr Lys Lys Asp Val Gly Lys Thr
305                 310                 315                 320

Leu Cys Pro Leu Cys Phe Ser Ile Leu Lys Gly Pro Ile Ser Asp Ala
```

-continued

```
                    325                 330                 335
Leu Ala His His Leu Arg Glu Arg His Gln Val Ile Gln Thr Val His
                340                 345                 350
Pro Val Glu Lys Lys Leu Thr Tyr Lys Cys Ile His Cys Leu Gly Val
                355                 360                 365
Tyr Thr Ser Asn Met Thr Ala Ser Thr Ile Thr Leu His Leu Val His
            370                 375                 380
Cys Arg Gly Val Gly Lys Thr Gln Asn Gly Gln Asp Lys Thr Asn Ala
385                 390                 395                 400
Pro Ser Arg Leu Asn Gln Ser Pro Ser Leu Ala Pro Val Lys Arg Thr
                405                 410                 415
Tyr Glu Gln Met Glu Phe Pro Leu Leu Lys Arg Lys Leu Asp Asp
                420                 425                 430
Asp Ser Asp Ser Pro Ser Phe Phe Glu Glu Lys Pro Glu Glu Pro Val
            435                 440                 445
Val Leu Ala Leu Asp Pro Lys Gly His Glu Asp Ser Tyr Glu Ala
            450                 455                 460
Arg Lys Ser Phe Leu Thr Lys Tyr Phe Asn Lys Gln Pro Tyr Pro Thr
465                 470                 475                 480
Arg Arg Glu Ile Glu Lys Leu Ala Ala Ser Leu Trp Leu Trp Lys Ser
                485                 490                 495
Asp Ile Ala Ser His Phe Ser Asn Lys Arg Lys Lys Cys Val Arg Asp
                500                 505                 510
Cys Glu Lys Tyr Lys Pro Gly Val Leu Leu Gly Phe Asn Met Lys Glu
                515                 520                 525
Leu Asn Lys Val Lys His Glu Met Asp Phe Asp Ala Glu Trp Leu Phe
            530                 535                 540
Glu Asn His Asp Glu Lys Asp Ser Arg Val Asn Ala Ser Lys Thr Ala
545                 550                 555                 560
Asp Lys Lys Leu Asn Leu Gly Lys Glu Asp Asp Ser Ser Ser Asp Ser
                565                 570                 575
Phe Glu Asn Leu Glu Glu Glu Ser Asn Glu Ser Gly Ser Pro Phe Asp
            580                 585                 590
Pro Val Phe Glu Val Glu Pro Lys Ile Ser Asn Asp Asn Pro Glu Glu
            595                 600                 605
His Val Leu Lys Val Ile Pro Glu Asp Ala Ser Glu Ser Glu Glu Lys
        610                 615                 620
Leu Asp Gln Lys Glu Asp Gly Ser Lys Tyr Glu Thr Ile His Leu Thr
625                 630                 635                 640
Glu Glu Pro Thr Lys Leu Met His Asn Ala Ser Asp Ser Glu Val Asp
                645                 650                 655
Gln Asp Asp Val Val Glu Trp Lys Asp Gly Ala Ser Pro Ser Glu Ser
            660                 665                 670
Gly Pro Gly Ser Gln Gln Val Ser Asp Phe Glu Asp Asn Thr Cys Glu
            675                 680                 685
Met Lys Pro Gly Thr Trp Ser Asp Glu Ser Ser Gln Ser Glu Asp Ala
        690                 695                 700
Arg Ser Ser Lys Pro Ala Ala Lys Lys Ala Thr Met Gln Gly Asp
705                 710                 715                 720
Arg Glu Gln Leu Lys Trp Lys Asn Ser Ser Tyr Gly Lys Val Glu Gly
                725                 730                 735
Phe Trp Ser Lys Asp Gln Ser Gln Trp Lys Asn Ala Ser Glu Asn Asp
                740                 745                 750
```

-continued

```
Glu Arg Leu Ser Asn Pro Gln Ile Glu Trp Gln Asn Ser Thr Ile Asp
        755                 760                 765
Ser Glu Asp Gly Glu Gln Phe Asp Asn Met Thr Asp Gly Val Thr Glu
    770                 775                 780
Pro Met His Gly Ser Leu Ala Gly Val Lys Leu Ser Ser Gln Gln Ala
785                 790                 795                 800
Xaa Val Pro Gly Ser Leu Ala Leu Val Thr Cys Cys Ser Leu Glu Leu
                805                 810                 815
Xaa Ser Pro Val Xaa Leu Gln Ser Cys Leu Leu Thr Gly Thr Ala Leu
            820                 825                 830
Xaa Val Leu Val Gly Leu Trp Gly Met Trp Pro Leu Gln Phe Gln Trp
        835                 840                 845
Leu Phe Leu Ser Leu Xaa Gln Asp Arg Leu Phe Leu Leu Gln Asn Leu
    850                 855                 860
Leu Xaa Gln Thr Arg Xaa Leu Asn Val Lys Asn Gln Xaa Ala Gly Asp
865                 870                 875                 880
Ser Xaa Ile Leu Thr Arg Lys Ser Arg Gly Leu Phe Leu Ser Ala Phe
                885                 890                 895
Ser Thr Phe Leu Ser Leu Cys Glu Met Ile Gly Gln Met Ser Leu Arg
            900                 905                 910
Ser Val Lys Leu Ile His Met Val Val Xaa Gly Gln His Thr Ser Tyr
        915                 920                 925
Gln Ser Asn Val Tyr Ser Arg Leu Trp Glu Lys Arg Phe Phe Met
    930                 935                 940
Tyr Ser Phe Xaa Ile Val Glu Met Tyr Ile Cys Thr Val Phe Xaa Thr
945                 950                 955                 960
Tyr Ser Lys Xaa Cys Ser Xaa Ser Cys Tyr Cys Val Pro Ile Ile Asp
                965                 970                 975
Phe Phe Phe Xaa Cys Cys Pro Cys Cys Val Ile Asn Ala Leu Ser Ser
            980                 985                 990
Leu Pro Ser Lys Ser Ser Lys Leu
        995                 1000
```

<210> SEQ ID NO 2
<211> LENGTH: 4874
<212> TYPE: DNA
<213> ORGANISM: Homo sapiens
<220> FEATURE:
<223> OTHER INFORMATION: H3' human activity dependent neurotrophic factor III (ADNF III) cDNA clone

<400> SEQUENCE: 2

```
atggtgaatc gactctcaat accaaagcct aacttaaatt ctacaggagt caacatgatg      60
tccagtgttc atctgcagca gaacaactat ggagtcaaat ctgtaggcca gggttacagt     120
gttggtcagt caatgagact gggtctaggt ggcaacgcac cagtttccat tcctcaacaa     180
tctcagtctg taaagcagtt acttccaagt ggaaacggaa ggtcttatgg gcttgggtca     240
gagcaaaggt cccaagcacc agcaagatac tccctgcagt ctgctaatgc ctcttctctc     300
tcatcgggcc acttaaagtc tccttccctc tctcattcac aggcatctag agtgttaggt     360
cagtccagtt ccaaacctgc tgcagctgcc acaggccctc ccccaggtaa cacttcctca     420
actcaaaagt ggaaaatatg tacaatctgt aatgagcttt ttcctgaaaa tgtctatagt     480
gtgcacttcg aaaagaaaca taagctgag aaagtcccag cagtagccaa ctacattatg     540
aaaatacaca atttactag caaatgcctc tactgtaatc gctatttacc cacagatact     600
```

```
ctgctcaacc atatgttaat tcatggtctg tcttgtccat attgccgttc aactttcaat    660
gatgtggaaa agatggccgc acacatgcgg atggttcaca ttgatgaaga gatgggacct    720
aaaacagatt ctactttgag ttttgatttg acattgcagc agggtagtca cactaacatc    780
catctcctgg taactacata caatctgagg gatgcccag ctgaatctgt tgcttaccat     840
gcccaaaata atcctccagt tcctccaaag ccacagccaa aggttcagga aaaggcagat    900
atccctgtaa aaagttcacc tcaagctgca gtgccctata aaaagatgt tgggaaaacc     960 ctttgtcctc tttgcttttc aatcctaaaa ggacccatat ctgatgcact tgcacatcac   1020
ttacgagaga ggcaccaagt tattcagacg gttcatccag ttgagaaaaa gctcacctac   1080
aaatgtatcc attgccttgg tgtgtatacc agcaacatga ccgcctcaac tatcactctg   1140
catctagttc actgcagggg cgttggaaag acccaaaatg ccaggataa acaaatgca     1200 ccctctcggc ttaatcagtc tccaagtctg gcacctgtga agcgcactta cgagcaaatg   1260
gaatttccct tactgaaaaa acgaaagtta gatgatgata gtgattcacc cagcttcttt   1320
gaagagaagc ctgaagagcc tgttgtttta gctttagacc ccaagggtca tgaagatgat   1380
tcctatgaag ccaggaaaag ctttctaaca aagtatttca caaacagcc ctatcccacc    1440 aggagagaaa ttgagaagct agcagccagt ttatggttat ggaagagtga catcgcttcc   1500
cattttagta acaaaaggaa gaagtgtgtc cgtgattgtg aaaagtacaa gcctggcgtg   1560
ttgctggggt ttaacatgaa agaattaaat aaagtcaagc atgagatgga ttttgatgct   1620
gagtggctat ttgaaaatca tgatgagaag gattccagag tcaatgctag taagactgct   1680
gacaaaaagc tcaaccttgg gaaggaagat gacagttcct cagacagttt tgaaaatttg   1740
gaagaagaat ccaatgaaag tggtagccct tttgaccctg tttttgaagt tgaacctaaa   1800
atctctaacg ataacccaga ggaacatgta ctgaaggtaa ttcctgagga tgcttcagaa   1860
tctgaggaga agctagacca aaaagaggat ggttcaaaat acgaaactat tcatttgact   1920
gaggaaccaa ccaaactaat gcacaatgca tctgatagtg aggttgacca agacgatgtt   1980
gttgagtgga agacggtgc ttctccatct gagagtgggc ctggatccca acaagtgtca    2040
gactttgagg acaatacctg cgaaatgaaa ccaggaacct ggtctgacga gtcttcccaa   2100
agcgaagatg caaggagcag taagccagct gccaaaaaaa aagctaccat gcaaggtgac   2160
agagagcagt tgaaatggaa gaatagttcc tatggaaaag ttgaagggtt ttggtctaag   2220
gaccagtcac agtggaagaa tgcatctgag aatgatgagc gcttatctaa cccccagatt   2280
gagtggcaga atagcacaat tgacagtgag gatggggaac agtttgacaa catgactgat   2340
ggagtaactg agcccatgca tggcagctta gccggagtta aactgagcag ccaacaggcc   2400
taagtgccag gttccctggc gttggtgaca tgctgcagcc tggaactctg atctccagtg   2460
tgactgcaaa gctgtcttct cactggtact gccttgtgag tactggttgg actgtggggc   2520
atgtggccgc tgcagttcca gtggttattt ctaagtctat gacaggacag gctgttcttg   2580
cttcagaacc ttctctgaca gacacggtaa ctaaatgtga aaaccaata agctggtgac    2640 tcatgaatac tcacgaggaa agcagaggt ttattttat ctgccttttc aacatttctt    2700
tccctctgtg aaatgattgg tcagatgtct ttgagaagtg ttaaactaat tcacatggta   2760
gtgtagggcc aacatacaag ctaccagtct aatgtgtata gtagactttg ggaaaagcga   2820 tttttttttca tgtattcatt ctgaatagtt gaaatgtata tttgtacagt cttttagacc   2880
tattccaagt gatgctcatg atcctgttac tgtgtgccca tcatagattt cttttttag    2940
```

-continued

```
tgttgccctt gctgtgtaat aaacgctcta tctagtttac ctagcaaaag ctcaaaactg      3000
cgctagtatg gacttttgg acagacttag tttttgcaca taaccttgta caatcttgca      3060
acagaggcca gccacgtaag atatatatct ggactctctt gtattatagg attttcttg      3120 ttctgaatat ccttgacatt acagctgtca aaaacaaaaa ctggtatttc agatctgttt      3180
tctgaaatct tttaagctaa aatcacatgc aagaattgac tttgcagcta ctaattttga      3240 cacctttag atctgtataa aagtgtgttg tgttgaagca gcaaaccaat gagtgctgca       3300
ttttggatat ttagttttat ctttagttca acaccatcat ggtggattca tttataccat     3360
ctaatatatg acacactgtt gtagtatgta taattttgtg atctttattt tcccttgta     3420 ttcattttaa gcatctaaat aaattgctgt attgtgctta atgtaaaaaa aaaaaaaaaa      3480
aaactcgacc gtgtgggatg aggccgagca agatggaatt ggggaggagg tgctcaagat     3540
gtccacggag gagatcatcc agcgcacacg gctgctggac agtgagatca agatcatgaa     3600
gagtgaagtg ttgagagtca cccatgagct ccaagccatg aaggacaaga taaaagagaa     3660
cagtgagaaa atcaaagtga acaagaccct gccgtacctt gtctccaacg tcatcgagct     3720
cctggatgtt gatcctaatg accaagagga ggatggtgcc aatattgacc tggactccca     3780
gaggaagggc aagtgtgctg tgatcaaaac ttttacacga cagacgtact tccttcctgt     3840
gattgggttg gtggatgctg aaaagctaaa gccaggagac ctggtgggtg tgaacaaaga     3900
ctcctatctg atcctggaga cgctgcccac agagtatgac tcgcgggtga aggccatgga     3960
ggtagacgag aggcccacgg agcaatacag tgacattggg ggtttggaca agcagatcca     4020
ggagctggtg gaggccattg tcttgccaat gaaccacaag gagaagtttg agaacttggg     4080
gatccaacct ccaaagggg tgctgatgta tgggcccca gggacgggga agaccctcct     4140
ggcccgggcc tgtgccgcac agactaaggc caccttccta agctggctg gccccccagct    4200 ggtgcagatg tttcattgga gatggtgcca agctagtccg ggatgccttt gcctggcca     4260 aggagaaagc gccctctatc atcttcattg atgagttgga tgccatcggc accaagcgct     4320
ttgacagtga gaaggctggg gaccgggagg tgcagaggca aatgctggag cttctgaacc     4380
agctggatgg cttccagccc aacacccaag ttaaggtaat tgcagccaca aacagggtgg     4440
acatcctgga ccccgccctt cttcccgttc gggccgcctt gaccgcaaga tagagttccc     4500
gatgcccaat gaggaggccc gggccagaat catgcagatc cactcccgaa agatgaatgt     4560
cagtcctgac gtgaaatacg aggagctggc ccgctgcaca gatgaattca tgggcccca     4620 gtgcaaggct gtgtgtgtgg aggcgggcat gatcgcantg cgcagggtgt ccacggagct     4680
cacccacgag gactacatgg aaggcattct ggaggtgcag gccaagaaga agccaacct     4740 acaatactac gcctagggca cacaggccag cccagtttc acggctgaag tgcgcaataa     4800
aagatggttt agggtcaaaa aaaaaaaaaa aaaaaaaaaa aaaaaaaaaa aaaaaaaaaa     4860
aaaaaaaaaa aaaa                                                       4874
```

<210> SEQ ID NO 3
<211> LENGTH: 806
<212> TYPE: PRT
<213> ORGANISM: Mus musculus
<220> FEATURE:
<223> OTHER INFORMATION: mouse activity dependent neurotrophic factor III (ADNF III) cDNA clone

<400> SEQUENCE: 3

Met Val Asn Arg Leu Ser Ile Pro Lys Pro Asn Leu Asn Ser Thr Gly
 1               5                  10                  15

-continued

Val Asn Met Met Ser Asn Val His Leu Gln Gln Asn Asn Tyr Gly Val
            20                  25                  30

Lys Ser Val Gly Gln Ser Tyr Gly Val Gly Gln Ser Val Arg Leu Gly
            35                  40                  45

Leu Gly Gly Asn Ala Pro Val Ser Ile Pro Gln Gln Ser Gln Ser Val
            50                  55                  60

Lys Gln Leu Leu Pro Ser Gly Asn Gly Arg Ser Phe Gly Leu Gly Ala
 65                  70                  75                  80

Glu Gln Arg Pro Pro Ala Ala Arg Tyr Ser Leu Gln Thr Ala Asn
                 85                  90                  95

Thr Ser Leu Pro Pro Gly Gln Val Lys Ser Pro Ser Val Ser Gln Ser
            100                 105                 110

Gln Ala Ser Arg Val Leu Gly Gln Ser Ser Lys Pro Pro Pro Ala
            115                 120                 125

Ala Thr Gly Pro Pro Ser Asn His Cys Ala Thr Gln Lys Trp Lys
            130                 135                 140

Ile Cys Thr Ile Cys Asn Glu Leu Phe Pro Glu Asn Val Tyr Ser Val
145                 150                 155                 160

His Phe Glu Lys Glu His Lys Ala Glu Lys Val Pro Ala Val Ala Asn
            165                 170                 175

Tyr Ile Met Lys Ile His Asn Phe Thr Ser Lys Cys Leu Tyr Cys Asn
            180                 185                 190

Arg Tyr Leu Pro Thr Asp Thr Leu Leu Asn His Met Leu Ile His Gly
            195                 200                 205

Leu Ser Cys Pro Tyr Cys Arg Ser Thr Phe Asn Asp Val Glu Lys Met
            210                 215                 220

Ala Ala His Met Arg Met Val His Ile Asp Glu Glu Met Gly Pro Lys
225                 230                 235                 240

Thr Asp Ser Thr Leu Ser Phe Asp Leu Thr Leu Gln Gln Gly Ser His
            245                 250                 255

Thr Asn Ile His Leu Leu Val Thr Thr Tyr Asn Leu Arg Asp Ala Pro
            260                 265                 270

Ala Glu Ser Val Ala Tyr His Ala Gln Asn Asn Ala Pro Val Pro Pro
            275                 280                 285

Lys Pro Gln Pro Lys Val Gln Glu Lys Ala Asp Val Pro Val Lys Ser
            290                 295                 300

Ser Pro Gln Ala Ala Val Pro Tyr Lys Lys Asp Val Gly Lys Thr Leu
305                 310                 315                 320

Cys Pro Leu Cys Phe Ser Ile Leu Lys Gly Pro Ile Ser Asp Ala Leu
            325                 330                 335

Ala His His Leu Arg Glu Arg His Gln Val Ile Gln Thr Val His Pro
            340                 345                 350

Val Glu Lys Lys Leu Thr Tyr Lys Cys Ile His Cys Leu Gly Val Tyr
            355                 360                 365

Thr Ser Asn Met Thr Ala Ser Thr Ile Thr Leu His Leu Val His Cys
            370                 375                 380

Arg Gly Val Gly Lys Thr Gln Asn Gly Gln Asp Lys Thr Asn Ala Pro
385                 390                 395                 400

Ser Arg Leu Asn Gln Ser Pro Gly Leu Ala Pro Val Lys Arg Thr Tyr
            405                 410                 415

Glu Gln Met Glu Phe Pro Leu Leu Lys Lys Arg Lys Leu Glu Glu Asp
            420                 425                 430

-continued

```
Ala Asp Ser Pro Ser Cys Phe Glu Glu Lys Pro Glu Pro Val Val
        435                 440                 445

Leu Ala Leu Asp Pro Lys Gly His Glu Asp Ser Tyr Glu Ala Arg
    450                 455                 460

Lys Ser Phe Leu Thr Lys Tyr Phe Asn Lys Gln Pro Tyr Pro Thr Arg
465                 470                 475                 480

Arg Glu Ile Glu Lys Leu Ala Ala Ser Leu Trp Leu Trp Lys Ser Asp
                485                 490                 495

Ile Ala Ser His Phe Ser Asn Lys Arg Lys Cys Val Arg Asp Cys
            500                 505                 510

Glu Lys Tyr Lys Pro Gly Val Leu Leu Gly Phe Asn Met Lys Glu Leu
    515                 520                 525

Asn Lys Val Lys His Glu Met Asp Phe Asp Ala Glu Trp Leu Phe Glu
530                 535                 540

Asn His Asp Glu Lys Asp Ser Arg Val Asn Ala Ser Lys Thr Val Asp
545                 550                 555                 560

Lys Lys His Asn Leu Gly Lys Glu Asp Asp Ser Phe Ser Asp Ser Phe
                565                 570                 575

Glu His Leu Glu Glu Glu Ser Asn Gly Ser Gly Ser Pro Phe Asp Pro
            580                 585                 590

Val Phe Glu Val Glu Pro Lys Ile Pro Ser Asp Asn Leu Glu Glu Pro
        595                 600                 605

Val Pro Lys Val Ile Pro Glu Gly Ala Leu Glu Ser Glu Lys Leu Asp
610                 615                 620

Gln Lys Glu Glu Glu Glu Glu Glu Glu Asp Gly Ser Lys Tyr
625                 630                 635                 640

Glu Thr Ile His Leu Thr Glu Glu Pro Ala Lys Leu Met His Asp Ala
                645                 650                 655

Ser Asp Ser Glu Val Asp Gln Asp Val Val Glu Trp Lys Asp Gly
            660                 665                 670

Ala Ser Pro Ser Glu Ser Gly Pro Gly Ser Gln Gln Ile Ser Asp Phe
        675                 680                 685

Glu Asp Asn Thr Cys Glu Met Lys Pro Gly Thr Trp Ser Asp Glu Ser
690                 695                 700

Ser Gln Ser Glu Asp Ala Arg Ser Ser Lys Pro Ala Ala Lys Lys Lys
705                 710                 715                 720

Ala Thr Val Gln Asp Asp Thr Glu Gln Leu Lys Trp Lys Asn Ser Ser
                725                 730                 735

Tyr Gly Lys Val Glu Gly Phe Trp Ser Lys Asp Gln Ser Gln Trp Glu
            740                 745                 750

Asn Ala Ser Glu Asn Ala Glu Arg Leu Pro Asn Pro Gln Ile Glu Trp
        755                 760                 765

Gln Asn Ser Thr Ile Asp Ser Glu Asp Gly Gln Phe Asp Ser Met
    770                 775                 780

Thr Asp Gly Val Ala Asp Pro Met His Gly Ser Leu Thr Gly Val Lys
785                 790                 795                 800

Leu Ser Ser Gln Gln Ala
                805
```

<210> SEQ ID NO 4
<211> LENGTH: 2421
<212> TYPE: DNA
<213> ORGANISM: Mus musculus
<220> FEATURE:
<223> OTHER INFORMATION: one mouse activity dependent neurotrophic factor III (ADNF III) cDNA clone

<400> SEQUENCE: 4

```
atggtaaacc gattgtcaat accaaagccc aacttaaatt caacgggagt caacatgatg    60
tccaatgttc acctgcagca aaacaactat ggagtcaaat ctgtgggcca gagctatggt   120
gttggccagt cagtgaggct gggactaggt ggcaatgctc cagtttccat ccctcaacag   180
tctcagtccg tgaaacagtt acttccaagt gggaatggga ggtcttttgg gctaggtgct   240
gagcagaggc cccagcagc agccaggtac tccctgcaga ctgccaacac ctctctaccc   300
ccaggccaag tgaagtctcc ctctgtgtct cagtcacagg catctagagt attaggtcag   360
tccagttcta aacctccacc agccgccaca ggccctcctc aagcaacca ctgtgccact    420
cagaagtgga aaatctgtac aatctgtaac gagcttttcc ctgagaatgt ctatagcgtt   480
cacttcgaaa aggagcataa agctgagaaa gtcccagccg tagctaacta cattatgaaa   540
atacacaatt ttactagcaa atgcctctac tgtaatcgct atttgcctac agatacccta   600
ctcaaccata tgttaattca tggtctgtct tgtccgtatt gccgttccac cttcaatgat   660
gtagagaaga tggcagcaca catgcgaatg gttcatattg atgaagagat ggggcctaaa   720
acggattcta ctttgagctt tgatttgaca ttgcaacagg gcagtcacac caacattcat   780
ctcctggtga ccacatacaa cctgagggat gccccggctg aatcagttgc ttaccatgcc   840
caaaataatg ccccagttcc tccaaagcca caaccaaaag ttcaggaaaa agcagatgtc   900
ccggttaaaa gttcacctca agctgcagtg ccctataaaa aagatgttgg gaagacccct   960
tgccctcttt gcttttcaat actaaaagga cccatatctg atgcacttgc acatcattta  1020
cgagaaagac accaagttat tcagacagtt catccggttg agaaaaagct aacttacaaa  1080
tgtatccatt gccttggtgt gtatactagc aacatgacag cctcaaccat cactctgcat  1140
ctagtccact gcagggggtgt tggaaaaacc cagaatggcc aggacaagac aaacgcacct  1200
tctcggctca atcagtctcc aggcctggcc cctgtgaagc gcacgtatga gcagatggag  1260
tttccactgc taaaaagcg gaagctggag gaggatgctg attccctag ctgcttgaa    1320
gagaagccag aagagcctgt tgttttagct ttagacccca agggtcatga agatgattct  1380
tatgaggcta ggaaaagctt tctcacaaag tacttcaaca acagcccta tcccaccagg   1440
agagaaattg agaagttagc tgccagtcta tggctatgga agagtgacat tgcctcccat  1500
ttcagtaaca gaggaagaa gtgtgtccgc gactgtgaaa agtacaagcc tggtgtgctg  1560
ctaggtttta acatgaaaga attaaataaa gtcaaacacg atggattt tgatgctgag   1620
tggctgtttg aaaatcacga tgagaaagac tcaagagtca atgctagcaa gactgttgac  1680
aaaaagcata accttgggaa agaagatgat agcttctcag atagttttga acatttggaa  1740
gaagaatcca atggaagcgg gagtcctttt gaccctgtct ttgaagttga gcctaaaatt  1800
cccagtgata atttagagga gcctgtaccg aaggttattc cggaaggtgc tttggaatct  1860
gagaagctag accaaaaaga ggaggaggag gaggaggagg aggaggatgg ttcaaaatat  1920
gaaactatcc atttgactga ggaaccagcc aaattaatgc atgatgcctc tgatagtgag  1980
gtagaccaag atgatgtagt tgagtggaaa atggtgctt caccatctga gagtgggcct  2040
ggttcccaac aaatctcaga ctttgaggat aatacatgtg aaatgaaacc aggaacctgg  2100
tctgatgagt cttcccagag tgaagatgca aggagcagta agccagctgc caaaaaaaag  2160
gctacagtgc aagatgacac agagcagtta aaatggaaga atagttccta tggaaaagtt  2220
gaagggtttt ggtccaagga ccagtcacag tgggaaaatg catctgagaa tgcagagcgc  2280
```

```
ttaccaaacc cacagattga gtggcagaat agcacaattg acagtgagga cggggagcag      2340
tttgacagca tgactgacgg agttgctgat cccatgcatg gcagcttaac tggagtgaag      2400
ctgagcagcc agcaagcctg a                                                2421

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:ADNF-9
      active peptide antigen

<400> SEQUENCE: 5

Ser Ala Leu Leu Arg Ser Ile Pro Ala
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:ADNF III-8
      active site core peptide, clone 25 sequence (NAP)

<400> SEQUENCE: 6

Asn Ala Pro Val Ser Ile Pro Gln
 1               5

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:sense primer
      for amplification of ADNF III cDNA

<400> SEQUENCE: 7
tccaatgttc acctgcag                                                    18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:antisense
      primer (bases 438-455) for amplification of ADNF
      III cDNA

<400> SEQUENCE: 8
gctcgttaca gattgtac                                                    18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:sense primer
      (bases 71-90) for amplification of ADNF III cDNA

<400> SEQUENCE: 9
acctgcagca aaacaactat                                                  20

<210> SEQ ID NO 10
<211> LENGTH: 88
<212> TYPE: PRT
```

```
<213> ORGANISM: Artificial Sequence
<220> FEATURE:
<223> OTHER INFORMATION: Description of Artificial Sequence:activity
      dependent neurotrophic factor III (ADNF III)
      polypeptide
<220> FEATURE:
<221> NAME/KEY: MOD_RES
<222> LOCATION: (1)..(40)
<223> OTHER INFORMATION: Xaa = any amino acid, Xaa at positions 1-40 may
      be present or absent
<220> FEATURE:
<221> NAME/KEY: MOD_RES
<222> LOCATION: (49)..(88)
<223> OTHER INFORMATION: Xaa = any amino acid, Xaa at positions 49-88
      may be present or absent

<400> SEQUENCE: 10

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Asn Ala Pro Val Ser Ile Pro Gln
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa
             85

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:short hsp60
      homolog control peptide

<400> SEQUENCE: 11

Leu Gly Gly Gly Ser
  1               5

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 12

Ser Val Arg Leu Gly Leu Gly Gly Asn Ala Pro Val Ser Ile Pro Gln
  1               5                  10                  15

Gln Ser

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:ADNF III
      polypeptide; short hsp60 homolog control peptide

<400> SEQUENCE: 13

Val Leu Gly Gly Gly
  1               5
```

```
<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 14

Val Leu Gly Gly
 1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 15

Val Leu Gly Gly Val
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 16

Gly Val Leu Gly Gly
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 17

Leu Gly Leu Gly Gly
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 18

Ser Val Arg Leu Gly Leu Gly Gly
 1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence:related to
      yeast protein PIF1
```

```
<220> FEATURE:
<221> NAME/KEY: MOD_RES
<222> LOCATION: (7)
<223> OTHER INFORMATION: Xaa = unknown
<220> FEATURE:
<221> NAME/KEY: MOD_RES
<222> LOCATION: (10)
<223> OTHER INFORMATION: Xaa = unknown

<400> SEQUENCE: 19

Pro Gln Leu Ile Ser Glu Xaa Ser Phe Xaa Gln
  1               5                  10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence:related to
      yeast protein PIF1
<220> FEATURE:
<221> NAME/KEY: MOD_RES
<222> LOCATION: (5)
<223> OTHER INFORMATION: Xaa = unknown
<220> FEATURE:
<221> NAME/KEY: MOD_RES
<222> LOCATION: (8)
<223> OTHER INFORMATION: Xaa = unknown
<220> FEATURE:
<221> NAME/KEY: MOD_RES
<222> LOCATION: (10)
<223> OTHER INFORMATION: Xaa = unknown

<400> SEQUENCE: 20

Ile Gln Leu Glu Xaa Glu Ile Xaa Glu Xaa Gln Ile Ile
  1               5                  10

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence:ADNF
      I/hsp60-related sequence conjugated through the
      Cys residue to Sephadex for affinity
      chromatography

<400> SEQUENCE: 21

Cys Val Leu Gly Gly Gly Ser Ala Leu Leu Arg Ser Ile Pro Ala
  1               5                  10                  15

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence:peptide
      conjugated through the Cys residue to Sephadex for
      affinity chromatography

<400> SEQUENCE: 22

Cys Ser Ala Leu Leu Arg Ser Ile Pro Ala
  1               5                  10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence:active
      peptide of ADNF I hsp60-related sequence
```

<400> SEQUENCE: 23

Val Leu Gly Gly Gly Ser Ala Leu Leu Arg Ser Ile Pro Ala
 1               5                  10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence:hsp60
      homolog peptide

<400> SEQUENCE: 24

Val Leu Gly Gly Gly Cys Ala Leu Leu Arg Cys Ile Pro Ala
 1               5                  10

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence:mimic hybrid
      primer

<400> SEQUENCE: 25
acctgcagca aaacaactat tttccatccc tcaacagt                              38

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:cyclophilin
      mRNA upper primer, position 348

<400> SEQUENCE: 26
atggcacagc aggaaagagc                                                  20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:cyclophilin
      mRNA lower primer

<400> SEQUENCE: 27
ttgccggagt cgacaatgat                                                  20

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:sequence of
      p25 clone with structural similarity to active peptide of ADNF I

<400> SEQUENCE: 28

Gly Gly Asn Ala Pro Val Ser Ile Pro
 1               5

<210> SEQ ID NO 29
<211> LENGTH: 837
<212> TYPE: DNA
<213> ORGANISM: Homo sapiens
<220> FEATURE:

<223> OTHER INFORMATION: PCR of human ADNF III cDNA from human
      neuroblastoma, sense

<400> SEQUENCE: 29

| | | | | | |
|---|---|---|---|---|---|
| cattgggccg | acgtcgcatg | ctcccggccg | ccatggccgc | gggattacct | gcagcaaaac | 60 |
| aactatggag | tcaaatctgt | aggccagggt | tacagtgttg | gtcagtcaat | gagactgggt | 120 |
| ctaggtggca | acgcaccagt | ttccattcct | caacaatctc | agtctgtaaa | gcagttactt | 180 |
| ccaagtggaa | acggaaggtc | ttatgggctt | gggtcagagc | agaggtccca | ggcaccagca | 240 |
| agatactccc | tgcagtctgc | taatgcctct | tctctctcat | cgggccagtt | aaagtctcct | 300 |
| tccctctctc | agtcacaggc | atccagagtg | ttaggtcagt | ccagttccaa | acctgctgca | 360 |
| gctgccacag | gccctccccc | aggtaacact | tcctcaactc | aaaagtggaa | aatatgtaca | 420 |
| atctgtaacg | agcaatcact | agtgcggccg | cctgcaggtc | gaccatatgg | gagagctccc | 480 |
| aacgcgttgg | atgcatagct | tgagtattct | atagtgtcac | ctaaatagct | tggcgtaatc | 540 |
| atggtcatag | ctgtttcctg | tgtgaaattg | ttatccgctc | acaattccac | acaacatacg | 600 |
| aaccggaagc | ataaagtgta | aagcctgggg | tgcctaatga | atgagctaac | tcacattaat | 660 |
| tgcgttgcgc | tcactgcccg | ctttccaatc | nggaaactgt | cgtgccaact | gcattaatga | 720 |
| atcggccaac | gcgcggggaa | aagcggtttg | cgtattgggc | gctcttccgc | ttcctcgctc | 780 |
| aatgaatccc | tgcgctcngt | ccttccgntg | cggnnaacgg | tatcactcac | tcnaatt | 837 |

<210> SEQ ID NO 30
<211> LENGTH: 850
<212> TYPE: DNA
<213> ORGANISM: Homo sapiens
<220> FEATURE:
<223> OTHER INFORMATION: PCR of human ADNF III cDNA from human
      neuroblastoma, antisense

<400> SEQUENCE: 30

| | | | | | |
|---|---|---|---|---|---|
| atnnatatca | agctatgcat | ccaacgcgtt | gggagctctc | ccatatggtc | gacctgcagg | 60 |
| cggccgcact | agtgattgct | cgttacagat | tgtacatatt | ttccactttt | gagttgagga | 120 |
| agtgttacct | gggggagggc | ctgtggcagc | tgcagcaggt | ttggaactgg | actgacctaa | 180 |
| cactctggat | gcctgtgact | gagagaggga | aggagacttt | aactggcccg | atgagagaga | 240 |
| agaggcatta | gcagactgca | gggagtatct | tgctggtgcc | tgggacctct | gctctgaccc | 300 |
| aagcccataa | gaccttccgt | ttccacttgg | aagtaactgc | tttacagact | gagattgttg | 360 |
| aggaatggaa | actggtgcgt | tgccacctag | acccagtctc | attgactgac | caacactgta | 420 |
| accctggcct | acagatttga | ctccatagtt | gttttgctgc | aggtaatccc | gcggccatgg | 480 |
| cggccgggag | catgcgacgt | cgggcccaat | tcgccctata | gtgagtcgta | ttacaattca | 540 |
| ctggccgtcg | ttttacaacg | tcgtgactgg | gaaaaccctg | gcgttaccca | acttaatccc | 600 |
| cttgcagcac | atcccccttt | cgccagctgg | cgttaataac | gaagaagccc | gcaccgatcg | 660 |
| cccttcccaa | cagttgcgca | gcctgaatgg | cgaatggacg | cgcctgttag | cgcgcattaa | 720 |
| accccgcggg | tgttgtggtt | acgccgcagc | gtgaccgcta | cacttgccac | ccctaacgc | 780 |
| ccgctccttt | ccctttcttc | cttcctttct | cgccacgtcc | cccgntttcc | ccgtccaact | 840 |
| ctaaatcggt | | | | | | 850 |

<210> SEQ ID NO 31
<211> LENGTH: 787
<212> TYPE: PRT
<213> ORGANISM: Mus musculus -continued

```
<220> FEATURE:
<223> OTHER INFORMATION: mouse activity dependent neurotrophic factor
      III (ADNF III)

<400> SEQUENCE: 31
```

| | | | | | | | | | | | | | | |
|---|---|---|---|---|---|---|---|---|---|---|---|---|---|---|
|Met|Ser|Asn|Val|His|Leu|Gln|Gln|Asn|Asn|Tyr|Gly|Val|Lys|Ser|Val
|1| | | |5| | | | |10| | | | |15|
|Gly|Gln|Ser|Tyr|Gly|Val|Gly|Gln|Ser|Val|Arg|Leu|Gly|Leu|Gly|Gly
| | | |20| | | | |25| | | | |30| | |
|Asn|Ala|Pro|Val|Ser|Ile|Pro|Gln|Gln|Ser|Gln|Ser|Val|Lys|Gln|Leu
| | |35| | | | |40| | | | |45| | | |
|Leu|Pro|Ser|Gly|Asn|Gly|Arg|Ser|Phe|Gly|Leu|Gly|Ala|Glu|Gln|Arg
| |50| | | | |55| | | | |60| | | | |
|Pro|Pro|Ala|Ala|Ala|Arg|Tyr|Ser|Leu|Gln|Thr|Ala|Asn|Thr|Ser|Leu
|65| | | | |70| | | | |75| | | | |80|
|Pro|Pro|Gly|Gln|Val|Lys|Ser|Pro|Ser|Val|Ser|Gln|Ser|Gln|Ala|Ser
| | | | |85| | | | |90| | | | |95| |
|Arg|Val|Leu|Gly|Gln|Ser|Ser|Lys|Pro|Pro|Ala|Ala|Thr|Gly| | |
| | | | |100| | | | |105| | | |110| | |
|Pro|Pro|Pro|Ser|Asn|His|Cys|Ala|Thr|Gln|Lys|Trp|Lys|Ile|Cys|Thr
| | | |115| | | | |120| | | | |125| | |
|Ile|Cys|Asn|Glu|Leu|Phe|Pro|Glu|Asn|Val|Tyr|Ser|Val|His|Phe|Glu
| | |130| | | | |135| | | | |140| | | |
|Lys|Glu|His|Lys|Ala|Glu|Lys|Val|Pro|Ala|Val|Ala|Asn|Tyr|Ile|Met
|145| | | | |150| | | | |155| | | | |160|
|Lys|Ile|His|Asn|Phe|Thr|Ser|Lys|Cys|Leu|Tyr|Cys|Asn|Arg|Tyr|Leu
| | | | |165| | | | |170| | | | |175| |
|Pro|Thr|Asp|Thr|Leu|Leu|Asn|His|Met|Leu|Ile|His|Gly|Leu|Ser|Cys
| | | |180| | | | |185| | | | |190| | |
|Pro|Tyr|Cys|Arg|Ser|Thr|Phe|Asn|Asp|Val|Glu|Lys|Met|Ala|Ala|His
| | |195| | | | |200| | | | |205| | | |
|Met|Arg|Met|Val|His|Ile|Asp|Glu|Glu|Met|Gly|Pro|Lys|Thr|Asp|Ser
| |210| | | | |215| | | | |220| | | | |
|Thr|Leu|Ser|Phe|Asp|Leu|Thr|Leu|Gln|Gln|Gly|Ser|His|Thr|Asn|Ile
|225| | | | |230| | | | |235| | | | |240|
|His|Leu|Leu|Val|Thr|Thr|Tyr|Asn|Leu|Arg|Asp|Ala|Pro|Ala|Glu|Ser
| | | | |245| | | | |250| | | | |255| |
|Val|Ala|Tyr|His|Ala|Gln|Asn|Asn|Ala|Pro|Val|Pro|Lys|Pro|Gln| |
| | | |260| | | | |265| | | | |270| | |
|Pro|Lys|Val|Gln|Glu|Lys|Ala|Asp|Val|Pro|Val|Lys|Ser|Ser|Pro|Gln
| | |275| | | | |280| | | | |285| | | |
|Ala|Ala|Val|Pro|Tyr|Lys|Lys|Asp|Val|Gly|Lys|Thr|Leu|Cys|Pro|Leu
| |290| | | | |295| | | | |300| | | | |
|Cys|Phe|Ser|Ile|Leu|Lys|Gly|Pro|Ile|Ser|Asp|Ala|Leu|Ala|His|His
|305| | | | |310| | | | |315| | | | |320|
|Leu|Arg|Glu|Arg|His|Gln|Val|Ile|Gln|Thr|Val|His|Pro|Val|Glu|Lys
| | | | |325| | | | |330| | | | |335| |
|Lys|Leu|Thr|Tyr|Lys|Cys|Ile|His|Cys|Leu|Gly|Val|Tyr|Thr|Ser|Asn
| | | |340| | | | |345| | | | |350| | |
|Met|Thr|Ala|Ser|Thr|Ile|Thr|Leu|His|Leu|Val|His|Cys|Arg|Gly|Val
| | |355| | | | |360| | | | |365| | | |
|Gly|Lys|Thr|Gln|Asn|Gly|Gln|Asp|Lys|Thr|Asn|Ala|Pro|Ser|Arg|Leu
| |370| | | | |375| | | | |380| | | | |
|Asn|Gln|Ser|Pro|Gly|Leu|Ala|Pro|Val|Lys|Arg|Thr|Tyr|Glu|Gln|Met|

-continued

```
385                 390                 395                 400

Glu Phe Pro Leu Leu Lys Lys Arg Lys Leu Glu Asp Ala Asp Ser
                405                 410                 415

Pro Ser Cys Phe Glu Glu Lys Pro Glu Pro Val Val Leu Ala Leu
                420                 425                 430

Asp Pro Lys Gly His Glu Asp Ser Tyr Glu Ala Arg Lys Ser Phe
                435                 440                 445

Leu Thr Lys Tyr Phe Asn Lys Gln Pro Tyr Pro Thr Arg Arg Glu Ile
450                 455                 460

Glu Lys Leu Ala Ala Ser Leu Trp Leu Trp Lys Ser Asp Ile Ala Ser
465                 470                 475                 480

His Phe Ser Asn Lys Arg Lys Cys Val Arg Asp Cys Glu Lys Tyr
                485                 490                 495

Lys Pro Gly Val Leu Leu Gly Phe Asn Met Lys Glu Leu Asn Lys Val
                500                 505                 510

Lys His Glu Met Asp Phe Asp Ala Glu Trp Leu Phe Glu Asn His Asp
                515                 520                 525

Glu Lys Asp Ser Arg Val Asn Ala Ser Lys Thr Val Asp Lys Lys His
                530                 535                 540

Asn Leu Gly Lys Glu Asp Asp Ser Phe Ser Asp Ser Phe Glu His Leu
545                 550                 555                 560

Glu Glu Glu Ser Asn Gly Ser Gly Ser Pro Phe Asp Pro Val Phe Glu
                565                 570                 575

Val Glu Pro Lys Ile Pro Ser Asp Asn Leu Glu Glu Pro Val Pro Lys
                580                 585                 590

Val Ile Pro Glu Gly Ala Leu Glu Ser Glu Lys Leu Asp Gln Lys Glu
                595                 600                 605

Glu Glu Glu Glu Glu Glu Glu Asp Gly Ser Lys Tyr Glu Thr Ile
                610                 615                 620

His Leu Thr Glu Glu Pro Ala Lys Leu Met His Asp Ala Ser Asp Ser
625                 630                 635                 640

Glu Val Asp Gln Asp Asp Val Val Glu Trp Lys Asp Gly Ala Ser Pro
                645                 650                 655

Ser Glu Ser Gly Pro Gly Ser Gln Gln Ile Ser Asp Phe Glu Asp Asn
                660                 665                 670

Thr Cys Glu Met Lys Pro Gly Thr Trp Ser Asp Glu Ser Ser Gln Ser
                675                 680                 685

Glu Asp Ala Arg Ser Ser Lys Pro Ala Ala Lys Lys Ala Thr Val
                690                 695                 700

Gln Asp Asp Thr Glu Gln Leu Lys Trp Lys Asn Ser Ser Tyr Gly Lys
705                 710                 715                 720

Val Glu Gly Phe Trp Ser Lys Asp Gln Ser Gln Trp Glu Asn Ala Ser
                725                 730                 735

Glu Asn Ala Glu Arg Leu Pro Asn Pro Gln Ile Glu Trp Gln Asn Ser
                740                 745                 750

Thr Ile Asp Ser Glu Asp Gly Glu Gln Phe Asp Ser Met Thr Asp Gly
                755                 760                 765

Val Ala Asp Pro Met His Gly Ser Leu Thr Gly Val Lys Leu Ser Ser
                770                 775                 780

Gln Gln Ala
785

<210> SEQ ID NO 32
```

-continued

```
<211> LENGTH: 781
<212> TYPE: PRT
<213> ORGANISM: Homo sapiens
<220> FEATURE:
<223> OTHER INFORMATION: human activity dependent neurotrophic factor
      III (ADNF III)

<400> SEQUENCE: 32

Met Ser Ser Val His Leu Gln Gln Asn Asn Tyr Gly Val Lys Ser Val
 1               5                  10                  15

Gly Gln Gly Tyr Ser Val Gly Gln Ser Met Arg Leu Gly Leu Gly Gly
                20                  25                  30

Asn Ala Pro Val Ser Ile Pro Gln Gln Ser Gln Ser Val Lys Gln Leu
            35                  40                  45

Leu Pro Ser Gly Asn Gly Arg Ser Tyr Gly Leu Gly Ser Glu Gln Arg
    50                  55                  60

Ser Gln Ala Pro Ala Arg Tyr Ser Leu Gln Ser Ala Asn Ala Ser Ser
65                  70                  75                  80

Leu Ser Ser Gly His Leu Lys Ser Pro Ser Leu Ser His Ser Gln Ala
                85                  90                  95

Ser Arg Val Leu Gly Gln Ser Ser Lys Pro Ala Ala Ala Thr
                100                 105                 110

Gly Pro Pro Gly Asn Thr Ser Ser Thr Gln Lys Trp Lys Ile Cys
            115                 120                 125

Thr Ile Cys Asn Glu Leu Phe Pro Glu Asn Val Tyr Ser Val His Phe
    130                 135                 140

Glu Lys Glu His Lys Ala Glu Lys Val Pro Ala Val Ala Asn Tyr Ile
145                 150                 155                 160

Met Lys Ile His Asn Phe Thr Ser Lys Cys Leu Tyr Cys Asn Arg Tyr
                165                 170                 175

Leu Pro Thr Asp Thr Leu Leu Asn His Met Leu Ile His Gly Leu Ser
            180                 185                 190

Cys Pro Tyr Cys Arg Ser Thr Phe Asn Asp Val Glu Lys Met Ala Ala
        195                 200                 205

His Met Arg Met Val His Ile Asp Glu Glu Met Gly Pro Lys Thr Asp
    210                 215                 220

Ser Thr Leu Ser Phe Asp Leu Thr Leu Gln Gly Ser His Thr Asn
225                 230                 235                 240

Ile His Leu Leu Val Thr Thr Tyr Asn Leu Arg Asp Ala Pro Ala Glu
                245                 250                 255

Ser Val Ala Tyr His Ala Gln Asn Asn Pro Val Pro Pro Lys Pro
            260                 265                 270

Gln Pro Lys Val Gln Glu Lys Ala Asp Ile Pro Val Lys Ser Ser Pro
    275                 280                 285

Gln Ala Ala Val Pro Tyr Lys Leu Asp Val Gly Lys Thr Leu Cys Pro
290                 295                 300

Leu Cys Phe Ser Ile Leu Lys Gly Pro Ile Ser Asp Ala Leu Ala His
305                 310                 315                 320

His Leu Arg Glu Arg His Gln Val Ile Gln Thr Val His Pro Val Glu
                325                 330                 335

Lys Lys Leu Thr Tyr Lys Cys Ile His Cys Leu Gly Val Tyr Thr Ser
            340                 345                 350

Asn Met Thr Ala Ser Thr Ile Thr Leu His Leu Val His Cys Arg Gly
        355                 360                 365

Val Gly Lys Thr Gln Asn Gly Gln Asp Lys Thr Asn Ala Pro Ser Arg
```

```
             370                 375                 380
Leu Asn Gln Ser Pro Ser Leu Ala Pro Val Lys Arg Thr Tyr Glu Gln
385                 390                 395                 400
Met Glu Phe Pro Leu Leu Lys Lys Arg Lys Leu Asp Asp Ser Asp
                405                 410                 415
Ser Pro Ser Phe Phe Glu Glu Lys Pro Glu Glu Pro Val Val Leu Ala
                420                 425                 430
Leu Asp Pro Lys Gly His Glu Asp Asp Ser Tyr Glu Ala Arg Lys Ser
                435                 440                 445
Phe Leu Thr Lys Tyr Phe Asn Lys Gln Pro Tyr Pro Thr Arg Arg Glu
    450                 455                 460
Ile Glu Lys Leu Ala Ala Ser Leu Trp Leu Trp Lys Ser Asp Ile Ala
465                 470                 475                 480
Ser His Phe Ser Asn Lys Arg Lys Lys Cys Val Arg Asp Cys Glu Lys
                485                 490                 495
Tyr Lys Pro Gly Val Leu Leu Gly Phe Asn Met Lys Glu Leu Asn Lys
                500                 505                 510
Val Lys His Glu Met Asp Phe Asp Ala Glu Trp Leu Phe Glu Asn His
                515                 520                 525
Asp Glu Lys Asp Ser Arg Val Asn Ala Ser Lys Thr Ala Asp Lys Lys
                530                 535                 540
Leu Asn Leu Gly Lys Glu Asp Asp Ser Ser Asp Ser Phe Glu Asn
545                 550                 555                 560
Leu Glu Glu Glu Ser Asn Glu Ser Gly Ser Pro Phe Asp Pro Val Phe
                565                 570                 575
Glu Val Glu Pro Lys Ile Ser Asn Asp Asn Pro Glu Glu His Val Leu
                580                 585                 590
Lys Val Ile Pro Glu Asp Ala Ser Glu Ser Glu Glu Lys Leu Asp Gln
                595                 600                 605
Lys Glu Asp Gly Ser Lys Tyr Glu Thr Ile His Leu Thr Glu Glu Pro
                610                 615                 620
Thr Lys Leu Met His Asn Ala Ser Asp Ser Glu Val Asp Gln Asp Asp
625                 630                 635                 640
Val Val Glu Trp Lys Asp Gly Ala Ser Pro Ser Glu Ser Gly Pro Gly
                645                 650                 655
Ser Gln Gln Val Ser Asp Phe Glu Asp Asn Thr Cys Glu Met Lys Pro
                660                 665                 670
Gly Thr Trp Ser Asp Glu Ser Gln Ser Glu Asp Ala Arg Ser Ser
                675                 680                 685
Lys Pro Ala Ala Lys Lys Ala Thr Met Gln Gly Asp Arg Glu Gln
690                 695                 700
Leu Lys Trp Lys Asn Ser Ser Tyr Gly Lys Val Glu Gly Phe Trp Ser
705                 710                 715                 720
Lys Asp Gln Ser Gln Trp Lys Asn Ala Ser Glu Asn Asp Glu Arg Leu
                725                 730                 735
Ser Asn Pro Gln Ile Glu Trp Gln Asn Ser Thr Ile Asp Ser Glu Asp
                740                 745                 750
Gly Glu Gln Phe Asp Asn Met Thr Asp Gly Val Thr Glu Pro Met His
                755                 760                 765
Gly Ser Leu Ala Gly Val Lys Leu Ser Ser Gln Gln Ala
                770                 775                 780
```

<210> SEQ ID NO 33

```
<211> LENGTH: 10
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 33

Gly Gly Asn Ala Pro Val Ser Ile Pro Gln
  1               5                  10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 34

Leu Gly Gly Asn Ala Pro Val Ser Ile Pro Gln Gln Ser
  1               5                  10

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 35

Leu Gly Leu Gly Gly Asn Ala Pro Val Ser Ile Pro Gln Gln Ser
  1               5                  10                  15

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence:ADNF-9
      active peptide adsorbed onto bovine serum albumin (BSA) as antigen

<400> SEQUENCE: 36

Ser Ala Leu Leu Arg Ser Ile Pro Ala
  1               5

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence:ADNF
      I/PIF1-related sequence

<400> SEQUENCE: 37

Ile Gln Leu Glu Thr Glu Ile Gln Glu Lys Gln Ile Ile
  1               5                  10

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence:cyclophilin
      mRNA mimic primer

<400> SEQUENCE: 38
```

```
atggcacagg aggaaagagc aatgcaggca aagacacc                                    38
```

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence:neuropeptide
      cleavage site

<400> SEQUENCE: 39

Lys Lys Arg Lys
 1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence:neuropeptide
      cleavage site

<400> SEQUENCE: 40

Lys Arg Lys Lys
 1

<210> SEQ ID NO 41
<211> LENGTH: 800
<212> TYPE: PRT
<213> ORGANISM: Homo sapiens
<220> FEATURE:
<221> NAME/KEY: PEPTIDE
<222> LOCATION: (1)..(800)
<223> OTHER INFORMATION: translation of H3' human ADNF III cDNA clone

<400> SEQUENCE: 41

Met Val Asn Arg Leu Ser Ile Pro Lys Pro Asn Leu Asn Ser Thr Gly
 1               5                  10                  15

Val Asn Met Met Ser Ser Val His Leu Gln Gln Asn Asn Tyr Gly Val
                20                  25                  30

Lys Ser Val Gly Gln Gly Tyr Ser Val Gly Gln Ser Met Arg Leu Gly
            35                  40                  45

Leu Gly Gly Asn Ala Pro Val Ser Ile Pro Gln Gln Ser Gln Ser Val
        50                  55                  60

Lys Gln Leu Leu Pro Ser Gly Asn Gly Arg Ser Tyr Gly Leu Gly Ser
 65                  70                  75                  80

Glu Gln Arg Ser Gln Ala Pro Ala Arg Tyr Ser Leu Gln Ser Ala Asn
                85                  90                  95

Ala Ser Ser Leu Ser Ser Gly His Leu Lys Ser Pro Ser Leu Ser His
            100                 105                 110

Ser Gln Ala Ser Arg Val Leu Gly Gln Ser Ser Ser Lys Pro Ala Ala
        115                 120                 125

Ala Ala Thr Gly Pro Pro Pro Gly Asn Thr Ser Thr Gln Lys Trp
    130                 135                 140

Lys Ile Cys Thr Ile Cys Asn Glu Leu Phe Pro Glu Asn Val Tyr Ser
145                 150                 155                 160

Val His Phe Glu Lys Glu His Lys Ala Glu Lys Val Pro Ala Val Ala
                165                 170                 175

Asn Tyr Ile Met Lys Ile His Asn Phe Thr Ser Lys Cys Leu Tyr Cys
            180                 185                 190

Asn Arg Tyr Leu Pro Thr Asp Thr Leu Leu Asn His Met Leu Ile His

-continued

```
            195                 200                 205
Gly Leu Ser Cys Pro Tyr Cys Arg Ser Thr Phe Asn Asp Val Glu Lys
            210                 215                 220

Met Ala Ala His Met Arg Met Val His Ile Asp Glu Met Gly Pro
225                 230                 235                 240

Lys Thr Asp Ser Thr Leu Ser Phe Asp Leu Thr Leu Gln Gln Gly Ser
                245                 250                 255

His Thr Asn Ile His Leu Leu Val Thr Thr Tyr Asn Leu Arg Asp Ala
                260                 265                 270

Pro Ala Glu Ser Val Ala Tyr His Ala Gln Asn Asn Pro Val Pro
                275                 280                 285

Pro Lys Pro Gln Pro Lys Val Gln Glu Lys Ala Asp Ile Pro Val Lys
            290                 295                 300

Ser Ser Pro Gln Ala Ala Val Pro Tyr Lys Lys Asp Val Gly Lys Thr
305                 310                 315                 320

Leu Cys Pro Leu Cys Phe Ser Ile Leu Lys Gly Pro Ile Ser Asp Ala
                325                 330                 335

Leu Ala His His Leu Arg Glu Arg His Gln Val Ile Gln Thr Val His
            340                 345                 350

Pro Val Glu Lys Lys Leu Thr Tyr Lys Cys Ile His Cys Leu Gly Val
            355                 360                 365

Tyr Thr Ser Asn Met Thr Ala Ser Thr Ile Thr Leu His Leu Val His
370                 375                 380

Cys Arg Gly Val Gly Lys Thr Gln Asn Gly Gln Asp Lys Thr Asn Ala
385                 390                 395                 400

Pro Ser Arg Leu Asn Gln Ser Pro Ser Leu Ala Pro Val Lys Arg Thr
                405                 410                 415

Tyr Glu Gln Met Glu Phe Pro Leu Leu Lys Lys Arg Lys Leu Asp Asp
            420                 425                 430

Asp Ser Asp Ser Pro Ser Phe Phe Glu Glu Lys Pro Glu Glu Pro Val
            435                 440                 445

Val Leu Ala Leu Asp Pro Lys Gly His Glu Asp Asp Ser Tyr Glu Ala
            450                 455                 460

Arg Lys Ser Phe Leu Thr Lys Tyr Phe Asn Lys Gln Pro Tyr Pro Thr
465                 470                 475                 480

Arg Arg Glu Ile Glu Lys Leu Ala Ala Ser Leu Trp Leu Trp Lys Ser
                485                 490                 495

Asp Ile Ala Ser His Phe Ser Asn Lys Arg Lys Lys Cys Val Arg Asp
                500                 505                 510

Cys Glu Lys Tyr Lys Pro Gly Val Leu Leu Gly Phe Asn Met Lys Glu
            515                 520                 525

Leu Asn Lys Val Lys His Glu Met Asp Phe Asp Ala Glu Trp Leu Phe
            530                 535                 540

Glu Asn His Asp Glu Lys Asp Ser Arg Val Asn Ala Ser Lys Thr Ala
545                 550                 555                 560

Asp Lys Lys Leu Asn Leu Gly Lys Glu Asp Ser Ser Ser Asp Ser
                565                 570                 575

Phe Glu Asn Leu Glu Glu Glu Ser Asn Glu Ser Gly Ser Pro Phe Asp
                580                 585                 590

Pro Val Phe Glu Val Glu Pro Lys Ile Ser Asn Asp Asn Pro Glu Glu
            595                 600                 605

His Val Leu Lys Val Ile Pro Glu Asp Ala Ser Glu Ser Glu Glu Lys
            610                 615                 620
```

```
Leu Asp Gln Lys Glu Asp Gly Ser Lys Tyr Glu Thr Ile His Leu Thr
625                 630                 635                 640

Glu Glu Pro Thr Lys Leu Met His Asn Ala Ser Asp Ser Glu Val Asp
                645                 650                 655

Gln Asp Asp Val Val Glu Trp Lys Asp Gly Ala Ser Pro Ser Glu Ser
            660                 665                 670

Gly Pro Gly Ser Gln Gln Val Ser Asp Phe Glu Asp Asn Thr Cys Glu
        675                 680                 685

Met Lys Pro Gly Thr Trp Ser Asp Glu Ser Ser Gln Ser Glu Asp Ala
    690                 695                 700

Arg Ser Ser Lys Pro Ala Ala Lys Lys Ala Thr Met Gln Gly Asp
705                 710                 715                 720

Arg Glu Gln Leu Lys Trp Lys Asn Ser Ser Tyr Gly Lys Val Glu Gly
                725                 730                 735

Phe Trp Ser Lys Asp Gln Ser Gln Trp Lys Asn Ala Ser Glu Asn Asp
            740                 745                 750

Glu Arg Leu Ser Asn Pro Gln Ile Glu Trp Gln Asn Ser Thr Ile Asp
        755                 760                 765

Ser Glu Asp Gly Glu Gln Phe Asp Asn Met Thr Asp Gly Val Thr Glu
    770                 775                 780

Pro Met His Gly Ser Leu Ala Gly Val Lys Leu Ser Ser Gln Gln Ala
785                 790                 795                 800

<210> SEQ ID NO 42
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: translation of H3' human ADNF III cDNA clone

<400> SEQUENCE: 42

Val Pro Gly Ser Leu Ala Leu Val Thr Cys Cys Ser Leu Glu Leu
 1               5                  10                  15

<210> SEQ ID NO 43
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: translation of H3' human ADNF III cDNA clone

<400> SEQUENCE: 43

Leu Gln Ser Cys Leu Leu Thr Gly Thr Ala Leu
 1               5                  10

<210> SEQ ID NO 44
<211> LENGTH: 20
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: translation of H3' human ADNF III cDNA clone

<400> SEQUENCE: 44

Val Leu Val Gly Leu Trp Gly Met Trp Pro Leu Gln Phe Gln Trp Leu
 1               5                  10                  15
```

```
Phe Leu Ser Leu
            20

<210> SEQ ID NO 45
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: translation of H3' human ADNF III cDNA clone

<400> SEQUENCE: 45

Gln Asp Arg Leu Phe Leu Leu Gln Asn Leu Leu
 1               5                  10

<210> SEQ ID NO 46
<211> LENGTH: 6
<212> TYPE: PRT
<213> ORGANISM: Homo sapiens
<220> FEATURE:
<221> NAME/KEY: PEPTIDE
<222> LOCATION: (1)..(6)
<223> OTHER INFORMATION: translation of H3' human ADNF III cDNA clone

<400> SEQUENCE: 46

Leu Asn Val Lys Asn Gln
 1               5

<210> SEQ ID NO 47
<211> LENGTH: 4
<212> TYPE: PRT
<213> ORGANISM: Homo sapiens
<220> FEATURE:
<221> NAME/KEY: PEPTIDE
<222> LOCATION: (1)..(4)
<223> OTHER INFORMATION: translation of H3' human ADNF III cDNA clone

<400> SEQUENCE: 47

Ala Gly Asp Ser
 1

<210> SEQ ID NO 48
<211> LENGTH: 39
<212> TYPE: PRT
<213> ORGANISM: Homo sapiens
<220> FEATURE:
<221> NAME/KEY: PEPTIDE
<222> LOCATION: (1)..(39)
<223> OTHER INFORMATION: translation of H3' human ADNF III cDNA clone

<400> SEQUENCE: 48

Ile Leu Thr Arg Lys Ser Arg Gly Leu Phe Leu Ser Ala Phe Ser Thr
 1               5                  10                  15

Phe Leu Ser Leu Cys Glu Met Ile Gly Gln Met Ser Leu Arg Ser Val
            20                  25                  30

Lys Leu Ile His Met Val Val
        35

<210> SEQ ID NO 49
<211> LENGTH: 25
<212> TYPE: PRT
<213> ORGANISM: Homo sapiens
<220> FEATURE:
<221> NAME/KEY: PEPTIDE
<222> LOCATION: (1)..(25)
<223> OTHER INFORMATION: translation of H3' human ADNF III cDNA clone
```

-continued

<400> SEQUENCE: 49

Gly Gln His Thr Ser Tyr Gln Ser Asn Val Tyr Ser Arg Leu Trp Glu
1               5                   10                  15

Lys Arg Phe Phe Phe Met Tyr Ser Phe
            20                  25

<210> SEQ ID NO 50
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: translation of H3' human ADNF III cDNA clone

<400> SEQUENCE: 50

Ile Val Glu Met Tyr Ile Cys Thr Val Phe
1               5                   10

<210> SEQ ID NO 51
<211> LENGTH: 4
<212> TYPE: PRT
<213> ORGANISM: Homo sapiens
<220> FEATURE:
<221> NAME/KEY: PEPTIDE
<222> LOCATION: (1)..(4)
<223> OTHER INFORMATION: translation of H3' human ADNF III cDNA clone

<400> SEQUENCE: 51

Thr Tyr Ser Lys
1

<210> SEQ ID NO 52
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: translation of H3' human ADNF III cDNA clone

<400> SEQUENCE: 52

Ser Cys Tyr Cys Val Pro Ile Ile Asp Phe Phe Phe
1               5                   10

<210> SEQ ID NO 53
<211> LENGTH: 20
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: translation of H3' human ADNF III cDNA clone

<400> SEQUENCE: 53

Cys Cys Pro Cys Cys Val Ile Asn Ala Leu Ser Ser Leu Pro Ser Lys
1               5                   10                  15

Ser Ser Lys Leu
            20

<210> SEQ ID NO 54
<211> LENGTH: 2487
<212> TYPE: DNA
<213> ORGANISM: Mus musculus
<220> FEATURE:
<221> NAME/KEY: CDS
<222> LOCATION: (1)..(2487)

<223> OTHER INFORMATION: an additional mouse activity dependent
      neurotrophic factor III (ADNF III) cDNA clone

<400> SEQUENCE: 54

| | | | | | | | | | | | | | | | | |
|---|---|---|---|---|---|---|---|---|---|---|---|---|---|---|---|---|
| atg | gga | ctc | cca | cca | cga | atc | agc | tcc | ctt | gct | tct | gga | aat | gtc | cgg | 48 |
| Met | Gly | Leu | Pro | Pro | Arg | Ile | Ser | Ser | Leu | Ala | Ser | Gly | Asn | Val | Arg | |
| 1 | | | | 5 | | | | | 10 | | | | | 15 | | |

| tcg | ttg | cca | tca | cag | cag | atg | gta | aac | cga | ttg | tca | ata | cca | aag | ccc | 96 |
|---|---|---|---|---|---|---|---|---|---|---|---|---|---|---|---|---|
| Ser | Leu | Pro | Ser | Gln | Gln | Met | Val | Asn | Arg | Leu | Ser | Ile | Pro | Lys | Pro | |
| | | | 20 | | | | | 25 | | | | | 30 | | | |

| aac | tta | aat | tca | acg | gga | gtc | aac | atg | atg | tcc | aat | gtt | cac | ctg | cag | 144 |
|---|---|---|---|---|---|---|---|---|---|---|---|---|---|---|---|---|
| Asn | Leu | Asn | Ser | Thr | Gly | Val | Asn | Met | Met | Ser | Asn | Val | His | Leu | Gln | |
| | | 35 | | | | | 40 | | | | | 45 | | | | |

| caa | aac | aac | tat | gga | gtc | aaa | tct | gtg | ggc | cag | agc | tat | ggt | gtt | ggc | 192 |
|---|---|---|---|---|---|---|---|---|---|---|---|---|---|---|---|---|
| Gln | Asn | Asn | Tyr | Gly | Val | Lys | Ser | Val | Gly | Gln | Ser | Tyr | Gly | Val | Gly | |
| 50 | | | | | 55 | | | | | 60 | | | | | | |

| cag | tca | gtg | agg | ctg | gga | cta | ggt | ggc | aat | gct | cca | gtt | tcc | atc | cct | 240 |
|---|---|---|---|---|---|---|---|---|---|---|---|---|---|---|---|---|
| Gln | Ser | Val | Arg | Leu | Gly | Leu | Gly | Gly | Asn | Ala | Pro | Val | Ser | Ile | Pro | |
| 65 | | | | | 70 | | | | | 75 | | | | | 80 | |

| caa | cag | tct | cag | tcc | gtg | aaa | cag | tta | ctt | cca | agt | ggg | aat | ggg | agg | 288 |
|---|---|---|---|---|---|---|---|---|---|---|---|---|---|---|---|---|
| Gln | Gln | Ser | Gln | Ser | Val | Lys | Gln | Leu | Leu | Pro | Ser | Gly | Asn | Gly | Arg | |
| | | | | 85 | | | | | 90 | | | | | 95 | | |

| tct | ttt | ggg | cta | ggt | gct | gag | cag | agg | ccc | cca | gca | gca | gcc | agg | tac | 336 |
|---|---|---|---|---|---|---|---|---|---|---|---|---|---|---|---|---|
| Ser | Phe | Gly | Leu | Gly | Ala | Glu | Gln | Arg | Pro | Pro | Ala | Ala | Ala | Arg | Tyr | |
| | | | 100 | | | | | 105 | | | | | 110 | | | |

| tcc | ctg | cag | act | gcc | aac | acc | tct | cta | ccc | cca | ggc | caa | gtg | aag | tct | 384 |
|---|---|---|---|---|---|---|---|---|---|---|---|---|---|---|---|---|
| Ser | Leu | Gln | Thr | Ala | Asn | Thr | Ser | Leu | Pro | Pro | Gly | Gln | Val | Lys | Ser | |
| | | 115 | | | | | 120 | | | | | 125 | | | | |

| ccc | tct | gtg | tct | cag | tca | cag | gca | tct | aga | gta | tta | ggt | cag | tcc | agt | 432 |
|---|---|---|---|---|---|---|---|---|---|---|---|---|---|---|---|---|
| Pro | Ser | Val | Ser | Gln | Ser | Gln | Ala | Ser | Arg | Val | Leu | Gly | Gln | Ser | Ser | |
| 130 | | | | | 135 | | | | | 140 | | | | | | |

| tct | aaa | cct | cca | cca | gcc | gcc | aca | ggc | cct | cct | cca | agc | aac | cac | tgt | 480 |
|---|---|---|---|---|---|---|---|---|---|---|---|---|---|---|---|---|
| Ser | Lys | Pro | Pro | Pro | Ala | Ala | Thr | Gly | Pro | Pro | Pro | Ser | Asn | His | Cys | |
| 145 | | | | | 150 | | | | | 155 | | | | | 160 | |

| gcc | act | cag | aag | tgg | aaa | atc | tgt | aca | atc | tgt | aac | gag | ctt | ttc | cct | 528 |
|---|---|---|---|---|---|---|---|---|---|---|---|---|---|---|---|---|
| Ala | Thr | Gln | Lys | Trp | Lys | Ile | Cys | Thr | Ile | Cys | Asn | Glu | Leu | Phe | Pro | |
| | | | | 165 | | | | | 170 | | | | | 175 | | |

| gag | aat | gtc | tat | agc | gtt | cac | ttc | gaa | aag | gag | cat | aaa | gct | gag | aaa | 576 |
|---|---|---|---|---|---|---|---|---|---|---|---|---|---|---|---|---|
| Glu | Asn | Val | Tyr | Ser | Val | His | Phe | Glu | Lys | Glu | His | Lys | Ala | Glu | Lys | |
| | | | 180 | | | | | 185 | | | | | 190 | | | |

| gtc | cca | gcc | gta | gct | aac | tac | att | atg | aaa | ata | cac | aat | ttt | act | agc | 624 |
|---|---|---|---|---|---|---|---|---|---|---|---|---|---|---|---|---|
| Val | Pro | Ala | Val | Ala | Asn | Tyr | Ile | Met | Lys | Ile | His | Asn | Phe | Thr | Ser | |
| | | 195 | | | | | 200 | | | | | 205 | | | | |

| aaa | tgc | ctc | tac | tgt | aat | cgc | tat | ttg | cct | aca | gat | acc | cta | ctc | aac | 672 |
|---|---|---|---|---|---|---|---|---|---|---|---|---|---|---|---|---|
| Lys | Cys | Leu | Tyr | Cys | Asn | Arg | Tyr | Leu | Pro | Thr | Asp | Thr | Leu | Leu | Asn | |
| 210 | | | | | 215 | | | | | 220 | | | | | | |

| cat | atg | tta | att | cat | ggt | ctg | tct | tgt | ccg | tat | tgc | cgt | tcc | acc | ttc | 720 |
|---|---|---|---|---|---|---|---|---|---|---|---|---|---|---|---|---|
| His | Met | Leu | Ile | His | Gly | Leu | Ser | Cys | Pro | Tyr | Cys | Arg | Ser | Thr | Phe | |
| 225 | | | | | 230 | | | | | 235 | | | | | 240 | |

| aat | gat | gta | gag | aag | atg | gca | gca | cac | atg | cga | atg | gtt | cat | att | gat | 768 |
|---|---|---|---|---|---|---|---|---|---|---|---|---|---|---|---|---|
| Asn | Asp | Val | Glu | Lys | Met | Ala | Ala | His | Met | Arg | Met | Val | His | Ile | Asp | |
| | | | | 245 | | | | | 250 | | | | | 255 | | |

| gaa | gag | atg | ggg | cct | aaa | acg | gat | tct | act | ttg | agc | ttt | gat | ttg | aca | 816 |
|---|---|---|---|---|---|---|---|---|---|---|---|---|---|---|---|---|
| Glu | Glu | Met | Gly | Pro | Lys | Thr | Asp | Ser | Thr | Leu | Ser | Phe | Asp | Leu | Thr | |
| | | | 260 | | | | | 265 | | | | | 270 | | | |

| ttg | caa | cag | ggc | agt | cac | acc | aac | att | cat | ctc | ctg | gtg | acc | aca | tac | 864 |
|---|---|---|---|---|---|---|---|---|---|---|---|---|---|---|---|---|
| Leu | Gln | Gln | Gly | Ser | His | Thr | Asn | Ile | His | Leu | Leu | Val | Thr | Thr | Tyr | |
| | | 275 | | | | | 280 | | | | | 285 | | | | |

| aac | ctg | agg | gat | gcc | ccg | gct | gaa | tca | gtt | gct | tac | cat | gcc | caa | aat | 912 |
|---|---|---|---|---|---|---|---|---|---|---|---|---|---|---|---|---|
| Asn | Leu | Arg | Asp | Ala | Pro | Ala | Glu | Ser | Val | Ala | Tyr | His | Ala | Gln | Asn | |

```
              290                 295                 300
aat gcc cca gtt cct cca aag cca caa cca aaa gtt cag gaa aaa gca      960
Asn Ala Pro Val Pro Pro Lys Pro Gln Pro Lys Val Gln Glu Lys Ala
305                 310                 315                 320 gat gtc ccg gtt aaa agt tca cct caa gct gca gtg ccc tat aaa aaa     1008
Asp Val Pro Val Lys Ser Ser Pro Gln Ala Ala Val Pro Tyr Lys Lys
                325                 330                 335 gat gtt ggg aag acc ctt tgc cct ctt tgc ttt tca ata cta aaa gga     1056
Asp Val Gly Lys Thr Leu Cys Pro Leu Cys Phe Ser Ile Leu Lys Gly
                340                 345                 350 ccc ata tct gat gca ctt gca cat cat tta cga gaa aga cac caa gtt     1104
Pro Ile Ser Asp Ala Leu Ala His His Leu Arg Glu Arg His Gln Val
            355                 360                 365 att cag aca gtt cat ccg gtt gag aaa aag cta act tac aaa tgt atc     1152
Ile Gln Thr Val His Pro Val Glu Lys Lys Leu Thr Tyr Lys Cys Ile
370                 375                 380 cat tgc ctt ggt gtg tat act agc aac atg aca gcc tca acc atc act     1200
His Cys Leu Gly Val Tyr Thr Ser Asn Met Thr Ala Ser Thr Ile Thr
385                 390                 395                 400 ctg cat cta gtc cac tgc agg ggt gtt gga aaa acc cag aat ggc cag     1248
Leu His Leu Val His Cys Arg Gly Val Gly Lys Thr Gln Asn Gly Gln
                405                 410                 415 gac aag aca aac gca cct tct cgg ctc aat cag tct cca ggc ctg gcc     1296
Asp Lys Thr Asn Ala Pro Ser Arg Leu Asn Gln Ser Pro Gly Leu Ala
                420                 425                 430 cct gtg aag cgc acg tat gag cag atg gag ttt cca ctg cta aaa aag     1344
Pro Val Lys Arg Thr Tyr Glu Gln Met Glu Phe Pro Leu Leu Lys Lys
            435                 440                 445 cgg aag ctg gag gag gat gct gat tcc cct agc tgc ttt gaa gag aag     1392
Arg Lys Leu Glu Glu Asp Ala Asp Ser Pro Ser Cys Phe Glu Glu Lys
450                 455                 460 cca gaa gag cct gtt gtt tta gct tta gac ccc aag ggt cat gaa gat     1440
Pro Glu Glu Pro Val Val Leu Ala Leu Asp Pro Lys Gly His Glu Asp
465                 470                 475                 480 gat tct tat gag gct agg aaa agc ttt ctc aca aag tac ttc aac aaa     1488
Asp Ser Tyr Glu Ala Arg Lys Ser Phe Leu Thr Lys Tyr Phe Asn Lys
                485                 490                 495 cag ccc tat ccc acc agg aga gaa att gag aag tta gct gcc agt cta     1536
Gln Pro Tyr Pro Thr Arg Arg Glu Ile Glu Lys Leu Ala Ala Ser Leu
                500                 505                 510 tgg cta tgg aag agt gac att gcc tcc cat ttc agt aac aag agg aag     1584
Trp Leu Trp Lys Ser Asp Ile Ala Ser His Phe Ser Asn Lys Arg Lys
            515                 520                 525 aag tgt gtc cgc gac tgt gaa aag tac aag cct ggt gtg ctc cta ggt     1632
Lys Cys Val Arg Asp Cys Glu Lys Tyr Lys Pro Gly Val Leu Leu Gly
530                 535                 540 ttt aac atg aaa gaa tta aat aaa gtc aaa cac gag atg gat ttt gat     1680
Phe Asn Met Lys Glu Leu Asn Lys Val Lys His Glu Met Asp Phe Asp
545                 550                 555                 560 gct gag tgg ctg ttt gaa aat cac gat gag aaa gac tca aga gtc aat     1728
Ala Glu Trp Leu Phe Glu Asn His Asp Glu Lys Asp Ser Arg Val Asn
                565                 570                 575 gct agc aag act gtt gac aaa aag cat aac ctt ggg aaa gaa gat gat     1776
Ala Ser Lys Thr Val Asp Lys Lys His Asn Leu Gly Lys Glu Asp Asp
                580                 585                 590 agc ttc tca gat agt ttt gaa cat ttg gaa gaa gaa tcc aat gga agc     1824
Ser Phe Ser Asp Ser Phe Glu His Leu Glu Glu Glu Ser Asn Gly Ser
            595                 600                 605 ggg agt cct ttt gac cct gtc ttt gaa gtt gag cct aaa att ccc agt     1872
```

-continued

```
Gly Ser Pro Phe Asp Pro Val Phe Glu Val Glu Pro Lys Ile Pro Ser
        610                 615                 620 gat aat tta gag gag cct gta ccg aag gtt att ccg gaa ggt gct ttg      1920
Asp Asn Leu Glu Glu Pro Val Pro Lys Val Ile Pro Glu Gly Ala Leu
625                 630                 635                 640 gaa tct gag aag cta gac caa aaa gag gag gag gag gag gag gag         1968
Glu Ser Glu Lys Leu Asp Gln Lys Glu Glu Glu Glu Glu Glu Glu
                645                 650                 655 gag gat ggt tca aaa tat gaa act atc cat ttg act gag gaa cca gcc     2016
Glu Asp Gly Ser Lys Tyr Glu Thr Ile His Leu Thr Glu Glu Pro Ala
            660                 665                 670 aaa tta atg cat gat gcc tct gat agt gag gta gac caa gat gat gta     2064
Lys Leu Met His Asp Ala Ser Asp Ser Glu Val Asp Gln Asp Asp Val
675                 680                 685 gtt gag tgg aaa gat ggt gct tca cca tct gag agt ggg cct ggt tcc     2112
Val Glu Trp Lys Asp Gly Ala Ser Pro Ser Glu Ser Gly Pro Gly Ser
690                 695                 700 caa caa atc tca gac ttt gag gat aat aca tgt gaa atg aaa cca gga     2160
Gln Gln Ile Ser Asp Phe Glu Asp Asn Thr Cys Glu Met Lys Pro Gly
705                 710                 715                 720 acc tgg tct gat gag tct tcc cag agt gaa gat gca agg agc agt aag     2208
Thr Trp Ser Asp Glu Ser Ser Gln Ser Glu Asp Ala Arg Ser Ser Lys
                725                 730                 735 cca gct gcc aaa aaa aag gct aca gtg caa gat gac aca gag cag tta     2256
Pro Ala Ala Lys Lys Lys Ala Thr Val Gln Asp Asp Thr Glu Gln Leu
            740                 745                 750 aaa tgg aag aat agt tcc tat gga aaa gtt gaa ggg ttt tgg tcc aag     2304
Lys Trp Lys Asn Ser Ser Tyr Gly Lys Val Glu Gly Phe Trp Ser Lys
755                 760                 765 gac cag tca cag tgg gaa aat gca tct gag aat gca gag cgc tta cca     2352
Asp Gln Ser Gln Trp Glu Asn Ala Ser Glu Asn Ala Glu Arg Leu Pro
770                 775                 780 aac cca cag att gag tgg cag aat agc aca att gac agt gag gac ggg     2400
Asn Pro Gln Ile Glu Trp Gln Asn Ser Thr Ile Asp Ser Glu Asp Gly
785                 790                 795                 800 gag cac ttt gac agc atg act gac gga gtt gct gat ccc atg cat ggc     2448
Glu His Phe Asp Ser Met Thr Asp Gly Val Ala Asp Pro Met His Gly
                805                 810                 815 agc tta act gga gtg aag ctg agc agc cag caa gcc tga               2487
Ser Leu Thr Gly Val Lys Leu Ser Ser Gln Gln Ala
            820                 825
```

<210> SEQ ID NO 55
<211> LENGTH: 828
<212> TYPE: PRT
<213> ORGANISM: Mus musculus

<400> SEQUENCE: 55

```
Met Gly Leu Pro Pro Arg Ile Ser Ser Leu Ala Ser Gly Asn Val Arg
1               5                   10                  15

Ser Leu Pro Ser Gln Gln Met Val Asn Arg Leu Ser Ile Pro Lys Pro
                20                  25                  30

Asn Leu Asn Ser Thr Gly Val Asn Met Met Ser Asn Val His Leu Gln
            35                  40                  45

Gln Asn Asn Tyr Gly Val Lys Ser Val Gly Gln Ser Tyr Gly Val Gly
        50                  55                  60

Gln Ser Val Arg Leu Gly Leu Gly Gly Asn Ala Pro Val Ser Ile Pro
65                  70                  75                  80

Gln Gln Ser Gln Ser Val Lys Gln Leu Leu Pro Ser Gly Asn Gly Arg
```

-continued

```
                    85                  90                  95
Ser Phe Gly Leu Gly Ala Glu Gln Arg Pro Ala Ala Arg Tyr
                100                 105                 110
Ser Leu Gln Thr Ala Asn Thr Ser Leu Pro Pro Gly Gln Val Lys Ser
            115                 120                 125
Pro Ser Val Ser Gln Ser Gln Ala Ser Arg Val Leu Gly Gln Ser Ser
130                 135                 140
Ser Lys Pro Pro Ala Ala Thr Gly Pro Pro Ser Asn His Cys
145                 150                 155                 160
Ala Thr Gln Lys Trp Lys Ile Cys Thr Ile Cys Asn Glu Leu Phe Pro
                165                 170                 175
Glu Asn Val Tyr Ser Val His Phe Glu Lys Glu His Lys Ala Glu Lys
            180                 185                 190
Val Pro Ala Val Ala Asn Tyr Ile Met Lys Ile His Asn Phe Thr Ser
            195                 200                 205
Lys Cys Leu Tyr Cys Asn Arg Tyr Leu Pro Thr Asp Thr Leu Leu Asn
    210                 215                 220
His Met Leu Ile His Gly Leu Ser Cys Pro Tyr Cys Arg Ser Thr Phe
225                 230                 235                 240
Asn Asp Val Glu Lys Met Ala Ala His Met Arg Met Val His Ile Asp
                245                 250                 255
Glu Glu Met Gly Pro Lys Thr Asp Ser Thr Leu Ser Phe Asp Leu Thr
            260                 265                 270
Leu Gln Gln Gly Ser His Thr Asn Ile His Leu Leu Val Thr Thr Tyr
            275                 280                 285
Asn Leu Arg Asp Ala Pro Ala Glu Ser Val Ala Tyr His Ala Gln Asn
    290                 295                 300
Asn Ala Pro Val Pro Pro Lys Pro Gln Pro Lys Val Gln Glu Lys Ala
305                 310                 315                 320
Asp Val Pro Val Lys Ser Ser Pro Gln Ala Ala Val Pro Tyr Lys Lys
                325                 330                 335
Asp Val Gly Lys Thr Leu Cys Pro Leu Cys Phe Ser Ile Leu Lys Gly
            340                 345                 350
Pro Ile Ser Asp Ala Leu Ala His His Leu Arg Glu Arg His Gln Val
        355                 360                 365
Ile Gln Thr Val His Pro Val Glu Lys Lys Leu Thr Tyr Lys Cys Ile
    370                 375                 380
His Cys Leu Gly Val Tyr Thr Ser Asn Met Thr Ala Ser Thr Ile Thr
385                 390                 395                 400
Leu His Leu Val His Cys Arg Gly Val Gly Lys Thr Gln Asn Gly Gln
                405                 410                 415
Asp Lys Thr Asn Ala Pro Ser Arg Leu Asn Gln Ser Pro Gly Leu Ala
            420                 425                 430
Pro Val Lys Arg Thr Tyr Glu Gln Met Glu Phe Pro Leu Leu Lys Lys
        435                 440                 445
Arg Lys Leu Glu Glu Asp Ala Asp Ser Pro Ser Cys Phe Glu Glu Lys
    450                 455                 460
Pro Glu Glu Pro Val Val Leu Ala Leu Asp Pro Lys Gly His Glu Asp
465                 470                 475                 480
Asp Ser Tyr Glu Ala Arg Lys Ser Phe Leu Thr Lys Tyr Phe Asn Lys
                485                 490                 495
Gln Pro Tyr Pro Thr Arg Arg Glu Ile Glu Lys Leu Ala Ala Ser Leu
            500                 505                 510
```

```
Trp Leu Trp Lys Ser Asp Ile Ala Ser His Phe Ser Asn Lys Arg Lys
        515                 520                 525

Lys Cys Val Arg Asp Cys Glu Lys Tyr Lys Pro Gly Val Leu Leu Gly
    530                 535                 540

Phe Asn Met Lys Glu Leu Asn Lys Val Lys His Glu Met Asp Phe Asp
545                 550                 555                 560

Ala Glu Trp Leu Phe Glu Asn His Asp Glu Lys Asp Ser Arg Val Asn
                565                 570                 575

Ala Ser Lys Thr Val Asp Lys Lys His Asn Leu Gly Lys Glu Asp Asp
            580                 585                 590

Ser Phe Ser Asp Ser Phe Glu His Leu Glu Glu Ser Asn Gly Ser
        595                 600                 605

Gly Ser Pro Phe Asp Pro Val Phe Glu Val Glu Pro Lys Ile Pro Ser
    610                 615                 620

Asp Asn Leu Glu Glu Pro Val Pro Lys Val Ile Pro Glu Gly Ala Leu
625                 630                 635                 640

Glu Ser Glu Lys Leu Asp Gln Lys Glu Glu Glu Glu Glu Glu
                645                 650                 655

Glu Asp Gly Ser Lys Tyr Glu Thr Ile His Leu Thr Glu Glu Pro Ala
            660                 665                 670

Lys Leu Met His Asp Ala Ser Asp Ser Glu Val Asp Gln Asp Val
        675                 680                 685

Val Glu Trp Lys Asp Gly Ala Ser Pro Ser Glu Ser Gly Pro Gly Ser
    690                 695                 700

Gln Gln Ile Ser Asp Phe Glu Asp Asn Thr Cys Glu Met Lys Pro Gly
705                 710                 715                 720

Thr Trp Ser Asp Glu Ser Ser Gln Ser Glu Asp Ala Arg Ser Ser Lys
                725                 730                 735

Pro Ala Ala Lys Lys Ala Thr Val Gln Asp Asp Thr Glu Gln Leu
            740                 745                 750

Lys Trp Lys Asn Ser Ser Tyr Gly Lys Val Glu Gly Phe Trp Ser Lys
        755                 760                 765

Asp Gln Ser Gln Trp Glu Asn Ala Ser Glu Asn Ala Glu Arg Leu Pro
    770                 775                 780

Asn Pro Gln Ile Glu Trp Gln Asn Ser Thr Ile Asp Ser Glu Asp Gly
785                 790                 795                 800

Glu His Phe Asp Ser Met Thr Asp Gly Val Ala Asp Pro Met His Gly
                805                 810                 815

Ser Leu Thr Gly Val Lys Leu Ser Ser Gln Gln Ala
            820                 825

<210> SEQ ID NO 56
<211> LENGTH: 2181
<212> TYPE: DNA
<213> ORGANISM: Homo sapiens
<220> FEATURE:
<221> NAME/KEY: CDS
<222> LOCATION: (1)..(2181)
<223> OTHER INFORMATION: H3 human activity dependent neurotrophic factor
      III (ADNF III) clone

<400> SEQUENCE: 56 cgg tct tta cca tca cag cag atg gtg aat cga ctc tca ata cca aag        48
Arg Ser Leu Pro Ser Gln Gln Met Val Asn Arg Leu Ser Ile Pro Lys
  1               5                  10                  15 cct aac tta aat tct aca gga gtc aac atg atg tcc agt gtt cat ctg        96
```

```
                Pro Asn Leu Asn Ser Thr Gly Val Asn Met Met Ser Ser Val His Leu
                                20                  25                  30 cag cag aac aac tat gga gtc aaa tct gta ggc cag ggt tac agt gtt        144
Gln Gln Asn Asn Tyr Gly Val Lys Ser Val Gly Gln Gly Tyr Ser Val
            35                  40                  45 ggt cag tca atg aga ctg ggt cta ggt ggc aac gca cca gtt tcc att        192
Gly Gln Ser Met Arg Leu Gly Leu Gly Gly Asn Ala Pro Val Ser Ile
    50                  55                  60 cct caa caa tct cag tct gta aag cag tta ctt cca agt gga aac gga        240
Pro Gln Gln Ser Gln Ser Val Lys Gln Leu Leu Pro Ser Gly Asn Gly
65                  70                  75                  80 agg tct tat ggg ctt ggg tca gag cag agg tcc cag gca cca gca aga        288
Arg Ser Tyr Gly Leu Gly Ser Glu Gln Arg Ser Gln Ala Pro Ala Arg
                85                  90                  95 tac tcc ctg cag tct gct aat gcc tct tct ctc tca tcg ggc cag tta        336
Tyr Ser Leu Gln Ser Ala Asn Ala Ser Ser Leu Ser Ser Gly Gln Leu
            100                 105                 110 aag tct cct tcc ctc tct cag tca cag gca tcc aga gtg tta ggt cag        384
Lys Ser Pro Ser Leu Ser Gln Ser Gln Ala Ser Arg Val Leu Gly Gln
        115                 120                 125 tcc agt tcc aaa cct gct gca gct gcc aca ggc cct ccc cca ggt aac        432
Ser Ser Ser Lys Pro Ala Ala Ala Ala Thr Gly Pro Pro Pro Gly Asn
    130                 135                 140 act tcc tca act caa aag tgg aaa ata tgt aca atc tgt aat gag ctt        480
Thr Ser Ser Thr Gln Lys Trp Lys Ile Cys Thr Ile Cys Asn Glu Leu
145                 150                 155                 160 ttt cct gaa aat gtc tat agt gtg cac ttc gaa aaa gaa cat aaa gct        528
Phe Pro Glu Asn Val Tyr Ser Val His Phe Glu Lys Glu His Lys Ala
                165                 170                 175 gag aaa gtc cca gca gta gcc aac tac att atg aaa ata cac aat ttt        576
Glu Lys Val Pro Ala Val Ala Asn Tyr Ile Met Lys Ile His Asn Phe
            180                 185                 190 act agc aaa tgc ctc tac tgt aat cgc tat tta ccc aca gat act ctg        624
Thr Ser Lys Cys Leu Tyr Cys Asn Arg Tyr Leu Pro Thr Asp Thr Leu
        195                 200                 205 ctc aac cat atg tta att cat ggt ctg tct tgt cca tat tgc cgt tca        672
Leu Asn His Met Leu Ile His Gly Leu Ser Cys Pro Tyr Cys Arg Ser
    210                 215                 220 act ttc aat gat gtg gaa aag atg gcc gca cac atg cgg atg gtt cac        720
Thr Phe Asn Asp Val Glu Lys Met Ala Ala His Met Arg Met Val His
225                 230                 235                 240 att gat gaa gag atg gga cct aaa aca gat tct act ttg agt ttt gat        768
Ile Asp Glu Glu Met Gly Pro Lys Thr Asp Ser Thr Leu Ser Phe Asp
                245                 250                 255 ttg aca ttg cag cag ggt agt cac act aac atc cat ctc ctg gta act        816
Leu Thr Leu Gln Gln Gly Ser His Thr Asn Ile His Leu Leu Val Thr
            260                 265                 270 aca tac aat ctg agg gat gcc cca gct gaa tct gtt gct tac cat gcc        864
Thr Tyr Asn Leu Arg Asp Ala Pro Ala Glu Ser Val Ala Tyr His Ala
        275                 280                 285 caa aat aat cct cca gtt cct cca aag cca cag cca aag gtt cag gaa        912
Gln Asn Asn Pro Pro Val Pro Pro Lys Pro Gln Pro Lys Val Gln Glu
    290                 295                 300 aag gca gat atc cct gta aaa agt tca cct caa gct gca gtg ccc tat        960
Lys Ala Asp Ile Pro Val Lys Ser Ser Pro Gln Ala Ala Val Pro Tyr
305                 310                 315                 320 aaa aaa gat gtt ggg aaa acc ctt tgt cct ctt tgc ttt tca atc cta       1008
Lys Lys Asp Val Gly Lys Thr Leu Cys Pro Leu Cys Phe Ser Ile Leu
                325                 330                 335
```

-continued

```
aaa gga ccc ata tct gat gca ctt gca cat cac tta cga gag agg cac    1056
Lys Gly Pro Ile Ser Asp Ala Leu Ala His His Leu Arg Glu Arg His
        340                 345                 350 caa gtt att cag acg gtt cat cca gtt gag aaa aag ctc acc tac aaa    1104
Gln Val Ile Gln Thr Val His Pro Val Glu Lys Lys Leu Thr Tyr Lys
    355                 360                 365 tgt atc cat tgc ctt ggt gtg tat acc agc aac atg acc gcc tca act    1152
Cys Ile His Cys Leu Gly Val Tyr Thr Ser Asn Met Thr Ala Ser Thr
370                 375                 380 atc act ctg cat cta gtt cac tgc agg ggc gtt gga aag acc caa aat    1200
Ile Thr Leu His Leu Val His Cys Arg Gly Val Gly Lys Thr Gln Asn
385                 390                 395                 400 ggc cag gat aag aca aat gca ccc tct cgg ctt aat cag tct cca agt    1248
Gly Gln Asp Lys Thr Asn Ala Pro Ser Arg Leu Asn Gln Ser Pro Ser
        405                 410                 415 ctg gca cct gtg aag cgc act tac gag caa atg gaa ttt ccc tta ctg    1296
Leu Ala Pro Val Lys Arg Thr Tyr Glu Gln Met Glu Phe Pro Leu Leu
    420                 425                 430 aaa aaa cga aag tta gat gat gat agt gat tca ccc agc ttc ttt gaa    1344
Lys Lys Arg Lys Leu Asp Asp Asp Ser Asp Ser Pro Ser Phe Phe Glu
        435                 440                 445 gag aag cct gaa gag cct gtt gtt tta gct tta gac ccc aag ggt cat    1392
Glu Lys Pro Glu Glu Pro Val Val Leu Ala Leu Asp Pro Lys Gly His
450                 455                 460 gaa gat gat tcc tat gaa gcc agg aaa agc ttt cta aca aag tat ttc    1440
Glu Asp Asp Ser Tyr Glu Ala Arg Lys Ser Phe Leu Thr Lys Tyr Phe
465                 470                 475                 480 aac aaa cag ccc tat ccc acc agg aga gaa att gag aag cta gca gcc    1488
Asn Lys Gln Pro Tyr Pro Thr Arg Arg Glu Ile Glu Lys Leu Ala Ala
        485                 490                 495 agt tta tgg tta tgg aag agt gac atc gct tcc cat ttt agt aac aaa    1536
Ser Leu Trp Leu Trp Lys Ser Asp Ile Ala Ser His Phe Ser Asn Lys
    500                 505                 510 agg aag aag tgt gtc cgt gat tgt gaa aag tac aag cct ggc gtg ttg    1584
Arg Lys Lys Cys Val Arg Asp Cys Glu Lys Tyr Lys Pro Gly Val Leu
        515                 520                 525 ctg ggg ttt aac atg aaa gaa tta aat aaa gtc aag cat gag atg gat    1632
Leu Gly Phe Asn Met Lys Glu Leu Asn Lys Val Lys His Glu Met Asp
530                 535                 540 ttt gat gct gag tgg cta ttt gaa aat cat gat gag aag gat tcc aga    1680
Phe Asp Ala Glu Trp Leu Phe Glu Asn His Asp Glu Lys Asp Ser Arg
545                 550                 555                 560 gtc aat gct agt aag act gct gac aaa aag ctc aac ctt ggg aag gaa    1728
Val Asn Ala Ser Lys Thr Ala Asp Lys Lys Leu Asn Leu Gly Lys Glu
        565                 570                 575 gat gac agt tcc tca gac agt ttt gaa aat ttg gaa gaa gaa tcc aat    1776
Asp Asp Ser Ser Ser Asp Ser Phe Glu Asn Leu Glu Glu Glu Ser Asn
    580                 585                 590 gaa agt ggt agc cct ttt gac cct gtt ttt gaa gtt gaa cct aaa atc    1824
Glu Ser Gly Ser Pro Phe Asp Pro Val Phe Glu Val Glu Pro Lys Ile
        595                 600                 605 tct aac gat aac cca gag gaa cat gta ctg aag gta att cct gag gat    1872
Ser Asn Asp Asn Pro Glu Glu His Val Leu Lys Val Ile Pro Glu Asp
610                 615                 620 gct tca gaa tct gag gag aag cta gac caa aaa gag gat ggt tca aaa    1920
Ala Ser Glu Ser Glu Glu Lys Leu Asp Gln Lys Glu Asp Gly Ser Lys
625                 630                 635                 640 tac gaa act att cat ttg act gag gaa cca acc aaa cta atg cac aat    1968
Tyr Glu Thr Ile His Leu Thr Glu Glu Pro Thr Lys Leu Met His Asn
        645                 650                 655
```

```
gca tct gat agt gag gtt gac caa gac gat gtt gtt gag tgg aaa gac         2016
Ala Ser Asp Ser Glu Val Asp Gln Asp Asp Val Val Glu Trp Lys Asp
            660                 665                 670 ggt gct tct cca tct gag agt ggg cct gga tcc caa caa gtg tca gac         2064
Gly Ala Ser Pro Ser Glu Ser Gly Pro Gly Ser Gln Gln Val Ser Asp
    675                 680                 685 ttt gag gac aat acc tgc gaa atg aaa cca gga acc tgg tct gac gag         2112
Phe Glu Asp Asn Thr Cys Glu Met Lys Pro Gly Thr Trp Ser Asp Glu
690                 695                 700 tct tcc caa agc gaa gat gca agg agc agt aag cca gct gcc aaa aaa         2160
Ser Ser Gln Ser Glu Asp Ala Arg Ser Ser Lys Pro Ala Ala Lys Lys
705                 710                 715                 720 aaa ggc tac cat gca agg tga                                             2181
Lys Gly Tyr His Ala Arg
            725
```

<210> SEQ ID NO 57
<211> LENGTH: 726
<212> TYPE: PRT
<213> ORGANISM: Homo sapiens

<400> SEQUENCE: 57

```
Arg Ser Leu Pro Ser Gln Gln Met Val Asn Arg Leu Ser Ile Pro Lys
 1               5                  10                  15

Pro Asn Leu Asn Ser Thr Gly Val Asn Met Met Ser Ser Val His Leu
                20                  25                  30

Gln Gln Asn Asn Tyr Gly Val Lys Ser Val Gly Gln Gly Tyr Ser Val
            35                  40                  45

Gly Gln Ser Met Arg Leu Gly Leu Gly Gly Asn Ala Pro Val Ser Ile
        50                  55                  60

Pro Gln Gln Ser Gln Ser Val Lys Gln Leu Leu Pro Ser Gly Asn Gly
    65                  70                  75                  80

Arg Ser Tyr Gly Leu Gly Ser Glu Gln Arg Ser Gln Ala Pro Ala Arg
                85                  90                  95

Tyr Ser Leu Gln Ser Ala Asn Ala Ser Leu Ser Ser Gly Gln Leu
                100                 105                 110

Lys Ser Pro Ser Leu Ser Gln Ser Gln Ala Ser Arg Val Leu Gly Gln
            115                 120                 125

Ser Ser Lys Pro Ala Ala Ala Thr Gly Pro Pro Gly Asn
130                 135                 140

Thr Ser Thr Gln Lys Trp Lys Ile Cys Thr Ile Cys Asn Glu Leu
145                 150                 155                 160

Phe Pro Glu Asn Val Tyr Ser Val His Phe Glu Lys Glu His Lys Ala
                165                 170                 175

Glu Lys Val Pro Ala Val Ala Asn Tyr Ile Met Lys Ile His Asn Phe
            180                 185                 190

Thr Ser Lys Cys Leu Tyr Cys Asn Arg Tyr Leu Pro Thr Asp Thr Leu
        195                 200                 205

Leu Asn His Met Leu Ile His Gly Leu Ser Cys Pro Tyr Cys Arg Ser
    210                 215                 220

Thr Phe Asn Asp Val Glu Lys Met Ala Ala His Met Arg Met Val His
225                 230                 235                 240

Ile Asp Glu Glu Met Gly Pro Lys Thr Asp Ser Thr Leu Ser Phe Asp
                245                 250                 255

Leu Thr Leu Gln Gln Gly Ser His Thr Asn Ile His Leu Leu Val Thr
            260                 265                 270
```

-continued

```
Thr Tyr Asn Leu Arg Asp Ala Pro Ala Glu Ser Val Ala Tyr His Ala
            275                 280                 285
Gln Asn Asn Pro Pro Val Pro Pro Lys Pro Gln Pro Lys Val Gln Glu
        290                 295                 300
Lys Ala Asp Ile Pro Val Lys Ser Ser Pro Gln Ala Ala Val Pro Tyr
305                 310                 315                 320
Lys Lys Asp Val Gly Lys Thr Leu Cys Pro Leu Cys Phe Ser Ile Leu
                325                 330                 335
Lys Gly Pro Ile Ser Asp Ala Leu Ala His His Leu Arg Glu Arg His
            340                 345                 350
Gln Val Ile Gln Thr Val His Pro Val Glu Lys Lys Leu Thr Tyr Lys
        355                 360                 365
Cys Ile His Cys Leu Gly Val Tyr Thr Ser Asn Met Thr Ala Ser Thr
370                 375                 380
Ile Thr Leu His Leu Val His Cys Arg Gly Val Gly Lys Thr Gln Asn
385                 390                 395                 400
Gly Gln Asp Lys Thr Asn Ala Pro Ser Arg Leu Asn Gln Ser Pro Ser
                405                 410                 415
Leu Ala Pro Val Lys Arg Thr Tyr Glu Gln Met Glu Phe Pro Leu Leu
            420                 425                 430
Lys Lys Arg Lys Leu Asp Asp Ser Asp Ser Pro Ser Phe Phe Glu
        435                 440                 445
Glu Lys Pro Glu Glu Pro Val Val Leu Ala Leu Asp Pro Lys Gly His
    450                 455                 460
Glu Asp Asp Ser Tyr Glu Ala Arg Lys Ser Phe Leu Thr Lys Tyr Phe
465                 470                 475                 480
Asn Lys Gln Pro Tyr Pro Thr Arg Arg Glu Ile Glu Lys Leu Ala Ala
                485                 490                 495
Ser Leu Trp Leu Trp Lys Ser Asp Ile Ala Ser His Phe Ser Asn Lys
            500                 505                 510
Arg Lys Lys Cys Val Arg Asp Cys Glu Lys Tyr Lys Pro Gly Val Leu
        515                 520                 525
Leu Gly Phe Asn Met Lys Glu Leu Asn Lys Val Lys His Glu Met Asp
    530                 535                 540
Phe Asp Ala Glu Trp Leu Phe Glu Asn His Asp Glu Lys Asp Ser Arg
545                 550                 555                 560
Val Asn Ala Ser Lys Thr Ala Asp Lys Lys Leu Asn Leu Gly Lys Glu
                565                 570                 575
Asp Asp Ser Ser Ser Asp Ser Phe Glu Asn Leu Glu Glu Ser Asn
            580                 585                 590
Glu Ser Gly Ser Pro Phe Asp Pro Val Phe Glu Val Glu Pro Lys Ile
        595                 600                 605
Ser Asn Asp Asn Pro Glu Glu His Val Leu Lys Val Ile Pro Glu Asp
    610                 615                 620
Ala Ser Glu Ser Glu Glu Lys Leu Asp Gln Lys Glu Asp Gly Ser Lys
625                 630                 635                 640
Tyr Glu Thr Ile His Leu Thr Glu Glu Pro Thr Lys Leu Met His Asn
                645                 650                 655
Ala Ser Asp Ser Glu Val Asp Gln Asp Val Val Glu Trp Lys Asp
            660                 665                 670
Gly Ala Ser Pro Ser Glu Ser Gly Pro Gly Ser Gln Gln Val Ser Asp
        675                 680                 685
```

```
Phe Glu Asp Asn Thr Cys Glu Met Lys Pro Gly Thr Trp Ser Asp Glu
        690                 695                 700
Ser Ser Gln Ser Glu Asp Ala Arg Ser Ser Lys Pro Ala Ala Lys Lys
705                 710                 715                 720
Lys Gly Tyr His Ala Arg
                725

<210> SEQ ID NO 58
<211> LENGTH: 4193
<212> TYPE: DNA
<213> ORGANISM: Homo sapiens
<220> FEATURE:
<221> NAME/KEY: CDS
<222> LOCATION: (492)..(3116)
<223> OTHER INFORMATION: H7 human activity dependent neurotrophic factor
      III (ADNF III) clone

<400> SEQUENCE: 58
aaaaccagga ctatcggaca aaacctttct gctgcagcgc ttgtccattt tcctcaaaat    60
tcttctctgc ctacaaaagt catttccgca atgtccatag tgaagacttt gaaaatagga   120
ttctccttaa ttgcccctac tgtaccttca atgcagacaa aaagactttg aaacacaca   180 ttaaaatatt tcatgctccg aacgccagcg caccaagtag cagcttcagc actttcaaag   240
ataaaaccaa aaatgatggc cttaaactta agcaggctga cagtgtagag caagctgttt   300
attactgtaa gaagtgcact taccgagatc ctctttatga aatagttagg aagcacattt   360
acagggaaca ttttcagcat gtggcagcac cttacatagc aaaggcagga gaaaaatcac   420
tcaatggggc agtccccta ggctcgaatg cccgagaaga gagtagtatt cactgcaagc   480
gatgcctttt c atg cca aag tcc tat gaa gct ttg gta cag cat gtc atc   530
            Met Pro Lys Ser Tyr Glu Ala Leu Val Gln His Val Ile
              1               5                  10
``` gaa gac cat gaa cgt ata ggc tat cag gtc act gcc atg att ggg cac    578
Glu Asp His Glu Arg Ile Gly Tyr Gln Val Thr Ala Met Ile Gly His
     15                  20                  25 aca aat gta gtg gtt ccc cga tcc aaa ccc ttg atg cta att gct ccc    626
Thr Asn Val Val Val Pro Arg Ser Lys Pro Leu Met Leu Ile Ala Pro
 30                  35                  40                  45 aaa cct caa gac aag aag agc atg gga ctc cca cca agg atc ggt tcc    674
Lys Pro Gln Asp Lys Lys Ser Met Gly Leu Pro Pro Arg Ile Gly Ser
                 50                  55                  60 ctt gct tct gga aat gtc cgg tct tta cca tca cag cag atg gtg aat    722
Leu Ala Ser Gly Asn Val Arg Ser Leu Pro Ser Gln Gln Met Val Asn
             65                  70                  75 cga ctc tca ata cca aag cct aac tta aat tct aca gga gtc aac atg    770
Arg Leu Ser Ile Pro Lys Pro Asn Leu Asn Ser Thr Gly Val Asn Met
         80                  85                  90 atg tcc agt gtt cat ctg cag cag aac aac tat gga gtc aaa tct gta    818
Met Ser Ser Val His Leu Gln Gln Asn Asn Tyr Gly Val Lys Ser Val
     95                  100                 105 ggc cag ggt tac agt gtt ggt cag tca atg aga ctg ggt cta ggt ggc    866
Gly Gln Gly Tyr Ser Val Gly Gln Ser Met Arg Leu Gly Leu Gly Gly
110                 115                 120                 125 aac gca cca gtt tcc att cct caa caa tct cag tct gta aag cag tta    914
Asn Ala Pro Val Ser Ile Pro Gln Gln Ser Gln Ser Val Lys Gln Leu
                 130                 135                 140 ctt cca agt gga aac gga agg tct tat ggg ctt ggg tca gag cag agg    962
Leu Pro Ser Gly Asn Gly Arg Ser Tyr Gly Leu Gly Ser Glu Gln Arg
             145                 150                 155 tcc cag gca cca gca aga tac tcc ctg cag tct gct aat gcc tct tct   1010

```
Ser Gln Ala Pro Ala Arg Tyr Ser Leu Gln Ser Ala Asn Ala Ser Ser
            160                 165                 170 ctc tca tcg ggc cag tta aag tct cct tcc ctc tct cag tca cag gca    1058
Leu Ser Ser Gly Gln Leu Lys Ser Pro Ser Leu Ser Gln Ser Gln Ala
    175                 180                 185 tcc aga gtg tta ggt cag tcc agt tcc aaa cct gct gca gct gcc aca    1106
Ser Arg Val Leu Gly Gln Ser Ser Ser Lys Pro Ala Ala Ala Ala Thr
190                 195                 200                 205 ggc cct ccc cca ggt aac act tcc tca act caa aag tgg aaa ata tgt    1154
Gly Pro Pro Pro Gly Asn Thr Ser Ser Thr Gln Lys Trp Lys Ile Cys
                210                 215                 220 aca atc tgt aat gag ctt ttt cct gaa aat gtc tat agt gtg cac ttc    1202
Thr Ile Cys Asn Glu Leu Phe Pro Glu Asn Val Tyr Ser Val His Phe
            225                 230                 235 gaa aaa gaa cat aaa gct gag aaa gtc cca gca gta gcc aac tac att    1250
Glu Lys Glu His Lys Ala Glu Lys Val Pro Ala Val Ala Asn Tyr Ile
        240                 245                 250 atg aaa ata cac aat ttt act agc aaa tgc ctc tac tgt aat cgc tat    1298
Met Lys Ile His Asn Phe Thr Ser Lys Cys Leu Tyr Cys Asn Arg Tyr
    255                 260                 265 tta ccc aca gat act ctg ctc aac cat atg tta att cat ggt ctg tct    1346
Leu Pro Thr Asp Thr Leu Leu Asn His Met Leu Ile His Gly Leu Ser
270                 275                 280                 285 tgt cca tat tgc cgt tca act ttc aat gat gtg gaa aag atg gcc gca    1394
Cys Pro Tyr Cys Arg Ser Thr Phe Asn Asp Val Glu Lys Met Ala Ala
                290                 295                 300 cac atg cgg atg gtt cac att gat gaa gag atg gga cct aaa aca gat    1442
His Met Arg Met Val His Ile Asp Glu Glu Met Gly Pro Lys Thr Asp
            305                 310                 315 tct act ttg agt ttt gat ttg aca ttg cag cag ggt agt cac act aac    1490
Ser Thr Leu Ser Phe Asp Leu Thr Leu Gln Gln Gly Ser His Thr Asn
        320                 325                 330 atc cat ctc ctg gta act aca tac aat ctg agg gat gcc cca gct gaa    1538
Ile His Leu Leu Val Thr Thr Tyr Asn Leu Arg Asp Ala Pro Ala Glu
    335                 340                 345 tct gtt gct tac cat gcc caa aat aat cct cca gtt cct cca aag cca    1586
Ser Val Ala Tyr His Ala Gln Asn Asn Pro Pro Val Pro Pro Lys Pro
350                 355                 360                 365 cag cca aag gtt cag gaa aag gca gat atc cct gta aaa agt tca cct    1634
Gln Pro Lys Val Gln Glu Lys Ala Asp Ile Pro Val Lys Ser Ser Pro
                370                 375                 380 caa gct gca gtg ccc tat aaa aaa gat gtt ggg aaa acc ctt tgt cct    1682
Gln Ala Ala Val Pro Tyr Lys Lys Asp Val Gly Lys Thr Leu Cys Pro
            385                 390                 395 ctt tgc ttt tca atc cta aaa gga ccc ata tct gat gca ctt gca cat    1730
Leu Cys Phe Ser Ile Leu Lys Gly Pro Ile Ser Asp Ala Leu Ala His
        400                 405                 410 cac tta cga gag agg cac caa gtt att cag acg gtt cat cca gtt gag    1778
His Leu Arg Glu Arg His Gln Val Ile Gln Thr Val His Pro Val Glu
    415                 420                 425 aaa aag ctc acc tac aaa tgt atc cat tgc ctt ggt gtg tat acc agc    1826
Lys Lys Leu Thr Tyr Lys Cys Ile His Cys Leu Gly Val Tyr Thr Ser
430                 435                 440                 445 aac atg acc gcc tca act atc act ctg cat cta gtt cac tgc agg ggc    1874
Asn Met Thr Ala Ser Thr Ile Thr Leu His Leu Val His Cys Arg Gly
                450                 455                 460 gtt gga aag acc caa aat ggc cag gat aag aca aat gca ccc tct cgg    1922
Val Gly Lys Thr Gln Asn Gly Gln Asp Lys Thr Asn Ala Pro Ser Arg
            465                 470                 475
```

-continued

| | | |
|---|---|---|
| ctt aat cag tct cca agt ctg gca cct gtg aag cgc act tac gag caa<br>Leu Asn Gln Ser Pro Ser Leu Ala Pro Val Lys Arg Thr Tyr Glu Gln<br>480                        485                       490 | 1970 |
| atg gaa ttt ccc tta ctg aaa aaa cga aag tta gat gat gat agt gat<br>Met Glu Phe Pro Leu Leu Lys Lys Arg Lys Leu Asp Asp Asp Ser Asp<br>495                        500                       505 | 2018 |
| tca ccc agc ttc ttt gaa gag aag cct gaa gag cct gtt gtt tta gct<br>Ser Pro Ser Phe Phe Glu Glu Lys Pro Glu Glu Pro Val Val Leu Ala<br>510                        515                       520                       525 | 2066 |
| tta gac ccc aag ggt cat gaa gat gat tcc tat gaa gcc agg aaa agc<br>Leu Asp Pro Lys Gly His Glu Asp Asp Ser Tyr Glu Ala Arg Lys Ser<br>                       530                       535                       540 | 2114 |
| ttt cta aca aag tat ttc aac aaa cag ccc tat ccc acc agg aga gaa<br>Phe Leu Thr Lys Tyr Phe Asn Lys Gln Pro Tyr Pro Thr Arg Arg Glu<br>                       545                       550                       555 | 2162 |
| att gag aag cta gca gcc agt tta tgg tta tgg aag agt gac atc gct<br>Ile Glu Lys Leu Ala Ala Ser Leu Trp Leu Trp Lys Ser Asp Ile Ala<br>560                        565                       570 | 2210 |
| tcc cat ttt agt aac aaa agg aag aag tgt gtc cgt gat tgt gaa aag<br>Ser His Phe Ser Asn Lys Arg Lys Lys Cys Val Arg Asp Cys Glu Lys<br>575                        580                       585 | 2258 |
| tac aag cct ggc gtg ttg ctg ggg ttt aac atg aaa gaa tta aat aaa<br>Tyr Lys Pro Gly Val Leu Leu Gly Phe Asn Met Lys Glu Leu Asn Lys<br>590                        595                       600                       605 | 2306 |
| gtc aag cat gag atg gat ttt gat gct gag tgg cta ttt gaa aat cat<br>Val Lys His Glu Met Asp Phe Asp Ala Glu Trp Leu Phe Glu Asn His<br>                       610                       615                       620 | 2354 |
| gat gag aag gat tcc aga gtc aat gct agt aag act gct gac aaa aag<br>Asp Glu Lys Asp Ser Arg Val Asn Ala Ser Lys Thr Ala Asp Lys Lys<br>625                        630                       635 | 2402 |
| ctc aac ctt ggg aag gaa gat gac agt tcc tca gac agt ttt gaa aat<br>Leu Asn Leu Gly Lys Glu Asp Asp Ser Ser Ser Asp Ser Phe Glu Asn<br>640                        645                       650 | 2450 |
| ttg gaa gaa gaa tcc aat gaa agt ggt agc cct ttt gac cct gtt ttt<br>Leu Glu Glu Glu Ser Asn Glu Ser Gly Ser Pro Phe Asp Pro Val Phe<br>655                        660                       665 | 2498 |
| gaa gtt gaa cct aaa atc tct aac gat aac cca gaa gaa cat gta ctg<br>Glu Val Glu Pro Lys Ile Ser Asn Asp Asn Pro Glu Glu His Val Leu<br>670                        675                       680                       685 | 2546 |
| aag gta att cct gag gat gct tca gaa tct gag gag aag cta gac caa<br>Lys Val Ile Pro Glu Asp Ala Ser Glu Ser Glu Glu Lys Leu Asp Gln<br>                       690                       695                       700 | 2594 |
| aaa gaa gat ggt tca aaa tac gaa act att cat ttg act gag gaa cca<br>Lys Glu Asp Gly Ser Lys Tyr Glu Thr Ile His Leu Thr Glu Glu Pro<br>                       705                       710                       715 | 2642 |
| acc aaa cta atg cac aat gca tct gat agt gag gtt gac caa gac gat<br>Thr Lys Leu Met His Asn Ala Ser Asp Ser Glu Val Asp Gln Asp Asp<br>720                        725                       730 | 2690 |
| gtt gtt gag tgg aaa gac ggt gct tct cca tct gag agt ggg cct gga<br>Val Val Glu Trp Lys Asp Gly Ala Ser Pro Ser Glu Ser Gly Pro Gly<br>735                        740                       745 | 2738 |
| tcc caa caa gtg tca gac ttt gag gac aat acc tgc gaa atg aaa cca<br>Ser Gln Gln Val Ser Asp Phe Glu Asp Asn Thr Cys Glu Met Lys Pro<br>750                        755                       760                       765 | 2786 |
| gga acc tgg tct gac gag tct tcc caa agc gaa gat gca agg agc agt<br>Gly Thr Trp Ser Asp Glu Ser Ser Gln Ser Glu Asp Ala Arg Ser Ser<br>                       770                       775                       780 | 2834 |
| aag cca gct gcc aaa aaa aag gct acc atg caa ggt gac aga gag cag<br>Lys Pro Ala Ala Lys Lys Lys Ala Thr Met Gln Gly Asp Arg Glu Gln<br>785                        790                       795 | 2882 |

-continued

```
ttg aaa tgg aag aat agt tcc tat gga aaa gtt gaa ggg ttt tgg tct    2930
Leu Lys Trp Lys Asn Ser Ser Tyr Gly Lys Val Glu Gly Phe Trp Ser
        800                 805                 810 aag gac cag tca cag tgg aag aat gca tct gag aat gat gag cgc tta    2978
Lys Asp Gln Ser Gln Trp Lys Asn Ala Ser Glu Asn Asp Glu Arg Leu
815                 820                 825 tct aac ccc cag att gag tgg cag aat agc aca att gac agt gag gat    3026
Ser Asn Pro Gln Ile Glu Trp Gln Asn Ser Thr Ile Asp Ser Glu Asp
830                 835                 840                 845 ggg gaa cag ttt gac aac atg act gat gga gta gct gag ccc atg cat    3074
Gly Glu Gln Phe Asp Asn Met Thr Asp Gly Val Ala Glu Pro Met His
                850                 855                 860 ggc agc tta gcc gga gtt aaa ctg agc agc caa cag gcc taagtgccag     3123
Gly Ser Leu Ala Gly Val Lys Leu Ser Ser Gln Gln Ala
                865                 870 gttccctggc attggtgaca tgctgcagcc tggaactctg atctccagtg tgactgcaaa  3183
gctgtcttct cactggtact gccttgtgag tactggttgg actgtggggc atgtggccgc  3243
tgcagttcca gtggttattt ctaagtctat gacaggacag gctgttcttg cttcagaacc  3303
ttctctgaca gacacggtaa ctaaatgtga aaaccaata agctggtgac tcatgaatac   3363
acacgaggaa aagcagaggt ttattttatc tgccttttca acatttcttt ccctctgtga  3423
aatgattggt cagatgtctt tgagaagtgt taaactaatt cacatggtag tgtagggcca  3483
acatacaagc taccagtcta atgtgtatag tagactttgg gaaaagcgat ttttttttcat 3543
gtattcattc tgaatagttg aaatgtatat ttgtacagtc ttttagacct attcaagtga  3603
tgctcatgat cctgttactg tgtgcccatc atagatttct ttttttagtg ttgcccttgc  3663
tgtgtaataa acgctctatc tagtttacct agcaaaagct caaaactgcg ctagtatgga  3723
ctttttggac agacttagtt tttgcacata accttgtaca atcttgcaac agaggccagc  3783
cacgtaagat atatatctgg actctcttgg attataggat ttttcttggt ctgaatatcc  3843
ttgacattac agctgtcaaa acaaaaaact ggtatttcag atctgttttc tgaaatcttt  3903
taagctaaaa tcacatgcaa gaattgactt tgcagctact aattttgaca ccttttagat  3963
ctgtataaaa gtgtgttgtg ttgaagcagc aaaccaatga gtgctgcatt ttggatattt  4023
agttttatct ttagttcaac accatcatgg tggattcatt tataccatct aatatatgac  4083
acactgttgt agtatgtata attttgtgat ctttattttc cctttgtatt catttaagc   4143
atctaaataa attgctgtat tgtgcttaat gtaaaaaaaa aaaaaaaaa              4193
```

<210> SEQ ID NO 59
<211> LENGTH: 874
<212> TYPE: PRT
<213> ORGANISM: Homo sapiens

<400> SEQUENCE: 59

```
Met Pro Lys Ser Tyr Glu Ala Leu Val Gln His Val Ile Glu Asp His
 1               5                  10                  15

Glu Arg Ile Gly Tyr Gln Val Thr Ala Met Ile Gly His Thr Asn Val
            20                  25                  30

Val Val Pro Arg Ser Lys Pro Leu Met Leu Ile Ala Pro Lys Pro Gln
        35                  40                  45

Asp Lys Lys Ser Met Gly Leu Pro Pro Arg Ile Gly Ser Leu Ala Ser
    50                  55                  60

Gly Asn Val Arg Ser Leu Pro Ser Gln Gln Met Val Asn Arg Leu Ser
65                  70                  75                  80
```

```
Ile Pro Lys Pro Asn Leu Asn Ser Thr Gly Val Asn Met Met Ser Ser
                85                  90                  95

Val His Leu Gln Gln Asn Asn Tyr Gly Val Lys Ser Val Gly Gln Gly
            100                 105                 110

Tyr Ser Val Gly Gln Ser Met Arg Leu Gly Leu Gly Gly Asn Ala Pro
            115                 120                 125

Val Ser Ile Pro Gln Gln Ser Gln Ser Val Lys Gln Leu Leu Pro Ser
            130                 135                 140

Gly Asn Gly Arg Ser Tyr Gly Leu Gly Ser Glu Gln Arg Ser Gln Ala
145                 150                 155                 160

Pro Ala Arg Tyr Ser Leu Gln Ser Ala Asn Ala Ser Ser Leu Ser Ser
                165                 170                 175

Gly Gln Leu Lys Ser Pro Ser Leu Ser Gln Ser Gln Ala Ser Arg Val
            180                 185                 190

Leu Gly Gln Ser Ser Lys Pro Ala Ala Ala Thr Gly Pro Pro
            195                 200                 205

Pro Gly Asn Thr Ser Ser Thr Gln Lys Trp Lys Ile Cys Thr Ile Cys
        210                 215                 220

Asn Glu Leu Phe Pro Glu Asn Val Tyr Ser Val His Phe Glu Lys Glu
225                 230                 235                 240

His Lys Ala Glu Lys Val Pro Ala Val Ala Asn Tyr Ile Met Lys Ile
                245                 250                 255

His Asn Phe Thr Ser Lys Cys Leu Tyr Cys Asn Arg Tyr Leu Pro Thr
            260                 265                 270

Asp Thr Leu Leu Asn His Met Leu Ile His Gly Leu Ser Cys Pro Tyr
        275                 280                 285

Cys Arg Ser Thr Phe Asn Asp Val Glu Lys Met Ala Ala His Met Arg
        290                 295                 300

Met Val His Ile Asp Glu Met Gly Pro Lys Thr Asp Ser Thr Leu
305                 310                 315                 320

Ser Phe Asp Leu Thr Leu Gln Gln Gly Ser His Thr Asn Ile His Leu
            325                 330                 335

Leu Val Thr Thr Tyr Asn Leu Arg Asp Ala Pro Ala Glu Ser Val Ala
            340                 345                 350

Tyr His Ala Gln Asn Asn Pro Pro Val Pro Lys Pro Gln Pro Lys
        355                 360                 365

Val Gln Glu Lys Ala Asp Ile Pro Val Lys Ser Pro Gln Ala Ala
        370                 375                 380

Val Pro Tyr Lys Lys Asp Val Gly Lys Thr Leu Cys Pro Leu Cys Phe
385                 390                 395                 400

Ser Ile Leu Lys Gly Pro Ile Ser Asp Ala Leu Ala His His Leu Arg
            405                 410                 415

Glu Arg His Gln Val Ile Gln Thr Val His Pro Val Glu Lys Lys Leu
        420                 425                 430

Thr Tyr Lys Cys Ile His Cys Leu Gly Val Tyr Thr Ser Asn Met Thr
        435                 440                 445

Ala Ser Thr Ile Thr Leu His Leu Val His Cys Arg Gly Val Gly Lys
450                 455                 460

Thr Gln Asn Gly Gln Asp Lys Thr Asn Ala Pro Ser Arg Leu Asn Gln
465                 470                 475                 480

Ser Pro Ser Leu Ala Pro Val Lys Arg Thr Tyr Glu Gln Met Glu Phe
            485                 490                 495
```

Pro Leu Leu Lys Lys Arg Lys Leu Asp Asp Ser Asp Ser Pro Ser
            500                 505                 510

Phe Phe Glu Glu Lys Pro Glu Pro Val Val Leu Ala Leu Asp Pro
            515                 520                 525

Lys Gly His Glu Asp Asp Ser Tyr Glu Ala Arg Lys Ser Phe Leu Thr
            530                 535                 540

Lys Tyr Phe Asn Lys Gln Pro Tyr Pro Thr Arg Arg Glu Ile Glu Lys
545                 550                 555                 560

Leu Ala Ala Ser Leu Trp Leu Trp Lys Ser Asp Ile Ala Ser His Phe
                565                 570                 575

Ser Asn Lys Arg Lys Cys Val Arg Asp Cys Glu Lys Tyr Lys Pro
            580                 585                 590

Gly Val Leu Gly Phe Asn Met Lys Glu Leu Asn Lys Val Lys His
            595                 600                 605

Glu Met Asp Phe Asp Ala Glu Trp Leu Phe Glu Asn His Asp Glu Lys
            610                 615                 620

Asp Ser Arg Val Asn Ala Ser Lys Thr Ala Asp Lys Lys Leu Asn Leu
625                 630                 635                 640

Gly Lys Glu Asp Asp Ser Ser Asp Ser Phe Glu Asn Leu Glu Glu
                645                 650                 655

Glu Ser Asn Glu Ser Gly Ser Pro Phe Asp Pro Val Phe Glu Val Glu
            660                 665                 670

Pro Lys Ile Ser Asn Asp Asn Pro Glu Glu His Val Leu Lys Val Ile
            675                 680                 685

Pro Glu Asp Ala Ser Glu Ser Glu Lys Leu Asp Gln Lys Glu Asp
            690                 695                 700

Gly Ser Lys Tyr Glu Thr Ile His Leu Thr Glu Pro Thr Lys Leu
705                 710                 715                 720

Met His Asn Ala Ser Asp Ser Glu Val Asp Gln Asp Val Val Glu
                725                 730                 735

Trp Lys Asp Gly Ala Ser Pro Ser Glu Ser Gly Pro Gly Ser Gln Gln
            740                 745                 750

Val Ser Asp Phe Glu Asp Asn Thr Cys Glu Met Lys Pro Gly Thr Trp
            755                 760                 765

Ser Asp Glu Ser Ser Gln Ser Glu Asp Ala Arg Ser Ser Lys Pro Ala
            770                 775                 780

Ala Lys Lys Lys Ala Thr Met Gln Gly Asp Arg Glu Gln Leu Lys Trp
785                 790                 795                 800

Lys Asn Ser Ser Tyr Gly Lys Val Glu Gly Phe Trp Ser Lys Asp Gln
                805                 810                 815

Ser Gln Trp Lys Asn Ala Ser Glu Asn Asp Glu Arg Leu Ser Asn Pro
            820                 825                 830

Gln Ile Glu Trp Gln Asn Ser Thr Ile Asp Ser Glu Asp Gly Glu Gln
            835                 840                 845

Phe Asp Asn Met Thr Asp Gly Val Ala Glu Pro Met His Gly Ser Leu
            850                 855                 860

Ala Gly Val Lys Leu Ser Ser Gln Gln Ala
865                 870

<210> SEQ ID NO 60
<211> LENGTH: 482
<212> TYPE: DNA
<213> ORGANISM: Mus musculus
<220> FEATURE:
<221> NAME/KEY: promoter

```
<222> LOCATION: (1)..(482)
<223> OTHER INFORMATION: mouse activity dependent neurotrophic factor
      III (ADNF III) promoter

<400> SEQUENCE: 60
aattgttggg tgatgagaaa gagagctgtt tgccttccgt gttggtcatc aaggtctgcg      60
tgcattgcaa cagtgtcacc tgtgagttcc tgtgtctgaa gccgagaaga tccacaaaat    120
gaggcttttc catagttggt ttgtgttttt aacaagaaaa tggagaggct ttttgtttgt    180
ttttgttttt gttttttttgc ctctgacttc tctctgaaac cagccaacaa gtacaactag   240
caatttttaa agatttagca agaacttgca ctgagttttc atttacagga gcacaaataa    300
aaatatttga ttcaaaaatg catctgagtt cttttaattt ttcctgcagg agaaacctct    360
aaaagtcatt gccttgcaga gtttctggga atgcctgggg gaggagcctg gaacttgtaa    420
ctgcttgcct tgagtggcct tctcactctg gtttctgttc tgttttgttt cgtttgtttt    480
tt                                                                    482

<210> SEQ ID NO 61
<211> LENGTH: 50
<212> TYPE: DNA
<213> ORGANISM: Homo sapiens
<220> FEATURE:
<223> OTHER INFORMATION: H6, H7 and H2 clone human activity dependent
      neurotrophic factor III (ADNF III) polymorphic
      region
<220> FEATURE:
<221> NAME/KEY: variation
<222> LOCATION: (47)
<223> OTHER INFORMATION: polymorphic site a -> g transition

<400> SEQUENCE: 61
gagttaaact gagcagccaa caggcctaag tgccaggttc cctggcattg                50

<210> SEQ ID NO 62
<211> LENGTH: 50
<212> TYPE: DNA
<213> ORGANISM: Homo sapiens
<220> FEATURE:
<223> OTHER INFORMATION: H10 clone human activity dependent neurotrophic
      factor III (ADNF III) polymorphic region
<220> FEATURE:
<221> NAME/KEY: modified_base
<222> LOCATION: (13)
<223> OTHER INFORMATION: n = unknown
<220> FEATURE:
<221> NAME/KEY: modified_base
<222> LOCATION: (16)
<223> OTHER INFORMATION: n = unknown
<220> FEATURE:
<221> NAME/KEY: modified_base
<222> LOCATION: (20)
<223> OTHER INFORMATION: n = unknown
<220> FEATURE:
<221> NAME/KEY: modified_base
<222> LOCATION: (40)
<223> OTHER INFORMATION: n = unknown
<220> FEATURE:
<221> NAME/KEY: variation
<222> LOCATION: (47)
<223> OTHER INFORMATION: polymorphic site a -> g transition

<400> SEQUENCE: 62
gagttaaact gancanccan caggcctaag tgccaggttn cctggcgttg                50

<210> SEQ ID NO 63
<211> LENGTH: 50
<212> TYPE: DNA
```

```
<213> ORGANISM: Homo sapiens
<220> FEATURE:
<223> OTHER INFORMATION: H3, H12 and H4 clone human activity dependent
      neurotrophic factor III (ADNF III) polymorphic
      region
<220> FEATURE:
<221> NAME/KEY: variation
<222> LOCATION: ()
<223> OTHER INFORMATION: polymorphic site a -> g transition

<400> SEQUENCE: 63
gagttaaact gagcagccaa caggcctaag tgccaggttc cctggcgttg          50
```

What is claimed is:

1. An Activity Dependent Neurotrophic Factor (ADNF) III polypeptide, said polypeptide comprising the following amino acid sequence:

$(R^1)_x$-Asn-Ala-Pro-Val-Ser-Ile-Pro-Gln-$(R^2)_y$ (SEQ ID NO:10) in which:

$R^1$ is an amino acid sequence comprising from 1 to about 40 amino acids wherein each amino acid is independently selected from the group consisting of naturally occurring amino acids and amino acid analogs;

$R^2$ is an amino acid sequence comprising from 1 to about 40 amino acids wherein each amino acid is independently selected from the group consisting of naturally occurring amino acids and amino acid analogs; and x and y are independently selected and are equal to zero or one.

2. The ADNF III polypeptide in accordance with claim 1 wherein:

x and y are both zero (SEQ ID NO:6).

3. The ADNF III polypeptide in accordance with claim 1 wherein:

x is one;

$R^1$ is Gly-Gly-; and y is zero (SEQ ID NO:33).

4. The ADNF III polypeptide in accordance with claim 1 wherein:

x is one;

$R^1$ is Leu-Gly-Gly-;

y is one; and $R^2$ is -Gln-Ser (SEQ ID NO:34).

5. The ADNF III polypeptide in accordance with claim 1 wherein:

x is one;

$R^1$ is Leu-Gly-Leu-Gly-Gly- (SEQ ID NO:17);

y is one; and $R^2$ is -Gln-Ser (SEQ ID NO:35).

6. The ADNF III polypeptide in accordance with claim 1 wherein:

x is one;

$R^1$ is Ser-Val-Arg-Leu-Gly-Leu-Gly-Gly- (SEQ ID NO:18);

y is one; and $R^2$ is -Gln-Ser (SEQ ID NO:12).

7. The isolated ADNF III polypeptide in accordance with claim 1, wherein said ADNF III polypeptide has an amino acid sequence comprising SEQ ID NO:1, SEQ ID NO:57 or SEQ ID NO:59.

8. The isolated ADNF III polypeptide in accordance with claim 1, wherein said ADNF III polypeptide has an amino acid sequence comprising SEQ ID NO:3 or SEQ ID NO:55.

9. The isolated ADNF III polypeptide of claim 1, wherein said ADNF III polypeptide is encoded by a nucleic acid having a nucleic acid sequence comprising SEQ ID NO:2, SEQ ID NO:4, SEQ ID NO:54, SEQ ID NO:56, or SEQ ID NO:58.

10. The isolated ADNF III polypeptide of claim 1, wherein said ADNF III polypeptide is recombinantly reproduced.

11. A composition comprising a pharmaceutically acceptable excipient and an Activity Dependent Neurotrophic Factor (ADNF) III polypeptide, wherein said ADNF III polypeptide comprises the following amino acid sequence:

$(R^1)_x$-Asn-Ala-Pro-Val-Ser-Ile-Pro-Gln-$(R^2)_y$ (SEQ ID NO:10) in which:

$R^1$ is an amino acid sequence comprising from 1 to about 40 amino acids wherein each amino acid is independently selected from the group consisting of naturally occurring amino acids and amino acid analogs;

$R^2$ is an amino acid sequence comprising from 1 to about 40-amino acids wherein each amino acid is independently selected from the group consisting of naturally occurring amino acids and amino acid analogs; and x and y are independently selected and are equal to zero or one.

12. The composition in accordance with claim 11, wherein:

x and y are both zero (SEQ ID NO:6).

13. The isolated ADNF III composition in accordance with claim 11, wherein said ADNF III polypeptide has an amino acid sequence comprising SEQ ID NO:1, SEQ ID NO:57 or SEQ ID NO:59.

14. The isolated ADNF III composition in accordance with claim 11, wherein said ADNF III polypeptide has an amino acid sequence comprising SEQ ID NO:3 or SEQ ID NO:55.

15. The isolated ADNF III composition of claim 11, wherein said ADNF III polypeptide is recombinantly reproduced.

16. An isolated ADNF III polypeptide, said ADNF III polypeptide being encoded by an isolated nucleic acid, wherein said nucleic acid specifically hybridizes under highly stringent conditions to a nucleotide sequence of SEQ ID NO:2 or SEQ ID NO:4, wherein the hybridization reaction is incubated at 42° C. in a solution comprising 50% formamide, 5×SSC, and 1% SDS and washed at 65° C. in a solution comprising 0.2×SSC and 0.1% SDS at 65° C.

* * * * *